(12) United States Patent
Babinski et al.

(10) Patent No.: US 7,579,468 B2
(45) Date of Patent: Aug. 25, 2009

(54) METHODS OF MODULATING NEUROTROPHIN-MEDIATED ACTIVITY

(75) Inventors: Kazimierz Babinski, Dorval (CA); Rahul Vohra, Kanata (CA); Xilin Cui, Orleans (CA); Daniel Scott Auld, Montreal (CA); Nachhattarpal Gill, Ottawa (CA)

(73) Assignee: PainCeptor Pharma Corporation, Quebec (CA)

( * ) Notice: Subject to any disclaimer, the term of this patent is extended or adjusted under 35 U.S.C. 154(b) by 197 days.

(21) Appl. No.: 11/521,592

(22) Filed: Sep. 14, 2006

(65) Prior Publication Data

US 2007/0093474 A1    Apr. 26, 2007

Related U.S. Application Data

(60) Provisional application No. 60/718,256, filed on Sep. 15, 2005.

(51) Int. Cl.
*C07D 219/00*    (2006.01)

(52) U.S. Cl. ...................... 546/103; 546/102

(58) Field of Classification Search .................. 514/183
See application file for complete search history.

(56) References Cited

U.S. PATENT DOCUMENTS

| | | |
|---|---|---|
| 3,821,383 A | 6/1974 | Sestanj et al. |
| 4,006,238 A | 2/1977 | Wade |
| 4,204,063 A | 5/1980 | Brana et al. |
| 4,254,109 A | 3/1981 | Sestanj et al. |
| 4,874,863 A | 10/1989 | Brana et al. |
| 5,076,831 A | 12/1991 | Saupe et al. |
| 5,183,821 A | 2/1993 | Brana et al. |
| 5,342,942 A | 8/1994 | Jaen et al. |
| 5,420,137 A | 5/1995 | Brana et al. |
| 5,552,544 A | 9/1996 | Bra na et al. |
| 5,554,622 A | 9/1996 | Bra na et al. |
| 5,616,589 A | 4/1997 | Keilhauer et al. |
| 6,015,458 A | 1/2000 | Schulz et al. |
| 6,029,114 A | 2/2000 | Shamovsky et al. |
| 6,040,331 A | 3/2000 | Yamamoto et al. |
| 6,291,247 B1 | 9/2001 | Riopelle et al. |
| 6,300,331 B1 | 10/2001 | Noguchi et al. |
| 6,403,604 B1 | 6/2002 | Yang et al. |
| 6,403,797 B1 | 6/2002 | Sandefur et al. |
| 6,468,990 B1 | 10/2002 | Ross et al. |
| 6,492,380 B1 | 12/2002 | Ross et al. |
| 6,825,207 B2 | 11/2004 | Yang et al. |
| 6,855,720 B2 | 2/2005 | Yang |
| 7,148,352 B2 | 12/2006 | Ross et al. |
| 7,291,629 B2 | 11/2007 | Tehim et al. |
| 2007/0078137 A1 | 4/2007 | Ross et al. |

FOREIGN PATENT DOCUMENTS

| | | |
|---|---|---|
| AU | 199943963 B2 | 4/2000 |
| DE | 2323555 | 8/1974 |
| DE | 3707652 A1 | 9/1988 |
| EP | 0206322 B1 | 12/1986 |
| EP | 0268093 B1 | 5/1988 |
| EP | 0430004 A2 | 6/1991 |
| EP | 0728745 A1 | 8/1996 |
| FR | 2521139 | 8/1983 |
| JP | 2002-154984 | 5/2002 |
| WO | WO-98/06048 A2 | 2/1998 |
| WO | WO-98/17278 A1 | 4/1998 |
| WO | WO-00/00472 A1 | 1/2000 |
| WO | WO-00/69828 A1 | 11/2000 |
| WO | WO-00/69829 A1 | 11/2000 |
| WO | WO-03/101998 A1 | 12/2003 |
| WO | WO-2005/076695 A2 | 8/2005 |
| WO | WO-2006/027628 A2 | 3/2006 |
| WO | WO-2007/030940 A2 | 3/2007 |

OTHER PUBLICATIONS

Ares, Jeffrey J. et al., "Synthesis and Biological Evaluation of Irreversible Inhibitors of Aldose Reductase," *J. Med. Chem.*, vol. 29:2384-2389 (1986).

Biczók, László et al., "Effect of molecular structure and hydrogen bonding on the fluorescence of hydroxy-substituted naphthalimides," *Phys. Chem. Chem. Phys.*, vol. 1:4759-4766 (1999).

Braña, Mibuel F. et al., "Enediynes as Antitumor Compounds: Synthesis of Tetrahydropyridine Derivatives," *J. Org. Chem.*, vol. 61:1369-1374 (1996).

Braña, Mibuel Fernández et al., "Synthesis and cytostatic activity of benz(de)iso-quinolin-1,3-diones. Structure-activity relationships," *Eur. J. Med. Chem.*, vol. 16(3):207-212 (1981).

Chapman, James M. Jr. et al., "Hypolipidemic Activity of Phthalimide Derivatives IV: Further Chemical Modification and Investigation of the Hypolipidemic Activity of N-Substituted Imides," *Journal of Pharmaceutical Sciences*, vol. 72(11):1344-1347 (1983).

Chapman, James M. Jr. et al., "Hypolipidemic Activity of Phthalimide Derivatives V: Reduced and Hydrolytic Products of Simple Cyclic Imides," *Journal of Pharmaceutical Sciences*, vol. 73(10):1482-1484 (1984).

(Continued)

*Primary Examiner*—Sreeni Padmanabhan
*Assistant Examiner*—Timothy E Betton
(74) *Attorney, Agent, or Firm*—Lahive & Cockfield, LLP; Cynthia L. Kanik; Brian C. Trinque

(57) ABSTRACT

Disclosed are compositions which modulate the interaction with nerve growth factor and precursors thereof with neurotrophic receptors. Also disclosed are methods of using the compositions of the invention, including methods of administration.

44 Claims, 15 Drawing Sheets

OTHER PUBLICATIONS

Costi, M.P. et al., "Naphthalimido derivatives as antifolate thymidylate synthase inhibitors," *Eur. J. Med. Chem.*, vol. 31:1011-1016 (1996).

Donkor, Isaac O. et al., "Synthesis and biological activities of aldose reductase inhibitors bearing acyl benzenesulfonamides as carboxylic acid surrogates," *Eur. J. Med. Chem.*, vol. 33:15-22 (1998).

Donkor, Isaac O. et al., "Synthesis and biological activity of aldose reductase inhibitors with Michael acceptor substituents," *Eur. J. Med. Chem.*, vol. 34:235-243 (1999).

Dubey, Krishna K. et al., "A novel bifunctional fluorescent tag for use in molecular biology," *Indian Journal of Chemistry*, vol. 34B:876-878 (1995).

El-Naggar, A.M. et al., "Synthesis and biological activity of some new 3,6-dinitro-1:8-naphthaloyl- and 3,6-diamino-1:8-naphthaloylamino acids and dipeptide derivatives," *International Journal of Peptide & Protein Research*, vol. 20(1):1-7 (1982).

El-Naggar, A.M. et al., "Synthesis of some 3-hydroxynaphthalene-2-carbonylamino acid and dipeptide derivatives," *Int. J. Peptide Protein Res.*, vol. 22:251-256 (1983).

Hodgkiss, R.J. et al., "Fluorescent Markers for Hypoxic Cells, A Study of Novel Heterocyclic Compounds that Undergo Bio-Reductive Binding," *Biochemical Pharmacology*, vol. 41(4):533-541 (1991).

Hodgkiss, R.J. et al., "Toxicity of 3-Nitronaphthalimides to V79 379A Chinese Hamster Cells," *Biochemical Pharmacology*, vol. 36(9):1483-1487 (1987).

Jaen, Juan C. et al., "Kynurenic Acid Derivatives Inhibit the Binding of Nerve Growth Factor (NGF) to the Low-Affinity p75 NGF Receptor," *J. Med. Chem.*, vol. 38:4439-4445 (1995).

Kador, Peter F. et al., "Irreversible Aldose Reductase Inhibitors," *Enzymology and Molecular Biology of Carbonyl Metabolism*, pp. 353-365 (1987).

LeSauteur, Lynne et al., "Small Peptide Mimics of Nerve Growth Factor Bind TrkA Receptors and Affect Biological Responses," *The Journal of Biological Chemistry*, vol. 270(12):6564-6569 (1995).

Nishizaki, S., "Infrared spectra of N-substituted naphthalimides," *Nippon Kagaku Zasshi*, vol. 86(7):696-699 (1965).

Owolabi, Joshua B. et al., "Characterization of Antiallodynic Actions of ALE-0540, a Novel Nerve Growth Factor Receptor Antagbonist, in the Rat," *The Journal of Pharmacology and Experimental Therapeutics*, vol. 289(3):1271-1276 (1999).

Spiegel, Katharyn et al., "PD 90780, A Nonpeptide Inhibitor of Nerve Growth Factor's Binding to the P75 NGF Receptor," *Blochemical and Biophysical Research Communciations*, vol. 217(2):488-494 (1995).

Szadowski, Jerzy et al., "Properties of monoazo pigments containing heterocyclic amide groups," CAplus Accession No. 108:154305 (1978).

Szadowski, Jerzy et al., Przemysl Chemizny, vol. 57(2):70-74 (1978).

Tyman, John Henry Paul, "Fluorescent naphthalimide dyes," CAplus Accession No. 108:7506 (1997).

International Search Report for Application No. PCT/CA2006/001517, dated Jan. 30, 2007.

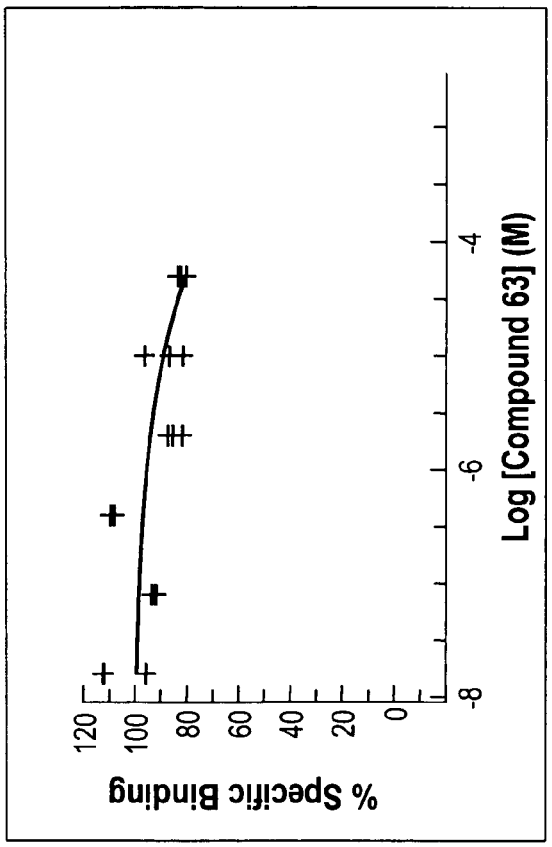

METHODS OF MODULATING NEUROTROPHIN-MEDIATED ACTIVITY

RELATED APPLICATION

This application claims priority to U.S. Provisional Application No. 60/718,256, filed Sep. 15, 2005, entitled "METHODS OF MODULATING NEUROTROPHIN-MEDIATED ACTIVITY." The contents of any patents, patent applications, and references cited throughout this specification are hereby incorporated by reference in their entireties.

TECHNICAL FIELD

The present invention relates to compositions which modulate the interaction of nerve growth factor, and precursors thereof, with the receptor TrkA, as well as the common neurotrophin receptor $p75^{NTR}$, and methods of use thereof.

BACKGROUND

The neurotrophins are a family of structurally and functionally related proteins, including Nerve Growth Factor (NGF), Brain-Derived Neurotrophic Factor (BDNF), Neurotrophin-3 (NT-3), Neurotrophin-4/5 (NT-4/5) and Neurotrophin-6 (NT-6). These proteins promote the survival and differentiation of diverse neuronal populations in both the peripheral and central nervous systems and are involved in the pathogenesis of diverse neurological disorders (Hefti, J. Neurosci. 6:2155-2162 (1986); Hefti and Weiner, Annals of Neurology 20:275-281 (1986); Levi-Montalcini, EMBO J. 6:1145-1154 (1987); Barde, Neuron 2:1525-1534 (1989); Leibrock et al., Nature 341:149-152 (1989); Maisonpierre et al., Science 247:1446-1451 (1990); Rosenthal et al., Neuron 4:767-773 (1990); Hohn et al., Nature 344:339-341 (1990); Gotz et al., Nature 372:266-269 (1994); Maness et al., Neurosci. Biobehav. Rev. 18:143-159 (1994); Dechant et al., Nature Neurosci. 5:1131-1136 (2002)). This broad spectrum of biological activities exerted by the neurotrophins results from their ability to bind and activate two structurally unrelated receptor types, the p75 neurotrophin receptor ($p75^{NTR}$) and the three members of the Trk receptor family of tyrosine kinases (Kaplan et al., Curr. Opin. Cell Biol. 9:213-221 (1997); Friedman et al., Exp. Cell Res. 253:131-142 (1999); Patapoutian et al., Curr. Opin. Neurobiol. 11:272-280 (2001)).

While NGF was initially studied for its essential role in neuronal growth and survival, recent reports indicate that this neurotrophin may also play a role in inflammation and disorders of the respiratory, the genitourinary and the gastrointestinal systems. For example, in the gastrointestinal tract, neurotrophins and neurotrophic factors regulate neuropeptide expression, interact with immunoregulatory cells and epithelial cells, and regulate motility during inflammation (Reinshagen, M. et al., Curr. Opin. Investig. Drugs. 2002; 3(4): 565-568). NGF has been shown to play a role in bladder overactivity (Lamb, K. et al., J. Pain. 2004; 5(3): 150-156), bladder outlet obstruction (Kim, J. C. et al., BJU Int. 2004; 94(6): 915-918), pancreatic cancer (Shi, X. et al., Pancreatology. 2001; 1(5):517-524), and intestinal inflammation (Lin, A. et al., Exp. Neurol. 2005; 191(2):337-43).

NGF is synthesized as a larger precursor form (referred to herein as "proNGF," also known as "preproNGF" or "propeptide NGF") which is then processed by proteolytic cleavages to produce the mature neurotrophic factor. This prepro region is located at the amino terminus of the precursor molecule and is needed for proper folding and secretion of the NGF protein. The mature form of NGF has arginine residues at its carboxy termini which requires that a leucine residue be inserted between the naturally occurring arginine and the hydrophilic spacer. The primary structure of proNGF has been deduced from the nucleotide sequence of the mouse NGF cDNA (Scott et al. Nature 302:538 (1983); Ullrich et al. Nature 303:821 (1983)).

The common neurotrophin receptor $p75^{NTR}$ is a transmembrane glycoprotein structurally related to the tumor necrosis factor and CD-40 receptors (Meakin and Shooter, Trends Neurosci. 15:323-331 (1992), Rydén and Ibáñez, J. Biol. Chem. 271:5623-5627 (1996)). As all neurotrophins bind to $p75^{NTR}$ with similar affinities (Rodrigues-Tébar et al., Neuron 4:487-492 (1990); Hallbook et al., Neuron 6:845-858 (1991); Rodrigues-Tébar et al., EMBO J. 11:917-922 (1992); Ibáñez, Trends Biotech. 13:217-227 (1995)), neurotrophin specificity is conventionally thought to be conferred by the binding selectivity for Trk receptors which are differentially expressed in different neuronal populations (Ibáñez, Trends Biotech. 13:217-227 (1995)). However, accumulated experimental data on neurotrophin activity reveal important functional aspects of $p75^{NTR}$ (Heldin et al., J. Biol. Chem. 264: 8905-8912 (1989); Jing et al., Neuron 9:1067-1079 (1992); Herrmann et al., Mol. Biol. 4:1205-1216 (1993); Barker and Shooter, Neuron 13:203-215 (1994); Dobrowsky et al., Science 265:1596-1599 (1994), Matsumoto et al., Cancer Res. 55:1798-1806 (1995); Marchetti et al., Cancer Res. 56:2856-2863 (1996); Washiyama et al., Amer. J. Path. 148:929-940 (1996)). The common neurotrophin receptor enhances functions and increases binding specificity of Trk receptors (Barker and Shooter, Neuron 13:203-215 (1994); Mahadeo et al., J. Biol. Chem. 269:6884-6891 (1994); Chao and Hempstead, Trends Neurosci. 18:321-326 (1995); Rydén and Ibáñez, J. Biol. Chem. 271:5623-5627 (1996)). In addition, $p75^{NTR}$ possesses unique, neurotrophin dependent, Trk-independent signaling properties which involve ceramide production through activation of the sphingomyelin cycle (Dobrowsky et al., Science 265:1596-1599 (1994)), apoptosis (cell death) (Cassacia-Bonnefil et al., Nature 383:716-719 (1996)), and activation of the transcription factor NFKB (Carter et al., Science 272:542-545 (1996)).

Moreover, while initially studied primarily in neurons, $p75^{NTR}$ has also been found to play critical roles in vascular biology (von Schack et al., Nat. Neurosci. 4:977-978, 2001; Wan et al., Am. J. Pathol. 157:1247-1258, 2001), glial biology (Bentley et al., J. Neurosci. 20:7706-7715, 2000; Syroid et al., J. Neurosci. 20:5741-5747, 2000), the immune system (Tokuoka et al., Br. J. Pharmacol. 134:1580-1586, 2001), and tumor biology (Sakamoti et al., Oncol. Rep. 8:973-980, 2001; Descamps et al., J. Biol. Chem. 276:17864017870, 2001). For example, $p75^{NTR}$ has been demonstrated to participate in human melanoma progression (Herrmann et al., Mol. Biol. 4:1205-1216 (1993); Marchetti et al., Cancer Res. 56:2856-2863 (1996)). Furthermore, NGF and NT-3 increase the production of heparin by 70 W melanoma cells, which is associated with their metastatic potential (Marchetti et al., Cancer Res. 56:2856-2863 (1996)).

Unlike $p75^{NTR}$, the Trk receptors (TrkA, TrkB and TrkC) exhibit selectivity for specific neurotrophins. (Kaplan et al., Science 252:554-558 (1991); Klein et al., Cell 65:189-197 (1991); Klein et al., Neuron 8:947-956 (1992); Soppet et al., Cell 65:895-903 (1991); Squinto et al., Cell 65:885-893 (1991); Berkemeier et al., Neuron 7:857-866 (1991); Escandon et al., Neurosci. Res. 34:601-613 (1993); Lamballe et al., Cell 66:967-970 (1991)). For example, TrkA primarily binds NGF (Kaplan et al., 1991; Klein et al., 1991) and has been reported to bind NT-3 (J. Biol. Chem. 271(10):5623-7, 1996);

TrkB binds BDNF and NT-4/5 (Soppet et al., 1991; Squinto et al., 1991; Berkemeier et al., 1991; Escandon et al., 1993; Lamballe et al., 1991; Klein et al., 1992; Vale and Shooter, Methods Enzymol. 109:21-39 (1985); Barbacid, Oncogene 8:2033-2042 (1993)); and TrkC exclusively binds NT-3 (Lamballe et al., 1991; Vale and Shooter, 1985). This is particularly evident when the Trk receptors are coexpressed with the common neurotrophin receptor $p75^{NTR}$. (For review see Meakin and Shooter, 1992; Barbacid, 1993; Chao, 1994; Bradshaw et al., 1994; Ibáñez, 1995).

Biochemical experiments indicate that neurotrophin receptors form at least three different types of complexes: homodimers of Trk receptors, homomeric $p75^{NTR}$ receptors and mixed complexes of both Trk and $p75^{NTR}$. These complexes may coexist in cells and may be linked through biochemical equilibria. Functionally, their signaling has been shown to be independent, synergistic or antagonistic. The response of a cell to neurotrophins is thus determined by the quantitative and qualitative composition of its receptor complement in combination with biochemical equilibria between pools of active and inactive receptors (Dechant, Cell Tissue Res. 305:229-238, (2001)), as well as other cellular and biochemical components downstream of the neurotrophin receptors, e.g., the availability of proteins, lipids and inorganic molecules involved in signal transduction.

Due to the implication of NGF, and its precursor proNGF, binding to homomeric and heteromeric neurotrophin receptor complexes in various disease states, especially pain, inflammation, neurological disorders and disorders of the respiratory, genitourinary and gastrointestinal systems, a need exists for pharmaceutical agents and methods of use thereof for modulating the interactions of NGF with the common neurotrophin receptor $p75^{NTR}$, and the Trk receptor TrkA.

SUMMARY OF THE INVENTION

There remains a need for new treatments and therapies for neurotophin-mediated activity, and conditions, diseases and disorders related to neurotophin-mediated activity. There is also a need for compounds useful in the treatment or prevention or amelioration of one or more symptoms of pain, inflammatory disorders, neurological disorders, respiratory disorders, genitourinary disorders, and/or gastrointestinal disorders. Furthermore, there is a need for methods for modulating the activity of NGF, proNGF, $p75^{NTR}$, and/or TrkA, using the compounds provided herein.

In one aspect, the invention provides a compound of the invention of the Formula 1, Formula 3, Formula 4, Formula 6, Formula 7, Formula 11, Formula 13, Formula 14, Formula 7A, Formula 7B, Formula 10A, Formula 10B or Formula 11A, as well as the compounds of Table 1.

In another aspect, the invention provides a method of modulating the interaction of a neurotrophin and a neurotrophin receptor, comprising contacting cells expressing a neurotrophin receptor with an effective amount of a compound of the invention.

In one embodiment, the neurotrophin is nerve growth factor and/or precursors thereof. In another embodiment, the neurotrophin receptor is selected from the group consisting of $p75^{NTR}$ and TrkA. In yet another embodiment, the neurotrophin receptor is $p75^{NTR}$. In still another embodiment, the neurotrophin receptor is TrkA. In another embodiment the compound further modulates the interaction of NGF and/or proNGF with TrkA.

In another embodiment, the method is used to modulate a neurotrophin-mediated activity in a subject in need thereof. In another embodiment, the neurotrophin-mediated activity is associated with pain. In still another embodiment, the neurotrophin-mediated activity is associated with an inflammatory disorder. In another embodiment, the neurotrophin-mediated activity is associated with a neurological disorder.

In another embodiment, the pain treated by the compounds of the invention is selected from the group consisting of cutaneous pain, somatic pain, visceral pain and neuropathic pain. In another embodiment the pain is acute pain or chronic pain.

In still another embodiment, the cutaneous pain is associated with injury, disease, disorder or neoplasms of the skin, subcutaneous tissues and related organs. In another embodiment, the injury, disease or disorder of the skin, subcutaneous tissues and related organs is selected from the group consisting of traumas, cuts, lacerations, punctures, burns, surgical incisions, infections, psoriasis, eczema, and inflammation (e.g., acute inflammation).

In another embodiment, the somatic pain is associated with an injury, disease, disorder or neoplasms of the musculoskeletal and connective system. In another embodiment, the injury, disease or disorder of the musculoskeletal and connective system is selected from the group consisting of sprains, broken bones, arthritis, arthralgia, myalgia, chronic lower back pain, cancer-associated pain, dental pain, fibromyalgia, idiopathic pain disorder, chronic non-specific pain, post-operative pain, and referred pain.

In another embodiment, the visceral pain is associated with an injury, disease, disorder or neoplasms of the circulatory system, the respiratory system, the gastrointestinal system, or the genitourinary system. In one embodiment, the disease or disorder of the circulatory system treated by the compounds of the invention is selected from the group consisting of ischaemic heart disease, angina, acute myocardial infarction, cardiac arrhythmia, phlebitis, intermittent claudication, varicose veins and hemorrhoids. In one embodiment, the disease or disorder of the respiratory system treated by the compounds of the invention is selected from the group consisting of asthma, Chronic Obstructive Pulmonary Disease (COPD), respiratory infection, chronic bronchitis and emphysema. In one embodiment, the disease or disorder of the gastrointestinal system treated by the compounds of the invention is selected from the group consisting of gastritis, duodenitis, irritable bowel syndrome, colitis, Crohn's disease, ulcers and diverticulitis. In one embodiment, the disease or disorder of the genitourinary system treated by the compounds of the invention is selected from the group consisting of cystitis, urinary tract infections, glomuerulonephritis, polycystic kidney disease, and kidney stones.

In another embodiment, the neuropathic pain is associated with an injury, disease, disorder or neoplasms of the nervous system. In still another embodiment, the injury, disease or disorder of the nervous system is selected from the group consisting of neuralgia, neuropathy, headache, chronic cephalic pain, phantom limb pain and spinal cord injury.

In one embodiment, the inflammatory disorder treated by the compounds of the invention is selected from an inflammatory disorder of the skin and subcutaneous tissues, the musculoskeletal and connective tissue system, the respiratory system, the circulatory system, the genitourinary system, the gastrointestinal system or the nervous system. In one embodiment, the inflammatory disorder of the skin and subcutaneous tissues is selected from the group consisting of psoriasis, dermatitis and eczema. In one embodiment, the inflammatory disorder of the musculoskeletal and connective tissue system is selected from the group consisting of arthritis, gout, myositis, bursitis and synovitis. In one embodiment, the inflammatory disorder of the respiratory system treated by the compounds of the invention is selected from the group consisting of asthma, bronchitis, sinusitis, pharyngitis, rhinitis and respiratory infections. In another embodiment, the inflammatory disorder of the circulatory system is selected from the group consisting of vasculitis, artherosclerosis, phlebitis, carditis and coronary heart disease. In one embodiment, the inflammatory disorder of the gastrointestinal system treated by the compounds of the invention is selected from the group consisting of inflammatory bowel disorder, ulcerative colitis, Crohn's disease, diverticulitis, viral infection, bacterial infection, chronic hepatitis, gingivitis, stomatitis, and gastritis. In one embodiment, the inflammatory disorder of the genitourinary system treated by the compounds of the invention is selected from the group consisting of cystitis, nephritic syndrome, glomerulonephritis, urinary tract infection, prostatitis, salpingitis, endometriosis and cystinosis.

In another embodiment, the neurological disorder treated by the compounds of the invention is selected from the group consisting of schizophrenia, bipolar disorder, depression, Alzheimer's disease, epilepsy, multiple sclerosis, amyotrophic lateral sclerosis, stroke, cerebral ischemia, neuropathy, retinal pigment degeneration, glaucoma, cardiac arrhythmia, shingles, Huntington's chorea, and Parkinson's disease.

In another aspect, the invention provides a method of treating pain in a subject in need thereof, comprising administering to the subject an effective amount of a compound of the invention. In one embodiment, the pain is selected from the group consisting of cutaneous pain, somatic pain, visceral pain and neuropathic pain. In another embodiment, the pain is acute pain, breakthrough pain or chronic pain.

In another aspect, the invention provides a method of treating an inflammatory disorder in a subject in need thereof, comprising administering to the subject an effective amount of a compound of the invention. In one embodiment, the inflammatory disorder is inflammatory disorder of the musculoskeletal and connective tissue system, the respiratory system, the circulatory system, the genitourinary system, the gastrointestinal system or the nervous system.

In another aspect, the invention provides a method of treating a neurological disorder in a subject in need thereof, comprising administering an effective amount of a compound of the invention. In one embodiment, the neurological disorder is selected from the group consisting of schizophrenia, bipolar disorder, depression, Alzheimer's disease, epilepsy, multiple sclerosis, amyotrophic lateral sclerosis, stroke, cerebral ischemia, neuropathy, retinal pigment degeneration, glaucoma, cardiac arrhythmia, Huntington's chorea, and Parkinson's disease.

In another aspect, the invention provides a method of treating a disease or disorder associated with the genitourinary and/or gastrointestinal systems of a subject in need thereof, comprising administering to the subject an effective amount of a compound of the invention. In one embodiment, the disease or disorder of the gastrointestinal system is selected from the group consisting of gastritis, duodenitis, irritable bowel syndrome, colitis, Crohn's disease, ulcers and diverticulitis. In another embodiment the disease or disorder of the genitourinary system is selected from the group consisting of cystitis, urinary tract infections, glomuerulonephritis, polycystic kidney disease, kidney stones and cancers of the genitourinary system.

In another aspect, the invention provides a method comprising administering to the subject an additional therapeutic agent. In one embodiment, the additional therapeutic agent is selected from the group consisting of an analgesic, an anti-inflammatory agent, an anesthetic, a corticosteroid, an anti-convulsant, an antidepressant, an anti-nausea/anti-emetic agent, an anti-psychiatric agent, a cardiovascular agent and a cancer therapeutic.

BRIEF DESCRIPTION OF THE DRAWINGS

FIG. 8A shows a dose-response curve for Compound 63 from an individual NGF binding displacement experiment in PC12 cells as described in Example 1. The dose-response curve demonstrates that compound 63 effectively blocks NGF binding to cells expressing TrkA and p75.

FIG. 8B shows a dose-response curve for compound 63 from an individual NGF binding displacement experiment in HEK_trk cells as described in Example 1. The dose-response curve demonstrates that compound 63 effectively blocks NGF binding to TrkA.

DETAILED DESCRIPTION OF THE INVENTION

Figure 1B:
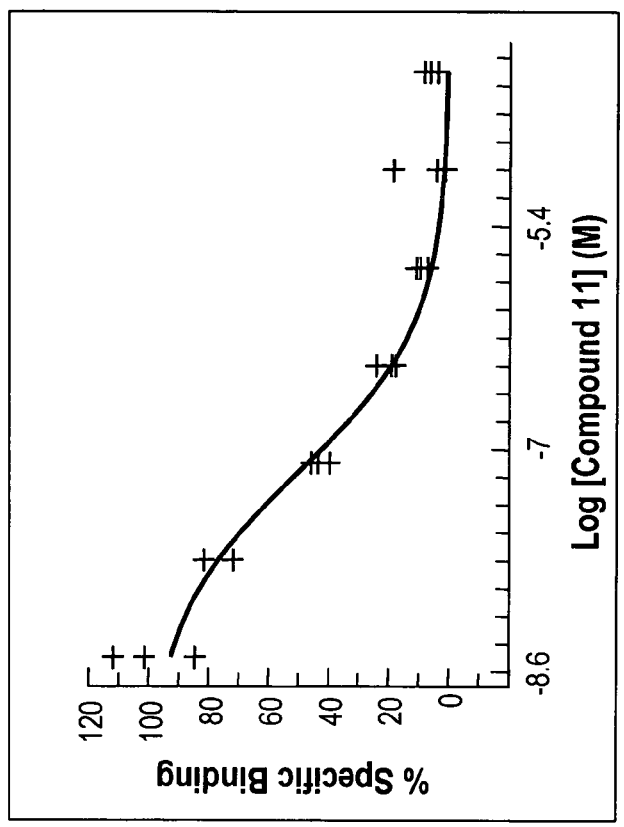
FIG. 1B shows a dose-response curve for Compound 11 from an individual NGF binding displacement experiment in PC12 cells as described in Example 1. The dose-response curve demonstrates that compound 11 effectively blocks NGF binding to cells expressing TrkA and p75.
Figure 1A:
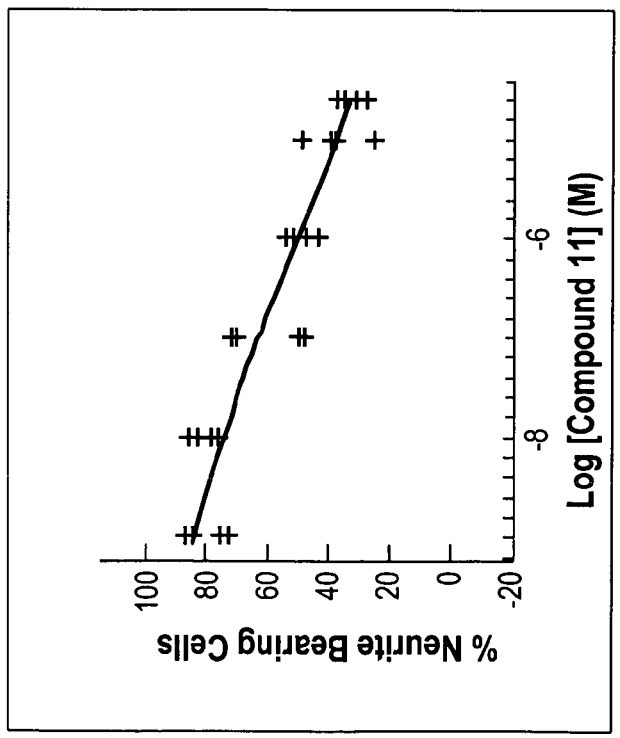
FIG. 1A shows a neurite outgrowth inhibition curve for Compound 11 resulting from an experiment as described in Example 4. The curve demonstrates that compound 11 effectively inhibits neurite outgrowth induced by NGF.
Figure 2A:
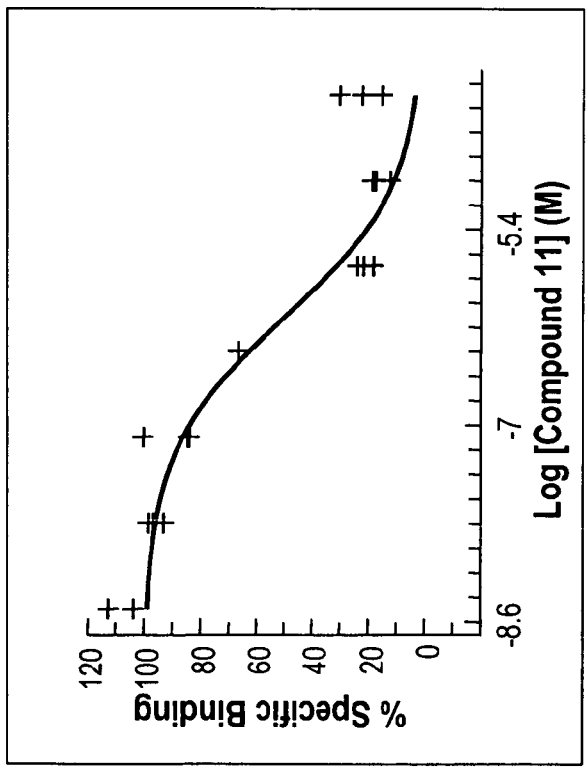
FIG. 2A shows a dose-response curve for Compound 11 from an individual NGF binding displacement experiment in A875 cells as described in Example 1. The dose-response curve demonstrates that compound 11 effectively blocks NGF binding to cells expressing p75.
Figure 2B:
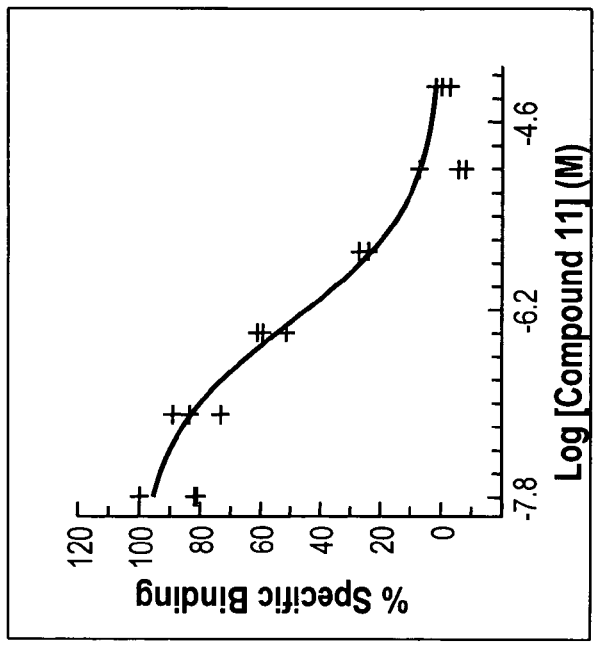
FIG. 2B shows a binding displacement curve for Compound 11 from an individual NGF binding displacement experiment in HEK_TrkA cells as described in Example 1. The dose-response curve demonstrates that Compound 11 effectively blocks NGF binding to TrkA.

The present invention relates to the discovery of compounds which modulate the interaction of a neurotrophin—either in its mature (e.g., NGF) or precursor (e.g., proNGF) form—with a neurotrophin receptor, for example, the common neurotrophin receptor $p75^{NTR}$ and/or a Trk receptor. Such compounds are of use, for example, for modulating the interaction of NGF and/or a precursor thereof (e.g., proNGF) to $p75^{NTR}$, and the compounds within the invention can also have the ability to modulate the interaction of NGF and/or proNGF with TrkA. For example, a compound that modulates the binding of NGF or proNGF to $p75^{NTR}$ can further modulate the binding of the neurotrophin to TrkA. Such compounds can also be used to treat a subject having a condition with at least one symptom that is directly or indirectly mediated, at least in part, by the interaction of NGF and/or a precursor thereof with $p75^{NTR}$ and/or TrkA.

Nerve growth factor (also referred to hereinafter as "NGF") is a prototypic neurotrophin, and is best known for its essential role during development of peripheral sensory and sympathetic neurons. NGF is produced as a high-molecular weight precursor (pro-NGF) that contains a pro-domain linked to the N-terminus which is cleaved by the endoprotease furin in the trans-Golgi network of neurons (Mowla et al., J. Biol. Chem. 276:12660-12666, 2001; Mowla et al., J. Neurosci. 19:2069-2080, 1999). Pro-NGF has been shown to be induced and secreted after injury to the CNS in an active form that is capable of triggering cell apoptosis (e.g., of neuronal cells and oligodendrocytes), and disruption of the interaction of pro-NGF and $p75^{NTR}$ has been demonstrated to rescue injured adult rat corticospinal neurons (e.g., Harrington et al., PNAS USA 101(16):6226-6230, 2004). Mature NGF regulates the phenotype (e.g., cell body and dendrite size, gene expression and neurotransmitter phenotype) of peripheral neurons and certain CNS neurons, notably, basal forebrain and striatal cholinergic neurons throughout the life of an animal (Miller et al., Neuron 32:767-770, 2001; Ruberti et al., J. Neurosci. 20(7):2589, 2000; Chen et al, J. Neurosci. 17(19):7288-96, 1997; Fagan et al., J. Neurosci. 17(20):7644-54, 1997). NGF has been implicated in the pathogenesis of Alzheimer's disease, epilepsy and pain (Ben Ari and Represa, TINS 13:312-318 (1990); McKee et al., Ann. Neurol. 30:156 (1991); Leven and Mendel, TINS 16:353-359 (1993); Woolf and Doubell, Current Opinions in Neurobiol. 4:525-534 (1994); Rashid et al., Proc. Natl. Acad. Sci. U.S.A. 92:9495-9499 (1995); McMahon et al., Nature Med. 1:774-780 (1995)). The interaction of NGF with its receptors is determined by distinct sequences within its primary amino acid structure. While several regions of NGF participate in the NGF/TrkA interaction, mutation studies suggest that relatively few key residues, namely those located in the NGF amino and carboxyl termini, are primarily required for high affinity binding to TrkA.

Recent results have also shown that NGF may play a role in inflammation and disorders of the respiratory, genitourinary and gastrointestinal systems. For example, in the gastrointestinal tract, neurotrophins and neurotrophic factors regulate neuropeptide expression, interact with immunoregulatory cells and epithelial cells, and regulate motility during inflammation (Reinshagen, M. et al., Curr. Opin. Investig. Drugs. 2002; 3(4): 565-568). NGF has been shown to be a potentially relevant treatment target for bladder overactivity (Lamb, K. et al., J. Pain. 2004; 5(3): 150-156). Studies by Kim et al. show that increases in NGF may be related to the irritative symptoms resulting from correction of bladder outlet obstruction (BJU Int. 2004; 94(6): 915-918). Shi et al. have demonstrated that NGF and its receptor are overexpressed in pancreatic cancer and contribute to its malignant phenotype (Pancreatology. 2001; 1(5):517-524). The potential of NGF as a neuroprotective factor in the enteric nervous system has been demonstrated, as has its role in the mechanism by which intestinal inflammation can give rise to a permanent imbalance between excitatory and inhibitory pathways, thus tending to compromise intestinal function (Maruccio, L. et al. Histol. Histopathol. 2004; 19(2):349-356; Lin, A. et al., Exp. Neurol. 2005; 191(2):337-43). NGF has also been shown to play an important role in the development of the rat ovary (Romero, C. et al., 2002; 143(4):1485-1494). Data has further suggested that NGF may play a role in inflammation, bronchial hyperresponsiveness and airway remodeling in asthma, and may help us to understand the neuro-immune cross-talk involved in chronic inflammatory airway diseases (Frossard, N. et al., Eur. J. Pharmacol. 2004; 500(1-3): 453-465).

It has been assumed, based on studies in the mouse submandibular gland that NGF in vivo is largely in the mature form of NGF, and that mature NGF accounts for the molecule's biological activity. However, it has been recently shown that proNGF is abundant in central nervous system tissues whereas mature NGF is undetectable, suggesting that proNGF may have a function distinct from its role as a precursor. Moreover, this data suggests that proNGF may be responsible for some of the biological activity normally attributed to mature NGF in vivo (Fahnestock, M. et al., J. Neurochem. 2004; 89(3):581-592; Fahnestock, M. et al., Prog. Brain Res. 2004; 146: 107-110). For example, it has been demonstrated that proNGF levels increase during the preclinical stage of Alzheimer's disease (Peng, S. et al., J. Neuropathol. Exp. Neurol. 2004 June; 63(6):641-9). Additionally, studies by Beattie et al. (Neuron 2002 Oct. 24; 36(3): 275-386) have shown that proNGF plays an important role in eliminating damaged cells by activating the apoptotic machinery via $p75^{NTR}$ after spinal cord injury.

Based on the above, there is a need for compositions which modulate the interaction of nerve growth factor, and precursors thereof, with the receptor TrkA, as well as the common neurotrophin receptor $p75^{NTR}$, and methods of use thereof.

Definitions

The term "electronegative atom," as used herein, refers to an atom which carries a partial or full negative charge in a particular compound under physiological conditions. The electronegative atom can be, for example, an oxygen atom, a nitrogen atom, a sulfur atom or a halogen atom, such as a fluorine, chlorine, bromine or iodine atom. Preferably, the electronegative atom is an oxygen atom. The term "electronegative functional group," as used herein, refers to a functional group which includes at least one electronegative atom. Electronegative groups include acid functional groups and other polar functional groups. For example, suitable electronegative functional groups include, but are not limited to, carbonyl, thiocarbonyl, ester, imino, amido, amine, carboxylic acid, sulfonic acid, sulfinic acid, sulfamic acid, phosphonic acid, boronic acid, sulfate ester, hydroxyl, mercapto, cyano, cyanate, thiocyanate, isocyanate, isothiocyanate, carbonate, nitrate and nitro groups. It is to be understood that, unless otherwise indicated, reference herein to an acidic functional group also encompasses salts of that functional group in combination with a suitable cation.

As used herein, the term "acid" refers to any substituent that can readily donate a hydrogen ion to another compound. Particularly preferred acid functional groups include carboxylic acid, sulfonic acid, sulfinic acid, sulfamic acid, phosphonic acid and boronic acid functional groups.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function. The term "substituted" is intended to describe moieties having substituents replacing a hydrogen on one or more atoms, e.g. C, O or N, of a molecule. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}$($C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety (C=O) may be further derivatized with an oxime moiety, e.g., an aldehyde moiety may be derivatized as its oxime ($-C=N-OH$) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

In a particular embodiment of the invention, the term "amine" or "amino" refers to substituents of the formulas $N(R^8)R^9$, $CH_2N(R^8)R^9$ and $CH(CH_3)N(R^8)R^9$, wherein $R^8$ and $R^9$ are each, independently, selected from the group consisting of —H and —($C_{1-4}$alkyl)$_{0-1}$G, wherein G is selected from the group consisting of —COOH, —H, —PO$_3$H, —SO$_3$H, —Br, —Cl, —F, —O—$C_{1-4}$alkyl, —S—$C_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or $N(R^8)R^9$ is pyrrolyl, tetrazolyl, pyrrolidinyl, pyrrolidinyl-2-one, dimethylpyrrolyl, imidazolyl, morpholino or

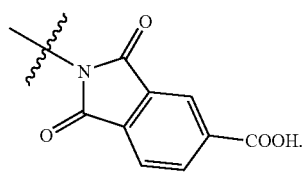

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

It will be noted that the structures of some of the compounds of this invention include asymmetric carbon atoms. It is to be understood accordingly that the isomers arising from such asymmetry (e.g., all enantiomers and diastereomers) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., $—CH_3$ and $—CH_2CH_2CH_2—$) can be combined to form a 3-methoxy-4-propoxybenzoic acid substituent; or the terms "acid" (i.e., —COOH) and $C_{1-6}$ (i.e., $—CH_2CH_3$) can be combined to form an ethyl ester substituent. It is to be understood that when combining functional groups and molecules to create a larger molecular architecture, hydrogens can be removed or added, as required to satisfy the valence of each atom.

As used herein, the term "pharmaceutically acceptable salts" refers to salts of the invention prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred salts are sodium, lysine and argentine salts of the compounds of the invention.

As used herein, the term "neurotrophic factor" or "neurotrophin" (also referred to herein as "NT") refers to members of a family of proteins, usually in the form of dimers, which are structurally homologous to NGF. The term includes the precursors (pro-neurotrophins, e.g., pro-NGF) and the mature proteins which include three surface 3-hairpin loops, a p-strand, an internal reverse turn region, and N- and C-termini. Neurotrophins promote at least one of the biological activities related to vertebrate neuron survival, differentiation, and function, as determined using assays described, for example, in US 2002/0169182A1 and Riopelle et al., Can J. of Phys. and Pharm. 60:707 (1982); Harrington et al. PNAS USA 101(16):6226-6230, (2004)). Neurotrophic factors include, for example, brain-derived neurotrophic factor (BDNF), NGF, neurotrophin 3 (NT-3), neurotrophin 4/5 (NT-4/5), and neurotrophin 6 (NT-6) (R. M. Lindsay et al.: TINS, vol. 17, p. 182 (1994) and R. M. Lindsay: Phil. Trans. R. Soc. Lond. B. vol. 351, p. 365-373 (1996)). In addition, ciliary neurotrophic factor (CNTF), glia-derived neurotrophic factor (GDNF), glia growth factor (GGF2), central nerve growth factor (AF-1), hepatocyte growth factor (HGF) (A. Ebens et al., Neuron, vol. 17, p. 1157-1172 (1996)) can also be considered as neurotrophic factors. Moreover, biotechnologically engineered products of the above neurotrophic factors, which are derived by a partial substitution, an addition, a deletion or a removal by conventional genetic engineering techniques, are also included within the scope of the neurotrophic factors of the present invention as far as such product shows biological activities of the naturally-occurred neurotrophic factors.

As used herein, the term "neurotrophin receptor" (also referred to herein as "NTR") is meant to refer to a receptor which binds a neurotrophin. In certain embodiments, the neurotrophin receptor is a member of the tyrosine kinase family of receptors, generally referred to as the "Trk" receptors or "Trks", which are expressed on cellular surfaces. The Trk family includes, but is not limited to, TrkA, TrkB, and TrkC. In a particular embodiment the neurotrophin receptor is TrkA. In other embodiments, the neurotrophin receptor is $p75^{NTR}$, also called p75 or low-affinity nerve growth factor receptor or common neurtotrophin receptor. These receptors may be from any animal species that expresses neurotrophin receptors (e.g. human, murine, rabbit, porcine, equine, etc.), and include full length receptors, their truncated and variant forms, such as those arising by alternate splicing and/or insertion, and naturally-occurring allelic variants, as well as functional derivatives of such receptors.

"Neurotrophin-mediated activity" is a biological activity that is normally modulated (e.g., inhibited or promoted), either directly or indirectly, in the presence of a neurotrophin. Neurotrophin-mediated activities include, for example, neurotrophin binding to the $p75^{NTR}$ receptor or neurotrophin binding to one of the Trk receptors (e.g., TrkA), the ability to promote neurotrophin receptor dimerization and/or phosphorylation, neuron survival, neuron differentiation including neuron process formation and neurite outgrowth, neurotransmission and biochemical changes such as enzyme induction. A biological activity that is mediated by a particular neurotrophin, e.g. NGF or pro-NGF, is referred to herein by reference to that neurotrophin, e.g. NGF-mediated activity. (It is noted that "NGF-mediated activity" also includes "proNGF-mediated activity.") To determine the ability of a compound to inhibit a neurotrophin-mediated activity, conventional in vitro and in vivo assays can be used. For example, a receptor binding assay, such as the assay described in US 2002/0169182 A1, can be used to assess the extent to which a compound inhibits neurotrophin/receptor binding. Inhibition of neurite survival and outgrowth can be determined using the in vitro assay described by Riopelle et al. in the Can. J. of Phys. and Pharm., 1982, 60: 707. Other examples of in vitro and in vivo assays for use in determining the ability of a compound to inhibit a neurotrophin-mediated activity are described in the "Exemplification of the Invention" section of the application.

"Neurotransmission," as used herein, is a process by which small signaling molecules, termed neurotransmitters, are rapidly passed in a regulated fashion from a neuron to another cell. Typically, following depolarization associated with an incoming action potential, a neurotransmitter is secreted from the presynaptic neuronal terminal. The neurotransmitter then diffuses across the synaptic cleft to act on specific receptors on the postsynaptic cell, which is most often a neuron but can also be another cell type (such as muscle fibers at the neuromuscular junction). The action of neurotransmitters can either be excitatory, depolarizing the postsynaptic cell, or inhibitory, resulting in hyperpolarization. Neurotransmission can be rapidly increased or decreased by neuromodulators, which typically act either pre-synaptically or post-synaptically. The neurotrophin family (notably NGF and BDNF) have been shown to have prominent neuromodulatory effects on diverse neuronal types (Lohof et al, Nature. 363(6427): 350-3 (1993); Li et al. J. Neurosci. 18(24):10231-40. (1998)). BDNF has also been shown to behave like a neurotransmitter, acting directly on target cells to alter their excitability by rapidly and directly gating ion certain ion channels (Rose et al., Bioessays. 26(11):1185-94. (2004)).

There are several simple fashions in which neurotransmission can be studied. The release of neurotransmitters from cultured neurons can be directly quantified using HPLC, radiolabeled neurotransmitters or other methodologies. Neurotransmission can be estimated by dyes such as FM 1-43, a fluorescent marker of synaptic vesicle cycling. Moreover, neurotransmission between neurons can be directly monitored using standard electrophysiological techniques, as can any direct neurotransmitter-like effects of neurotrophins on ion channel currents. These various methodologies have been used to study the effects of neurotrophins, such as BDNF and NGF, on neurotransmitter release and neurotransmission (Lohof et al.; Li et al.; Rose et al.).

The term "contacting" as used herein refers to bringing a compound of the invention and a target, e.g., NGF, $p75^{NTR}$ and/or TrkA together in such a manner that the compound can affect the activity of the target, either directly; i.e., by interacting with the target itself, or indirectly; i.e., by interacting with another target on which the catalytic activity of the target is dependent. For example, a compound of the invention may effect the activity of TrkA by contacting (e.g., binding to) TrkA directly, or by contacting (e.g., binding to) $p75^{NTR}$, which may effect the activity of TrkA. Such "contacting"" can be accomplished "in vitro," i.e., in a test tube, a petri dish or the like, or "in vivo," i.e., administered to a subject such as a mouse, rat or human. In a test tube, contacting may involve only a compound and a target of interest or it may involve whole cells. Cells may also be maintained or grown in cell culture dishes and contacted with a compound in that environment. "Contacting" can refer to a compound of the invention directly binding to a target, or being in the vicinity of a target.

Examples of neurotrophin-mediated activities include, but are not limited to, pain (e.g., inflammatory pain, acute pain, chronic malignant pain, chronic nonmalignant pain and neuropathic pain), inflammatory disorders, diseases and disorders of the genitourinary and gastrointestinal systems, and neurological disorders (e.g., neurodegenerative or neuropsychiatric disorders).

"Pain" is defined as an unpleasant sensory and emotional experience associated with actual or potential tissue damage, or described in terms of such damage (International Association for the Study of Pain—IASP). Pain is classified most often based on duration (i.e., acute vs. chronic pain) and/or the underlying pathophysiology (i.e., nociceptive vs. neuropathic pain).

Acute pain can be described as an unpleasant experience with emotional and cognitive, as well as sensory, features that occur in response to tissue trauma and disease and serves as a defensive mechanism. Acute pain is usually accompanied by a pathology (e.g., trauma, surgery, labor, medical procedures, acute disease states) and the pain resolves with healing of the underlying injury. Acute pain is mainly nociceptive, but may also be neuropathic.

Chronic pain is pain that extends beyond the period of healing, with levels of identified pathology that often are low and insufficient to explain the presence, intensity and/or extent of the pain (American Pain Society—APS). Unlike acute pain, chronic pain serves no adaptive purpose. Chronic pain may be nociceptive, neuropathic, or both and caused by injury (e.g., trauma or surgery), malignant conditions, or a variety of chronic conditions (e.g., arthritis, fibromyalgia and neuropathy). In some cases, chronic pain exists de novo with no apparent cause.

"Nociceptive pain" is pain that results from damage to tissues and organs. Nociceptive pain is caused by the ongoing activation of pain receptors in either the superficial or deep tissues of the body. Nociceptive pain is further characterized as "somatic pain", including "cutaneous pain" and "deep somatic pain", and "visceral pain".

"Somatic pain" includes "cutaneous pain" and "deep somatic pain." Cutaneous pain is caused by injury, diseases, disorders or neoplasms of the skin, subcutaneous tissues and related organs. Examples of conditions associated with cutaneous pain include, but are not limited to, cuts, burns, infections, lacerations, as well as traumatic injury and post-operative or surgical pain (e.g., at the site of incision).

"Deep somatic pain" results from injuries, diseases, disorders or neoplasms of the musculoskeletal tissues, including ligaments, tendons, bones, blood vessels and connective tissues. Examples of deep somatic pain or conditions associated with deep somatic pain include, but are not limited to, sprains, broken bones, arthralgia, vasculitis, myalgia and myofascial pain. Arthralgia refers to pain caused by a joint that has been injured (such as a contusion, break or dislocation) and/or inflamed (e.g., arthritis). Vaculitis refers to inflammation of blood vessels with pain. Myalgia refers to pain originating from the muscles. Myofascial pain refers to pain stemming from injury or inflammation of the fascia and/or muscles.

"Visceral" pain is associated with injury, inflammation, disease or neoplasms of the body organs and internal cavities, including but not limited to, the circulatory system, respiratory system, gastrointestinal system, genitourinary system, immune system, as well as the ear, nose and throat. Visceral pain can also be associated with infectious and parasitic diseases that affect the body organs and tissues. Visceral pain is extremely difficult to localize, and several injuries to visceral tissue exhibit "referred" pain, where the sensation is localized to an area completely unrelated to the site of injury. For example, myocardial ischaemia (the loss of blood flow to a part of the heart muscle tissue) is possibly the best known example of referred pain; the sensation can occur in the upper chest as a restricted feeling, or as an ache in the left shoulder, arm or even hand. Phantom limb pain is the sensation of pain from a limb that one no longer has or no longer gets physical signals from—an experience almost universally reported by amputees and quadriplegics.

"Neuropathic pain" or "neurogenic pain" is pain initiated or caused by a primary lesion, dysfunction or perturbation in the nervous system. "Neuropathic pain" can occur as a result of trauma, inflammation, disease or neoplasms of the peripheral nervous system ("peripheral neuropathic pain") and/or the central nervous system ("central pain"). For example, neuropathic pain can be caused by a nerve or nerves that are irritated, trapped, pinched, severed or inflamed (neuritis). There are many neuropathic pain syndromes, such as diabetic neuropathy, trigeminal neuralgia, postherpetic neuralgia ("shingles"), post-stroke pain, and complex regional pain syndromes (also called reflex sympathetic dystrophy or "RSD" and causalgia).

As used herein, the term "inflammatory disease or disorder" includes diseases or disorders which are caused, at least in part, or exacerbated by, inflammation, which is generally characterized by increased blood flow, edema, activation of immune cells (e.g., proliferation, cytokine production, or enhanced phagocytosis), heat, redness, swelling, pain and loss of function in the affected tissue and organ. The cause of inflammation may be due to physical damage, chemical substances, micro-organisms, tissue necrosis, cancer or other agents. Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some disorders may fall within one or more categories.

The terms "neurological disorder" and "neurodegenerative disorder" refer to injuries, diseases and dysfunctions of the nervous system, including the peripheral nervous system and central nervous system. Neurological disorders and neurodegenerative disorders include, but are not limited to, diseases and disorders that are associated with neurotrophin-mediated biological activity. Examples of neurological disorders include, but are not limited to, Alzheimer's disease, epilepsy, cancer, neuromuscular diseases, multiple sclerosis, amyotrophic lateral sclerosis, stroke, cerebral ischemia, neuropathy (e.g., chemotherapy-induced neuropathy, diabetic neuropathy), retinal pigment degeneration, Huntington's chorea, and Parkinson's disease, and ataxia-telangiectasia.

As used herein, "neuropathy" is defined as a failure of the nerves that carry information to and from the brain and spinal cord resulting in one or more of pain, loss of sensation, and inability to control muscles. In some cases, the failure of nerves that control blood vessels, intestines, and other organs results in abnormal blood pressure, digestion problems, and loss of other basic body processes. Peripheral neuropathy may involve damage to a single nerve or nerve group (mononeuropathy) or may affect multiple nerves (polyneuropathy).

The term "treated," "treating" or "treatment" includes the diminishment or alleviation of at least one symptom associated with the pain, inflammatory disorder, neurological disorder, genitourinary disorder or gastrointestinal disorder (e.g., associated with or caused by neurotrophin mediated activity) being treated. In certain embodiments, the treatment comprises the modulation of the interaction of a neurotrophin (e.g., monomer or dimer) and its receptor by an NT/NTR modulating compound, for example an NGF/NTR modulating compound, which would in turn diminish or alleviate at least one symptom directly or indirectly associated with or caused by the neurotrophin-mediated activity being treated. For example, treatment can be diminishment of one or several symptoms of a disorder or complete eradication of a disorder.

As used herein, the phrase "therapeutically effective amount" of the compound is the amount necessary or sufficient to treat or prevent pain, an inflammatory disorder, a neurological disorder, a gastrointestinal disorder or a genitourinary disorder, (e.g., to prevent the various morphological and somatic symptoms of a neurotrophin-mediated activity). In an example, an effective amount of the compound is the amount sufficient to alleviate at least one symptom of the disorder, e.g., pain, inflammation, a neurological disorder, a gastrointestinal disorder or a genitourinary disorder, in a subject.

The term "subject" is intended to include animals, which are capable of suffering from or afflicted with a neurotrophin-associated state or neurotrophin-associated disorder, or any disorder involving, directly or indirectly, neurotrophin signaling. In another embodiment, a subject is also intended to include animals, which are capable of suffering from pain, an inflammatory disorder, a neurological disorder, a respiratory disorder, a gastrointestinal disorder or a genitourinary disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from pain, inflammation, a neurological disorder, a gastrointestinal disorder or a genitourinary disorder (e.g. associated with neurotrophin-associated activity).

The language "NT/NTR modulator" refers to compounds that modulate, i.e., inhibit, promote or otherwise alter the interaction of a neurotrophin with a neurotrophin receptor. For example, "NGF/NTR modulator" refers to compounds that modulate, e.g., inhibit, promote, or otherwise alter, the interaction of NGF (or proNGF) with $p75^{NTR}$, TrkA, or $p75^{NTR}$ and TrkA. Examples of NGF/NTR modulators include compounds of Formulas 1, 3, 4, 6, 7, 11, 13, 14, 7A, 7B, 10A, 10B and 11A, including salts thereof, e.g., a pharmaceutically acceptable salt. Additional examples of NGF/NTR modulators include compounds of Table 1, or derivatives and fragments thereof, including salts thereof, e.g., a pharmaceutically acceptable salt. Compounds of Formulas 1, 3, 4, 6, 7, 11, 13, 14, 7A, 7B, 10A, 10B and 11A, as well as the compounds of Table 1, i.e., the NT/NTR modulators or NGF/NTR modulators of the invention, are also referred to herein as "compounds of the invention." In a particular embodiment, the NGF/NTR modulators of the invention, including the compounds of Table 1, can be used to treat a disease or disorder associated with pain, inflammation, neurological disorders, respiratory disorders, gastrointestinal disorders or genitourinary disorders in a subject in need thereof. In another embodiment, the compounds of the invention, including the compounds of Table 1, can be used to treat an inflammatory disorder in a subject in need thereof.

Modulators of Neurotrophin/Neurotrophin Receptor Interaction

In one aspect, the present invention provides compounds which modulate the interaction of a neurotrophin with a neurotrophin receptor. In certain embodiments, the compounds modulate the interaction of nerve growth factor (NGF) and/or a precursor thereof with a neurotrophin receptor (NTR). In other embodiments the compound modulates the interaction of NGF and/or a precursor thereof with the $p75^{NTR}$ receptor. In still other embodiments, the compound also modulates the interaction of NGF (or proNGF) with the TrkA receptor. In further embodiments, the compound modulates the interaction of NGF (or proNGF) with both the $p75^{NTR}$ and TrkA receptor.

In another aspect, the compounds of the invention treat pain, inflammatory disorders, neurological disorders, respiratory disorders, gastrointestinal disorders or genitourinary disorders in a subject in need thereof, comprising administering to the subject an effective amount of a compound of the invention.

Without being bound by theory, it is believed that an electronegative atom of the compound of the invention, e.g., an NGF/NTR modulator, bears a full or partial negative charge under physiological conditions and can, therefore, interact electrostatically with the positively charged side chain of an NGF lysine residue. Thus, there will be an interaction, such as, for example, a hydrogen bond, an ion/ion interaction, an ion/dipole interaction or a dipole/dipole interaction. The hydrophobic region or moiety of the NGF/NTR modulator can interact with a hydrophobic region of NGF via a hydrophobic interaction. Without being bound by theory, it is believed that compounds of the invention can interact with NGF in such a way as to interfere with, and thereby modulate, the interaction of NGF and p75$^{NTR}$ and/or TrkA.

In one embodiment, the compound of the invention is of the general Formula 1,

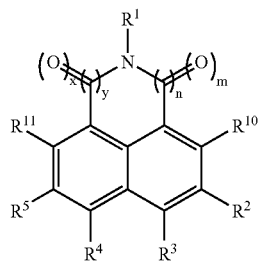

(1)

and pharmaceutically acceptable salts, enantiomers, stereoisomers, rotamers, tautomers, diastereomers, or racemates thereof;

wherein $R^1$ is selected from the group consisting of a hydrogen atom, —N(H)—, alkyl, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof; $R^2$, $R^3$, $R^4$, $R^5$, $R^{10}$ and $R^{11}$ are each, independently, selected from the group consisting of a hydrogen atom, —N(H)—, alkyl, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof; m and n are each, independently, 0 or 1; and x and y are each, independently, 0 or 1, provided that n and y are not 0 at the same time; or a pharmaceutically acceptable salt thereof.

In a particular embodiment of Formula 1, $R^1$ is selected from the group consisting of a hydrogen atom, $C_{1-6}$-alkyl, $C_{1-6}$-alkoxy or amino, wherein the alkyl, alkoxy or amino groups may be further substituted with $C_{1-6}$-alkyl, $C_{1-6}$-alkoxy, amino, halogen, hydroxyl, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, O—$C_{1-6}$-alkyl, S—$C_{1-6}$-alkyl, $C_{1-6}$-alkene, furanyl, thiophenyl, thiazolyl, nitro, tetrazolyl, $SO_2$—$C_{1-6}$-alkyl, $SO_3$—$C_{1-6}$-alkyl, $C_{1-6}$-alkyl-urea, $C_{1-6}$-alkyl-thiourea, morpholino, piperidinyl, piperazinyl or azepanyl;

$R^2$, $R^3$, $R^4$, $R^5$, $R^{10}$ and $R^{11}$ are each, independently, selected from the group consisting of a hydrogen atom, N($R^8$)$R^9$, $CH_2N(R^8)R^9$ and $CH(CH_3)N(R^8)R^9$, wherein $R^8$ and $R^9$ are each, independently, selected from the group consisting of —H and —($C_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-$C_6$-alkyl, —C(O)C$_{1-4}$alkyl-COOH, —C(O)C$_{1-4}$alkyl-COOH, —C(O)C$_1$-C$_4$-alkyl and —C(O)-aryl;

or N($R^8$)$R^9$ is pyrrolyl, tetrazolyl, pyrrolidinyl, pyrrolidin-2-one, dimethylpyrrolyl, imidazolyl, morpholino or

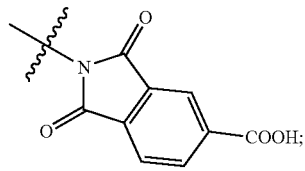

provided that at least one of $R^2$, $R^3$, $R^4$, $R^5$, $R^{10}$ and $R^{11}$ is not —H;

m and n are each, independently, 0 or 1; and x and y are each, independently, 0 or 1, provided that n and y are not 0 at the same time.

In another embodiment, the compound of the invention is of the general Formula 3,

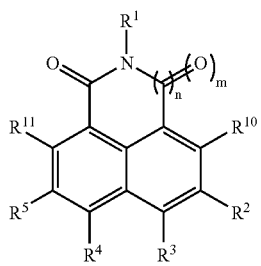

(3)

and pharmaceutically acceptable salts, enantiomers, stereoisomers, rotamers, tautomers, diastereomers, or racemates thereof;

wherein $R^1$ is selected from the group consisting of a hydrogen atom, —N(H)—, alkyl, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof; $R^2$, $R^3$, $R^4$, $R^5$, $R^{10}$ and $R^{11}$ are each, independently, selected from the group consisting of a hydrogen atom and N($R^8$)$R^9$, wherein $R^8$ and $R^9$ are each, independently, selected from the group consisting of H and —($C_{1-4}$alkyl)$_{0-1}$G, wherein G is selected from the group consisting of —COOH, —PO$_3$H$_2$, —SO$_3$H, —Br, —Cl, —F, —OC$_{1-4}$alkyl, —SC$_{1-4}$alkyl, aryl, substituted aryl, —C(O)OC$_{1-6}$-alkyl, —C(O)C$_1$-C$_4$-alkyl and —C(O)-aryl; esters thereof, salts thereof, and any combination thereof, provided that at least one of $R^2$, $R^3$, $R^4$, $R^5$, $R^{10}$ and $R^{11}$ is not H; and m and n are each, independently, 0 or 1; or a pharmaceutically acceptable salt thereof.

In a particular embodiment of Formula 3, $R^1$ is selected from the group consisting of a hydrogen atom, $C_{1-6}$-alkyl, $C_{1-6}$-alkoxy or amino, wherein the alkyl, alkoxy or amino groups may be further substituted with $C_{1-6}$-alkyl, $C_{1-6}$-alkoxy, amino, halogen, hydroxyl, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, O—$C_{1-6}$-alkyl, S—$C_{1-6}$-alkyl, $C_{1-6}$-alkene, furanyl, thiophenyl, thiazolyl, nitro, tetrazolyl, $SO_2$—$C_{1-6}$-alkyl, $SO_3$—$C_{1-6}$-alkyl, $C_{1-6}$-alkyl-urea, $C_{1-6}$-alkyl-thiourea, morpholino, piperidinyl, piperazinyl or azepanyl;

$R^2$, $R^3$, $R^4$, $R^5$, $R^{10}$ and $R^{11}$ are each, independently, selected from the group consisting of a hydrogen atom, C(O)N($R^8$)$R^9$, N($R^8$)$R^9$, CH$_2$N($R^8$)$R^9$ and CH(CH$_3$)N($R^8$)$R^9$, wherein $R^8$ and $R^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or N($R^8$)$R^9$ is pyrrolyl, tetrazolyl, pyrrolidinyl, pyrrolidin-2-one, dimethylpyrrolyl, imidazolyl, morpholino or

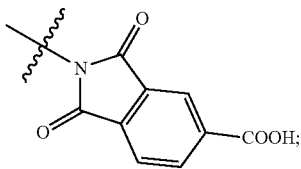

provided that at least one of $R^2$, $R^3$, $R^4$, $R^5$, $R^{10}$ and $R^{11}$ is not —H; and m and n are each, independently, 0 or 1.

In another embodiment of Formula 3, n and m are 1.

A preferred embodiment of Formula 3 is represented below as Formula 4,

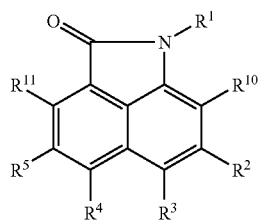

(4)

and pharmaceutically acceptable salts, enantiomers, stereoisomers, rotamers, tautomers, diastereomers, or racemates thereof;

wherein $R^1$ is selected from the group consisting of a hydrogen atom, alkyl, —N(H)—, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof; and $R^2$, $R^3$, $R^4$, $R^5$, $R^{10}$ and $R^{11}$ are each, independently, selected from the group consisting of a hydrogen atom and N($R^8$)$R^9$, wherein $R^8$ and $R^9$ are each, independently, selected from the group consisting of H and —(C$_{1-4}$alkyl)$_{0-1}$G, wherein G is selected from the group consisting of —COOH, —PO$_3$H, —SO$_3$H, —Br, —Cl, —F, —OC$_{1-4}$alkyl, —SC$_{1-4}$alkyl, —COOH, —SO$_3$H, —Br, is —Cl, —F, —OC$_{1-4}$alkyl, —SC$_{1-4}$alkyl, aryl, substituted aryl, —C(O)OC$_1$-C$_6$-alkyl, —C(O)C$_1$-C$_4$-alkyl and —C(O)-aryl; esters thereof, salts thereof, and any combination thereof, provided that at least one of $R^2$, $R^3$, $R^4$ and $R^5$ is not H; or a pharmaceutically acceptable salt thereof.

In a particular embodiment of Formula 4, $R^1$ is selected from the group consisting of a hydrogen atom, C$_{1-6}$-alkyl, C$_{1-6}$-alkoxy or amino, wherein the alkyl, alkoxy or amino groups may be further substituted with C$_{1-6}$-alkyl, C$_{1-6}$-alkoxy, amino, halogen, hydroxyl, acid, cyano, C$_{1-6}$-alkyl-sulfonamide, aryl, heteroaryl, C$_{3-6}$-cycloalkyl, C$_{3-6}$-heterocycloalkyl, C$_{1-6}$-alkyl-amide, C$_{1-6}$-alkyl-ester, O—C$_{1-6}$-alkyl, S—C$_{1-6}$-alkyl, C$_{1-6}$-alkene, furanyl, thiophenyl, thiazolyl, nitro, tetrazolyl, SO$_2$—C$_{1-6}$-alkyl, SO$_3$—C$_{1-6}$-alkyl, C$_{1-6}$-alkyl-urea, C$_{1-6}$-alkyl-thiourea, morpholino, piperidinyl, piperazinyl or azepanyl;

$R^2$, $R^3$, $R^4$, $R^5$, $R^{10}$ and $R^{11}$ are each, independently, selected from the group consisting of a hydrogen atom, C(O)N($R^8$)$R^9$, N($R^8$)$R^9$, CH$_2$N($R^8$)$R^9$ and CH(CH$_3$)N($R^8$)$R^9$, wherein $R^8$ and $R^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or N($R^8$)$R^9$ is pyrrolyl, tetrazolyl, pyrrolidinyl, pyrrolidin-2-one, dimethylpyrrolyl, imidazolyl, morpholino or

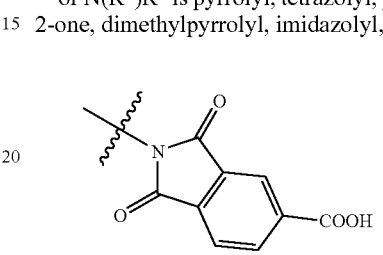

provided that at least one of $R^2$, $R^3$, $R^4$, $R^5$, $R^{10}$ and $R^{11}$ is not —H.

In another embodiment of Formula 4, $R^1$ is selected from the group consisting of (CH$_2$)$_n$COOH and —H, wherein n is 1, 2 or 3; and $R^2$, $R^3$, and $R^5$, are each, independently, selected from the group consisting of —N(H)C(O)C$_{1-6}$-alkyl and NH$_2$. In yet another embodiment of Formula 4, —N(H)C(O)C$_1$-C$_6$-alkyl is —N(H)C(O)CH$_3$, —N(H)C(O)-t-butyl or —N(H)C(O)CH$_2$-t-butyl.

Another preferred embodiment of Formula 3 is represented below as Formula 6,

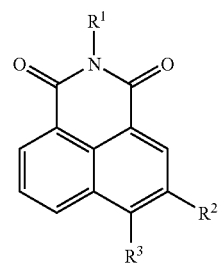

(6)

and pharmaceutically acceptable salts, enantiomers, stereoisomers, rotamers, tautomers, diastereomers, or racemates thereof;

wherein $R^1$ is selected from the group consisting of a hydrogen atom, alkyl, —N(H)—, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof; and $R^2$ and $R^3$ are each, independently, selected from the group consisting of a hydrogen atom and N($R^8$)$R^9$, wherein $R^8$ and $R^9$ are each, independently, selected from the group consisting of H and —(C$_{1-4}$alkyl)$_{0-1}$G, wherein G is selected from the group consisting of —COOH, —PO$_3$H, —SO$_3$H, —Br, —Cl, —F, —OC$_{1-4}$alkyl, —SC$_{1-4}$alkyl, —COOH, —SO$_3$H, —Br, —Cl, —F, —OC$_{1-4}$alkyl, —SC$_{1-4}$alkyl, aryl, substituted aryl, —C(O)OC$_1$-C$_6$-alkyl, —C(O)C$_1$-C$_4$-alkyl and —C(O)-aryl, esters thereof, salts thereof, and any combination thereof; provided that at least one of R$^2$ and R$^3$ is not H; or a pharmaceutically acceptable salt thereof.

In a particular embodiment of Formula 6, R$^1$ is selected from the group consisting of a hydrogen atom, C$_{1-6}$-alkyl, C$_{1-6}$-alkoxy or amino, wherein the alkyl, alkoxy or amino groups may be further substituted with C$_{1-6}$-alkyl, C$_{1-6}$-alkoxy, amino, halogen, hydroxyl, acid, cyano, C$_{1-6}$-alkyl-sulfonamide, aryl, heteroaryl, C$_{3-6}$-cycloalkyl, C$_{3-6}$-heterocycloalkyl, C$_{1-6}$-alkyl-amide, C$_{1-6}$-alkyl-ester, O—C$_{1-6}$-alkyl, S—C$_{1-6}$-alkyl, C$_{1-6}$-alkene, furanyl, thiophenyl, thiazolyl, nitro, tetrazolyl, SO$_2$—C$_{1-6}$-alkyl, SO$_3$—C$_{1-6}$-alkyl, C$_{1-6}$-alkyl-urea, C$_{1-6}$-alkyl-thiourea, morpholino, piperidinyl, piperazinyl or azepanyl;

R$^2$ and R$^3$ are each, independently, selected from the group consisting of a hydrogen atom, C(O)N(R$^8$)R$^9$, N(R$^8$)R$^9$, CH$_2$N(R$^8$)R$^9$ and CH(CH$_3$)N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or N(R$^8$)R$^9$ is pyrrolyl, tetrazolyl, pyrrolidinyl, pyrrolidin-2-one, dimethylpyrrolyl, imidazolyl, morpholino or

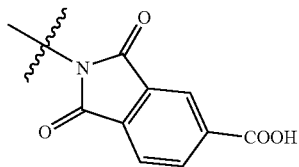

provided that at least one of R$^2$ and R$^3$ is not —H.

In one embodiment of Formula 6, R$^1$ is selected from the group consisting of C$_1$-C$_4$ alkyl, which may be independently substituted with one or more C$_1$-C$_4$-alkyl groups, NO$_2$, acid, NO$_2$, halogen; and R$^2$ and R$^3$ are each, independently, selected from the group consisting of a hydrogen atom, —NH$_2$, and —N(H)C(O)C$_1$-C$_6$-alkyl, provided that at least one of R$^2$ and R$^3$ is not —H.

In another embodiment of Formula 6, R$^2$ is selected from the group consisting of —NH$_2$, and —N(H)C(O)C$_1$-C$_6$-alkyl; and R$^3$ is —H. In still another embodiment of Formula 6, —N(H)C(O)C$_1$-C$_6$-alkyl is —N(H)C(O)CH$_3$, —N(H)C(O)-t-butyl or —N(H)C(O)CH$_2$-t-butyl.

Another preferred embodiment of Formula 3 is Formula 7,

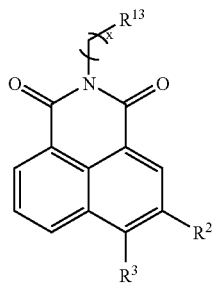

(7)

and pharmaceutically acceptable salts, enantiomers, stereoisomers, rotamers, tautomers, diastereomers, or racemates thereof;

wherein R$^{13}$ is selected from the group consisting of a hydrogen atom, alkyl, amino, alkoxy, —OH, —O—, —S—, —N(H)—, halogen, acid, cyano, sulfonamide, aryl, heteroaryl, cycloalkyl, heterocycloalkyl, amide, ester, furan, thiophene, thiazole, nitro, alkene, tetrazole, sulfone, urea, thiourea, morpholine, piperidine, piperazine, azepane, and any combination thereof; R$^2$ and R$^3$ are each, independently, selected from the group consisting of a hydrogen atom and N(R$^8$)R$^9$, wherein R$^8$ and R$^9$ are each, independently, selected from the group consisting of H and —(C$_{1-4}$alkyl)$_{0-1}$G, wherein G is selected from the group consisting of —COOH, —PO$_3$H, —SO$_3$H, —Br, —Cl, —F, —OC$_{1-4}$alkyl, —SC$_{1-4}$alkyl, —COOH, —SO$_3$H, —Br, —Cl, —F, —OC$_{1-4}$alkyl, —SC$_{1-4}$alkyl, aryl, substituted aryl, —C(O)OC$_1$-C$_6$-alkyl, —C(O)C$_1$-C$_4$-alkyl and —C(O)-aryl, esters thereof, salts thereof, and any combination thereof; provided that at least one of R$^2$ and R$^3$ is not H; and x is 1, 2, 3 or 4; or a pharmaceutically acceptable salt thereof.

In one embodiment of Formula 7, R$^{13}$ is selected from the group consisting of a hydrogen atom, C$_1$-C$_6$-alkyl, amino, C$_1$-C$_6$-alkoxy, —OH, -halogen, acid, cyano, C$_{1-6}$-alkyl-sulfonamide, aryl, heteroaryl, C$_{3-6}$-cycloalkyl, C$_{3-6}$-heterocycloalkyl, C$_{1-6}$-alkyl-amide, C$_{1-6}$-alkyl-ester, furanyl, thiophenyl, thiazolyl, nitro, C$_{1-6}$-alkene, tetrazolyl, SO$_2$—C$_{1-6}$-alkyl, SO$_3$—C$_{1-6}$-alkyl, C$_{1-6}$-alkyl-urea, C$_{1-6}$-alkyl-thiourea, morpholino, piperidinyl, piperazinyl, imidazolyl or azepanyl;

R$^2$ and R$^3$ are each, independently, selected from the group consisting of a hydrogen atom, C(O)N(R$^8$)R$^9$, N(R$^8$)R$^9$, CH$_2$N(R$^8$)R$^9$ and CH(CH$_3$)N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or N(R$^8$)R$^9$ is pyrrolyl, tetrazolyl, pyrrolidinyl, pyrrolidin-2-one, dimethylpyrrolyl, imidazolyl, morpholino or

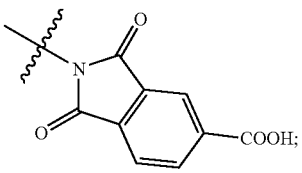

provided that at least one of R$^2$ and R$^3$ is not —H; and x is 1, 2, 3 or 4.

In one embodiment of Formula 7, R$^{13}$ is selected from the group consisting of —COOH, imidazolyl, —SO$_3$H, —OSO$_3$H, —OH, morpholino, piperazinyl, —PO$_3$H, —PO$_3$C$_{1-4}$alkyl and —NO$_2$; R$^2$ and R$^3$ are each, independently, selected from the group consisting of a hydrogen atom and NH$_2$, provided that at least one of R$^2$ and R$^3$ is not hydrogen; and x is 2, 3 or 4.

In another embodiment of Formula 7, R$^{13}$ is selected from the group consisting of —COOH and —COO$^-$Na$^+$; R$^1$ is —NH$_2$ or —N(H)C(O)CH$_3$; R$^3$ is a hydrogen atom; and x is 3. In yet another embodiment of Formula 7, R$^2$ is pyrrolyl or pyrrolyl substituted by one or more methyl groups; R$^3$ is —H; and x is 2 or 3. In still another embodiment of Formula 7, R$^2$ is NH$_2$ or NHC(O)CH$_3$ and R$^3$ is —H. In another embodiment of Formula 7, $R^2$ is pyrrolyl or 2,5-dimethyl-pyrrolyl and $R^3$ is —H; or $R^2$ is —H and $R^3$ is pyrrolyl or 2,5-dimethyl-pyrrolyl.

Another preferred embodiment of Formula 3 is Formula 11,

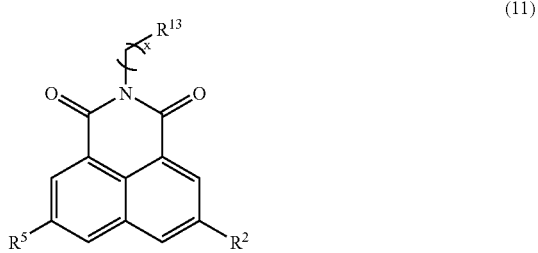

(11)

and pharmaceutically acceptable salts, enantiomers, stereoisomers, rotamers, tautomers, diastereomers, or racemates thereof;

wherein $R^{13}$ is selected from the group consisting of a hydrogen atom, alkyl, amino, alkoxy, —OH, —O—, —S—, —N(H)—, halogen, acid, cyano, sulfonamide, aryl, heteroaryl, cycloalkyl, heterocycloalkyl, amide, ester, furan, thiophene, thiazole, nitro, alkene, tetrazole, sulfone, urea, thiourea, morpholine, piperidine, piperazine, azepane, and any combination thereof; $R^2$ and $R^5$ are independently selected from the group consisting of halogen, —NH$_2$, —NO$_2$ and —N(H)C(O)C$_{1-4}$; and x is 0, 1, 2, 3 or 4; or a pharmaceutically acceptable salt thereof.

In a particular embodiment of Formula 11, $R^{13}$ is selected from the group consisting of a hydrogen atom, $C_{1-6}$-alkyl, amino, $C_{1-6}$-alkoxy, —OH, halogen, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, furanyl, thiophenyl, thiazolyl, nitro, $C_{1-6}$-alkene, tetrazolyl, SO$_2$—$C_{1-6}$-alkyl, SO$_3$—$C_{1-6}$-alkyl, $C_{1-6}$-alkyl-urea, $C_{1-6}$-alkyl-thiourea, morpholino, piperidinyl, piperazinyl, imidazolyl, or azepanyl;

$R^2$ and $R^5$ are independently selected from selected from the group consisting of a hydrogen atom, halogen, acid, CN, NO$_2$, C(O)N(R$^8$)R$^9$, N(R$^8$)R$^9$, CH$_2$N(8)R$^9$ and CH(CH$_3$)N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;

or N(R$^8$)R$^9$ is pyrrolyl, tetrazolyl, pyrrolidinyl, pyrrolidin-2-one, dimethylpyrrolyl, imidazolyl, morpholino,

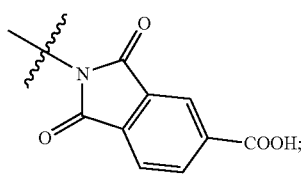

and x is 0, 1, 2, 3 or 4.

In one embodiment of Formula 11, $R^2$ and $R^5$ are independently selected from the group consisting of halogen, —NH$_2$, —NO$_2$, —N(H)C(O)C$_{1-6}$, NO$_2$, COOH, tetrazolyl and CN. In another embodiment of Formula 11, $R^{13}$ is selected from the group consisting of —COOH, —COO$^-$Na$^+$, COOCH$_3$, COOEt, PO$_3$H$_2$, imidazolyl, —SO$_3$H, —OSO$_3$H, —OH, morpholino, piperazinyl, —PO$_3$H, —PO$_3$C$_{1-4}$alkyl and —NO$_2$; and x is 2, 3 or 4. In yet another embodiment of Formula 11, x is 0, 1, 2, or 3; and $R^2$ and $R^5$ are both either —NH$_2$ or —N(H)C(O)CH$_3$. In still another embodiment of Formula 11, x is 2 or 3; and $R^2$ and $R^5$ are both either NO$_2$, NH$_2$ or N(H)C(O)CH$_3$.

In an additional embodiment of Formula 11, x is 2 or 3, $R^{13}$ is SO$_3$H, COOH, COO$^-$Na$^+$ or COOEt; and $R^2$ and $R^5$ are both either NO$_2$, NH$_2$ or N(H)C(O)CH$_3$. In another embodiment of Formula 11, x is 0, 1, 2, or 3; and one of $R^2$ and $R^5$ are NO$_2$ and the other is Br. In yet another embodiment of Formula 11, $R^2$ and $R^5$ are N(H)C(O)CH$_2$-t-butyl. In still another embodiment of Formula 11, $R^{13}$ is selected from the group consisting of —COOH and —COO$^-$Na$^+$; and x is 3.

In an additional embodiment of Formula 11, $R^{13}$ is COOH, COOEt, PO$_3$H$_2$, N(H)CH$_3$ or SO$_3$H. In another embodiment of Formula 11, $R^2$ and $R^5$ are both N(H)C(O)CH$_2$-t-butyl, NO$_2$, NH$_2$ or N(H)C(O)CH$_3$, or one of $R^2$ and $R^5$ is Br and the other is NO$_2$. In still another embodiment of Formula 11, x is 2 or 3. In yet another embodiment of Formula 11, $R^2$ and $R^5$ are C(O)N(R$^8$)R$^9$, wherein R$^8$ and R$^9$ are each, independently, selected from the group consisting of —H, C$_{1-4}$alkyl, phenyl and benzyl.

In another embodiment of Formula 11, $R^2$ and $R^5$ are C(O)NH$_2$; or $R^2$ and $R^5$ are C(O)N(H)-t-butyl.

Another preferred embodiment of Formula 3 is Formula 13,

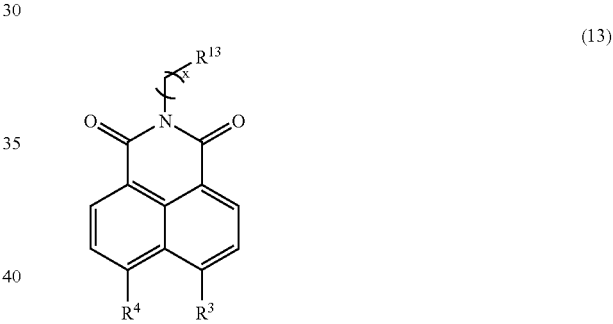

(13)

and pharmaceutically acceptable salts, enantiomers, stereoisomers, rotamers, tautomers, diastereomers, or racemates thereof;

wherein $R^{13}$ is selected from the group consisting of a hydrogen atom, alkyl, amino, alkoxy, —OH, —O—, —S—, —N(H)—, halogen, acid, cyano, sulfonamide, aryl, heteroaryl, cycloalkyl, heterocycloalkyl, amide, ester, furan, thiophene, thiazole, nitro, alkene, tetrazole, sulfone, urea, thiourea, morpholine, piperidine, piperazine, azepane, and any combination thereof; $R^3$ and $R^4$ are independently selected from the group consisting of halogen, —NH$_2$, —NO$_2$ and —N(H)C(O)C$_{1-4}$; and x is 1, 2, 3 or 4; or a pharmaceutically acceptable salt thereof.

In a particular embodiment of Formula 13, $R^{13}$ is selected from the group consisting of a hydrogen atom, $C_{1-6}$-alkyl, amino, $C_{1-6}$-alkoxy, —OH, halogen, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, furanyl, thiophenyl, thiazolyl, nitro, $C_{1-6}$-alkene, tetrazolyl, SO$_2$—$C_{1-6}$-alkyl, SO$_3$—$C_{1-6}$-alkyl, $C_{1-6}$-alkyl-urea, $C_{1-6}$-alkyl-thiourea, morpholino, piperidinyl, piperazinyl, imidazolyl, or azepanyl;

$R^3$ and $R^4$ are independently selected from the group consisting of a hydrogen atom, halogen, acid, CN, NO$_2$, C(O)N ($R^8$)$R^9$, N($R^8$)$R^9$, $CH_2$N($R^8$)$R^9$ and CH($CH_3$)N($R^8$)$R^9$, wherein $R^8$ and $R^9$ are each, independently, selected from the group consisting of —H and —($C_{1-4}$alkyl)$_{0-1}$G, wherein G is selected from the group consisting of —COOH, —H, —$PO_3$H, —$SO_3$H, —Br, —Cl, —F, —O$C_{1-4}$alkyl, —$SC_{1-4}$alkyl, aryl, —C(O)O$C_1$-$C_6$-alkyl, —C(O)$C_{1-4}$alkyl-COOH, —C(O)$C_1$-$C_4$-alkyl and —C(O)-aryl;

or N($R^8$)$R^9$ is pyrrolyl, tetrazolyl, pyrrolidinyl, pyrrolidin-2-one, dimethylpyrrolyl, imidazolyl, morpholino or

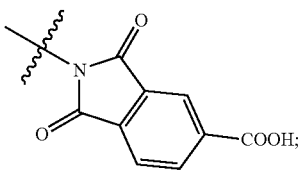

and x is 1, 2, 3 or 4.

In an another embodiment of Formula 13, $R^3$ and $R^4$ are independently selected from the group consisting of halogen, COOH, —$NH_2$, CN, —$NO_2$ and —N(H)C(O)$C_{1-4}$. In yet another embodiment of Formula 13, $R^{13}$ is selected from the group consisting of —COOH, —COO$^-$Na$^+$, imidazolyl, —$SO_3$H, —$OSO_3$H, —OH, morpholino, piperazinyl, —$PO_3$H, —$PO_3C_{1-4}$alkyl and —$NO_2$; and x is 2, 3 or 4. In still another embodiment of Formula 13, $R^{13}$ is selected from the group consisting of —COOH and —COO$^-$Na$^+$; and x is 3.

In one embodiment of Formula 13, $R^3$ and $R^4$ are both $NO_2$, $NH_2$, or COOH. In another embodiment of Formula 13, x is 3, and $R^{13}$ is COOH. In yet another embodiment of Formula 14, $R^3$ and $R^4$ are C(O)N($R^8$)$R^9$, wherein $R^8$ and $R^9$ are each, independently, selected from the group consisting of —H, $C_{1-4}$alkyl, phenyl and benzyl. In still another embodiment of Formula 35, wherein $R^3$ and $R^4$ are C(O)$NH_2$.

Another preferred embodiment of Formula 3 is Formula 14,

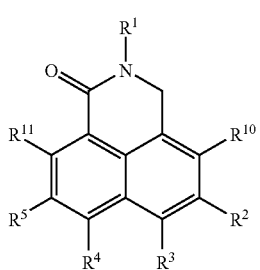

(14)

and pharmaceutically acceptable salts, enantiomers, stereoisomers, rotamers, tautomers, diastereomers, or racemates thereof;

wherein $R^1$, $R^2$, $R^3$, $R^4$, $R^5$, $R^{10}$ and $R^{11}$ are each, independently, selected from the group consisting of a hydrogen atom, —N(H)—, alkyl, alkoxy, amino, halogen, hydroxyl, acid, cyano, sulfonamide, aryl, heteroaryl, cycloalkyl, heterocycloalkyl, amide, ester, ether, thioether, alkene, furan, thiophene, thiazole, nitro, alkene, tetrazole, sulfone, urea, thiourea, morpholine, piperidine, piperazine, azepane, and any combination thereof or a pharmaceutically acceptable salt thereof.

In a particular embodiment of Formula 14, $R^1$ is selected from the group consisting of a hydrogen atom, $C_{1-6}$-alkyl, $C_{1-6}$-alkoxy or amino, wherein the alkyl, alkoxy or amino groups may be further substituted with $C_{1-6}$-alkyl, $C_{1-6}$-alkoxy, amino, halogen, hydroxyl, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, O—$C_{1-6}$-alkyl, S—$C_{1-6}$-alkyl, $C_{1-6}$-alkene, furanyl, thiophenyl, thiazolyl, nitro, tetrazolyl, $SO_2$—$C_{1-6}$-alkyl, $SO_3$—$C_{1-6}$-alkyl, $C_{1-6}$-alkyl-urea, $C_{1-6}$-alkyl-thiourea, morpholino, piperidinyl, piperazinyl or azepanyl; and $R^2$, $R^3$, $R^4$, $R^5$, $R^{10}$ and $R^{11}$ are each, independently, selected from the group consisting of a hydrogen atom, C(O)N($R^8$)$R^9$, N($R^8$)$R^9$, $CH_2$N($R^8$)$R^9$ and CH($CH_3$)N($R^8$)$R^9$, wherein $R^8$ and $R^9$ are each, independently, selected from the group consisting of —H and —($C_{1-4}$alkyl)$_{0-1}$G, wherein G is selected from the group consisting of —COOH, —H, —$PO_3$H, —$SO_3$H, —Br, —Cl, —F, —O$C_{1-4}$alkyl, —$SC_{1-4}$alkyl, aryl, —C(O)O$C_1$-$C_6$-alkyl, —C(O)$C_{1-4}$alkyl-COOH, —C(O)$C_1$-$C_4$-alkyl and —C(O)-aryl;

or N($R^8$)$R^9$ is pyrrolyl, tetrazolyl, dimethylpyrrolyl, imidazolyl, morpholino or

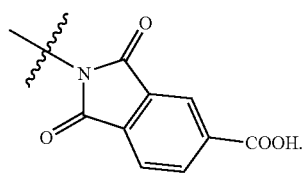

In one embodiment of Formula 14, $R^1$ is: ($CH_2$)$_x$$R^{13}$, wherein $R^{13}$ is selected from the group consisting of a hydrogen atom, $C_{1-6}$-alkyl, amino, $C_{1-6}$-alkoxy, —OH, halogen, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, furanyl, thiophenyl, thiazolyl, nitro, $C_{1-6}$-alkene, tetrazolyl, $SO_2$—$C_{1-6}$-alkyl, $SO_3$—$C_{1-6}$-alkyl, $C_{1-6}$-alkyl-urea, $C_{1-6}$-alkyl-thiourea, morpholino, piperazinyl, piperidinyl, imidazolyl and azepanyl; and x is 1, 2, 3 or 4.

In another embodiment of Formula 14, $R^{13}$ is selected from the group consisting of —COOH, imidazolyl, —$SO_3$H, —$OSO_3$H, —OH, morpholino, piperazinyl, —$PO_3$H, —$PO_3C_{1-4}$alkyl and —$NO_2$; $R^2$, $R^3$, $R^4$ and $R^5$ are each, independently, selected from the group consisting of a hydrogen atom and $NH_2$; $R^{10}$ and $R^{11}$ are each hydrogen, and x is 2, 3 or 4.

In yet another embodiment of Formula 14, $R^{13}$ is selected from the group consisting of —COOH and —COO$^-$Na$^+$; $R^2$ and $R^5$ are each, independently —$NH_2$ or —H; $R^3$, $R^4$, $R^5$, $R^{10}$ and $R^{11}$ are each a hydrogen atom; and x is 3. In still another embodiment of Formula 14, $R^1$, $R^3$, $R^4$, $R^5$, $R^{10}$ and $R^{11}$ are each a hydrogen atom; and $R^2$ and $R^5$ are each, independently —$NH_2$ or —H. In another embodiment of Formula 14, C(O)N($R^8$)$R^9$ is C(O)N(H)-t-butyl.

In another embodiment, the compound of the invention is of the general Formula 7A,

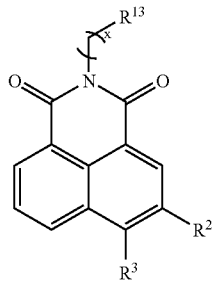

(7A)

and pharmaceutically acceptable salts, enantiomers, stereoisomers, rotamers, tautomers, diastereomers, or racemates thereof;

wherein $R^{13}$ is selected from the group consisting of $PO_3H_2$, OH, $C(O)NH_2$, $SO_3H$, COOH, $COOCH_3$, COOEt, phenyl and phenyl substituted with COOH;

$R^2$ and $R^3$ are each, independently, selected from the group consisting of C(O)Ph, CN, C(O)—N-morpholino, $C(O)NH_2$, —H, OH, $SO_3H$, $S(O)_2N(CH_3)_2$, $S(O)_2$—N-morpholino, COOH, $NO_2$, Cl and Br; and x is 1, 2, 3 or 4.

In one embodiment of Formula 7A, x is 1, 2 or 3. In another embodiment of Formula 7a, $R^2$ is —H and $R^3$ is Cl, C(O)Ph or COOH. In yet another embodiment of Formula 7a, $R^3$ is —H and $R^2$ is Cl, C(O)Ph or COOH. In still another embodiment of Formula 7a, $R^{13}$ is COOH, COOEt, OH, phenyl substituted with COOH, $SO_3H$, or phenyl. In another embodiment of Formula 7A, $R^2$ is —H and $R^3$ is CN, Br, $SO_3H$, $NO_2$ or Cl. In yet another embodiment of Formula 7A, $R^2$ is —H and $R^3$ is $SO_2N(CH_3)_2$; or $R^2$ is —H and $R^3$ is $SO_2$N-morpholino; or $R^2$ is $SO_2$N-morpholino and $R^3$ is —H; or $R^2$ is $SO_2N(CH_3)_2$ and $R^3$ is —H.

In another embodiment, the compound of the invention is of the general Formula 7B,

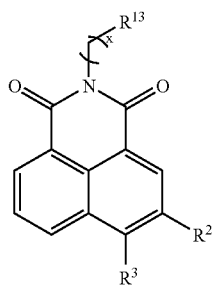

(7B)

and pharmaceutically acceptable salts, enantiomers, stereoisomers, rotamers, tautomers, diastereomers, or racemates thereof;

wherein $R^{13}$ is selected from the group consisting of phenyl, imidazolyl, morpholino, pyrrolyl, $N(H)CH_3$ and $N(CH_3)_2$;

$R^2$ and $R^3$ are each, independently, selected from the group consisting of —H, OH, $PO_3H$, $C(O)NH_2$, CN, $SO_3H$, $NO_2$, Br and C(O)morpholino; and x is 1, 2, 3 or 4.

In one embodiment, the compound of the invention is of the general Formula 10A,

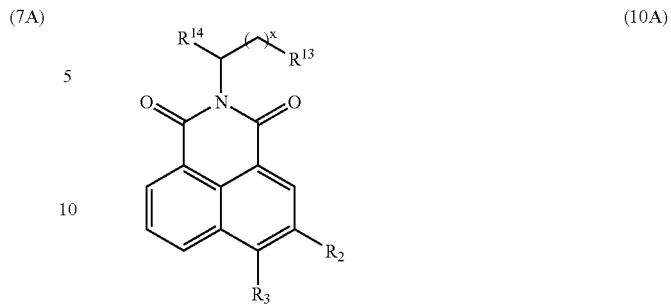

(10A)

and pharmaceutically acceptable salts, enantiomers, stereoisomers, rotamers, tautomers, diastereomers, or racemates thereof;

wherein $R^{13}$ and $R^{14}$ are each, independently, selected from the group consisting of imidazolyl, morpholino, $N(CH_3)$, $PO_3H_2$, $SO_3H$, COOH, $COOCH_3$, COOEt, phenyl and phenyl substituted with COOH;

$R^2$ and $R^3$ are each, independently, selected from the group consisting of —H, OH, CN, $SO_3H$, $S(O)_2N(CH_3)_2$, $S(O)_2$ morpholino, C(O)morpholino, $NO_2$, $C(O)NH_2$, $PO_3H$ and Br; and x is 1, 2, 3 or 4.

In one embodiment of Formula 10A, $R^{13}$ and $R^{14}$ are each, independently, selected from the group consisting of imidazolyl, morpholino, $N(CH_3)$, $PO_3H_2$, $SO_3H$, $COOCH_3$, COOEt and phenyl substituted with COOH; $R^2$ and $R^3$ are each, independently, selected from the group consisting of —H, OH, CN, $SO_3H$, $S(O)_2N(CH_3)_2$, $S(O)_2$morpholino, C(O)morpholino, $NO_2$, Br; and x is 1, 2, 3 or 4.

In another embodiment of Formula 10A, $R^{13}$ and $R^{14}$ are COOH and x is 2.

In another embodiment, the compound of the invention is of the general Formula 10B,

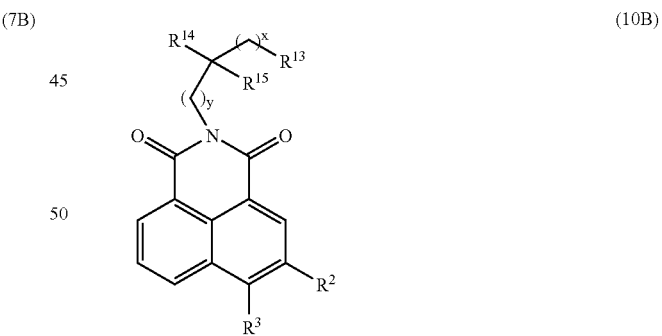

(10B)

and pharmaceutically acceptable salts, enantiomers, stereoisomers, rotamers, tautomers, diastereomers, or racemates thereof;

wherein $R^{13}$ is selected from the group consisting of a hydrogen atom, $C_{1-6}$-alkyl, amino, $C_{1-6}$-alkoxy, —OH, halogen, acid, cyano, $C_{1-6}$-alkyl-sulfonamide, aryl, heteroaryl, $C_{3-6}$-cycloalkyl, $C_{3-6}$-heterocycloalkyl, $C_{1-6}$-alkyl-amide, $C_{1-6}$-alkyl-ester, furanyl, thiophenyl, thiazolyl, nitro, $C_{1-6}$-alkene, tetrazolyl, $SO_2$—$C_{1-6}$-alkyl, $SO_3$—$C_{1-6}$-alkyl, $C_{1-6}$-alkyl-urea, $C_{1-6}$-alkyl-thiourea, morpholino, piperidinyl, piperazinyl, imidazolyl, or azepanyl;

R[14] and R[15] are each, independently, selected from the group consisting of H, $C_{1-6}$-alkyl, imidazolyl, morpholino, $N(CH_3)$, $PO_3H_2$, $SO_3H$, COOH, $COOCH_3$, COOEt, phenyl and phenyl substituted with COOH;

R[2] and R[3] are each, independently, selected from the group consisting of —H, OH, CN, $SO_3H$, $S(O)_2N(CH_3)_2$, $S(O)_2$morpholino, $NO_2$, $C(O)NH_2$, is $PO_3H$ and Br; and x and y are each, independently, 0 or 1.

In one embodiment of Formula 10B, R[13], R[14] and R[15] are each, independently, selected from the group consisting of imidazolyl, morpholino, $N(CH_3)$, $PO_3H_2$, $SO_3H$, COOH, $COOCH_3$, COOEt and phenyl substituted with COOH. In another embodiment, R[13] and R[14] are COOH and x is 2.

In another embodiment, the compound of the invention is of the general Formula 11A, (11A)

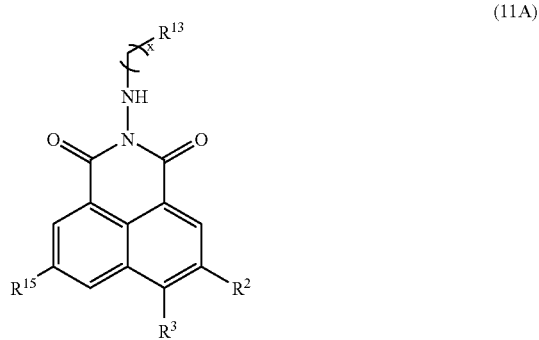

and pharmaceutically acceptable salts, enantiomers, stereoisomers, rotamers, tautomers, diastereomers, or racemates thereof;

wherein

R[13] is selected from the group consisting of $N(H)NH_2$, OH, imidazolyl, morpholino, $N(CH_3)$, $PO_3H_2$, $SO_3H$, COOH, $COOCH_3$, COOEt, phenyl and phenyl substituted with COOH;

R[2], R[3] and R[15] are each, independently, selected from the group consisting of —H, $PO_3H$, $C(O)NH_2$, CN, OH, $SO_3H$, $S(O)_2N(CH_3)_2$, $S(O)_2$morpholino, $NO_2$, Br, $NH_2$, $SO_3H$; and x is 0, 1, 2, 3 or 4.

In one embodiment of Formula 11A, x is 2, R[13] is OH, R[2] is $NO_2$, and R[3] and R[15] are —H. In another embodiment of Formula 11A, x is 0, R[13] is $C(O)N(H)NH_2$, R[2] and R[15] are, independently, $SO_3H$ or $NO_2$, and R[3] is $NH_2$.

It is to be understood that all of the compounds of Formulas 1, 3, 4, 6, 7, 11, 13, 14, 7A, 7B, 10A, 10B and 11A described above will further include double bonds and/or hydrogens between adjacent atoms as required to satisfy the valence of each atom. That is, double bonds and or hydrogens are added to provide the following number of total bonds to each of the following types of atoms: carbon: four bonds; nitrogen: three bonds; oxygen: two bonds; and sulfur: two-six bonds.

In a particular embodiment of the invention, the NGF/NTR modulator of Formulas 1, 3, 4, 6, 7, 11, 13, 14, 7A, 7B, 10A, 10B and 11A are any one of the compounds of Table 1 or derivatives and fragments thereof, including salts thereof, e.g., pharmaceutically acceptable salts.

In another embodiment, the invention pertains to the NGF/NTR modulators of Formulas 1, 3, 4, 6, 7, 11, 13, 14, 7A, 7B, 10A, 10B and 11A, including salts thereof, e.g., pharmaceutically acceptable salts. Particular embodiments of the invention pertain to the modulating compounds of Table 1 or derivatives thereof, including salts thereof, e.g., pharmaceutically acceptable salts.

In yet another embodiment, the invention pertains to pharmaceutical compositions comprising NT/NTR modulating compounds described herein and a pharmaceutical acceptable carrier.

In another embodiment, the invention includes any novel compound or pharmaceutical compositions containing compounds of the invention described herein. For example, compounds and pharmaceutical compositions containing compounds set forth herein (e.g., Table 1) are part of this invention, including salts thereof, e.g., pharmaceutically acceptable salts.

The method for acquiring the PC12 data described in Table 1 is described herein in Example 1. Each experiment was done at least once with an n value of 4 for each data point. (n/a=not acquired)

TABLE 1

| Compound Name | Structure | PC12 (TrkA & p75) Single point (% max binding) Concentration (μM) | Mean | Abfix IC50 Mean |
|---|---|---|---|---|
| 4-(5-Amino-1,3-dioxo-1H,3H-benzo[de]isoquinolin-2-yl)-butyric acid (1) | [structure] | n/a | n/a | *** |

TABLE 1-continued

| Compound Name | Structure | PC12 (TrkA & p75) Single point (% max binding) Concentration (μM) | Mean | Abfix IC50 Mean |
|---|---|---|---|---|
| Sodium 4-(5-amino-1,3-dioxo-1H,3H-benzo[de]isoquinolin-2-yl)-butyrate (2) | 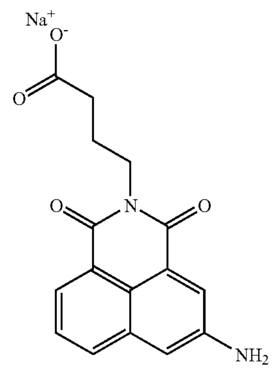 | n/a | n/a | n/a |
| 4-(5,8-Diamino-1,3-dioxo-1H,3H-benzo[de]isoquinolin-2-yl)-butyric acid (9) | 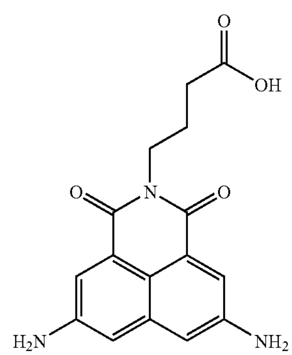 | n/a | n/a | *** |
| 4-(5,8-Dinitro-1,3-dioxo-1H,3H-benzo[de]isoquinolin-2-yl)-butyric acid (10) | 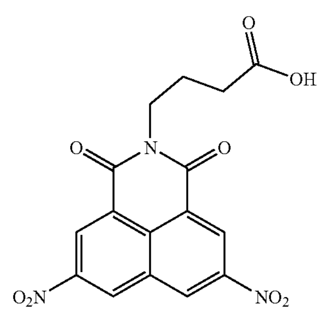 | n/a | n/a | *** |
| 4-(5,8-Bis-acetylamino-1,3-dioxo-1H,3H-benzo[de]isoquinolin-2-yl)-butyric acid (11) | 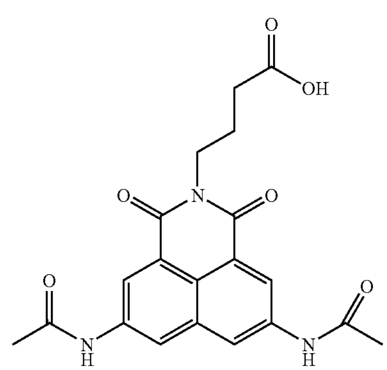 | n/a | n/a | *** |

TABLE 1-continued

| Compound Name | Structure | PC12 (TrkA & p75) Single point (% max binding) Concentration (μM) | Mean | Abfix IC50 Mean |
|---|---|---|---|---|
| 4-(5-Acetylamino-1,3-dioxo-1H,3H-benzo[de]isoquinolin-2-yl)-butyric acid (13) | 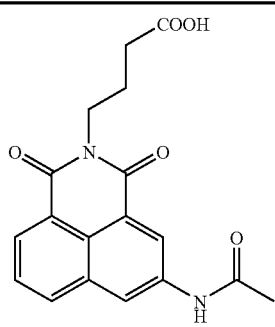 | n/a | n/a | n/a |
| 2,3-Dihydro-benzo[de]iso-quinolin-1-one (31) | 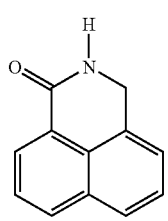 | n/a | n/a | n/a |
| 5-Nitro-2-(3-pyrrol-1-yl-propyl)-benzo[de]isoquinoline-1,3-dione (34) | 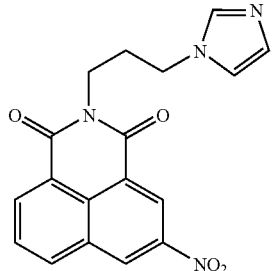 | n/a | n/a | n/a |
| 2-(3-Methylamino-propyl)-5-nitro-benzo[de]isoquinoline-1,3-dione (39) | 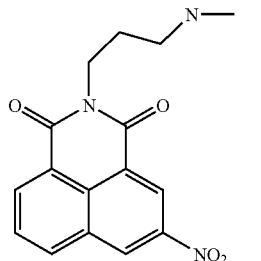 | n/a | n/a | n/a |
| 2-(5-Nitro-1,3-dioxo-1H,3H-benzo[de]isoquinolin-2-yl)-pentanedioic acid (43) | 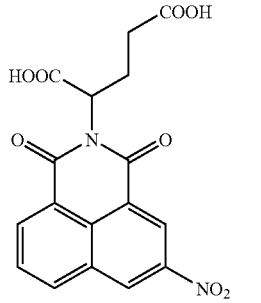 | n/a | n/a | * |

TABLE 1-continued

| Compound Name | Structure | PC12 (TrkA & p75) Single point (% max binding) Concentration (μM) | Mean | Abfix IC50 Mean |
|---|---|---|---|---|
| 2-Benzyl-5-nitro-benzo[de]isoquinoline-1,3-dione (44) | | n/a | n/a | n/a |
| 6-Amino-1,3-dioxo-2-amino-ureido-2,3-dihydro-1H-benzo[de]isoquinoline-5,8-disulfonic acid- di-potassium salt (52) | | 50 | * | n/a |
| Sodium 4-(5-nitro-1,3-dioxo-1H,3H-benzo[de]isoquinolin-2-yl)-butyrate (62) | | n/a | n/a | n/a |
| 4-(5-Nitro-1,3-dioxo-1H,3H-benzo[de]isoquinolin-2-yl)-butyric acid (63) | | n/a | n/a | n/a |

TABLE 1-continued

| Compound Name | Structure | PC12 (TrkA & p75) | | Abfix |
| --- | --- | --- | --- | --- |
| | | Single point (% max binding) | | |
| | | Concentration (μM) | Mean | IC50 Mean |
| 4-(1,3-Dioxo-1H,3H-benzo[de]isoquinolin-2-yl)-butyric acid (69) | | n/a | n/a | n/a |
| 2-(3-Hydroxy-propyl)-5-nitro-benzo[de]isoquinoline-1,3-dione (72) | | n/a | n/a | n/a |
| 4-(6-Bromo-1,3-dioxo-1H,3H-benzo[de]isoquinolin-2-yl)-butyric acid (73) | | n/a | n/a | n/a |
| 4-[4-(5-Nitro-1,3-dioxo-1H,3H-benzo[de]isoquinolin-2-yl)-phenyl]-butyric acid ethyl ester (76) | | n/a | n/a | n/a |

TABLE 1-continued

| Compound Name | Structure | PC12 (TrkA & p75) Single point (% max binding) | | Abfix |
|---|---|---|---|---|
| | | Concentration (µM) | Mean | IC50 Mean |
| 4-(1,3-Dioxo-6-sulfo-1H,3H-benzo[de]isoquinolin-2-yl)-butyric acid (77) | 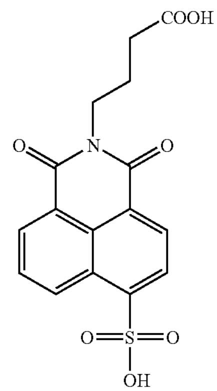 | n/a | n/a | n/a |
| 4-(6-Nitro-1,3-dioxo-1H,3H-benzo[de]isoquinolin-2-ylmethyl)-benzoic acid (79) | 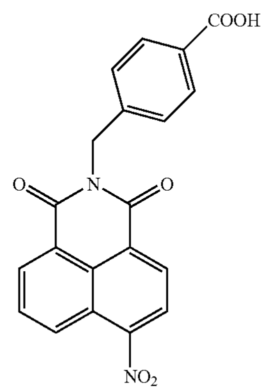 | n/a | n/a | * |
| 3-(5-Nitro-1,3-dioxo-1H,3H-benzo[de]isoquinolin-2-yl)-propane-1-sulfonic acid (83) | 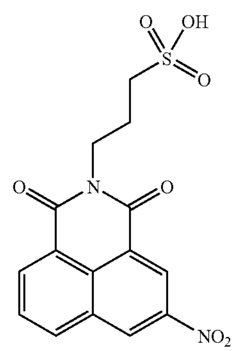 | n/a | n/a | ** |
| 4-(5-Nitro-1,3-dioxo-1H,3H-benzo[de]isoquinolin-2-ylmethyl)-benzoic acid (85) | 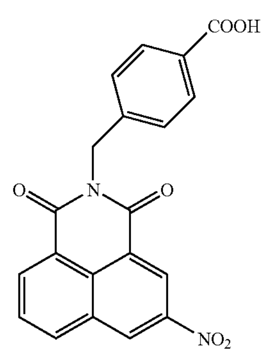 | n/a | n/a | n/a |

TABLE 1-continued

| | | PC12 (TrkA & p75) | | |
| | | Single point (% max binding) | | Abfix |
| Compound Name | Structure | Concentration (μM) | Mean | IC50 Mean |
|---|---|---|---|---|
| 4-(6-Nitro-1,3-dioxo-1H,3H-benzo[de]isoquinolin-2-yl)-butyric acid (86) | | n/a | n/a | n/a |
| [3-(5-Nitro-1,3-dioxo-1H,3H-benzo[de]isoquinolin-2-yl)-propyl]-phosphonic acid (87) | | n/a | n/a | * |
| 4-(5-Bromo-8-nitro-1,3-dioxo-1H,3H-benzo[de]isoquinolin-2-yl)-butyric acid (89) | | 50 | ** | * |
| 2-(3-Morpholin-4-yl-propyl)-5-nitro-benzo[de]isoquinoline-1,3-dione (94) | | n/a | n/a | n/a |

TABLE 1-continued

| Compound Name | Structure | PC12 (TrkA & p75) | | |
|---|---|---|---|---|
| | | Single point (% max binding) | | Abfix |
| | | Concentration (μM) | Mean | IC50 Mean |
| 4-(5-Carbamoyl-1,3-dioxo-1H,3H-benzo[de]isoquinolin-2-yl)-butyric acid (95) | | n/a | n/a | n/a |
| 4-(5-Acetylamino-1,3-dioxo-1H,3H-benzo[de]isoquinolin-2-yl)-butyric acid (96) | | n/a | n/a | *** |
| 2-(2-Hydroxy-ethylamino)-5-nitro-benzo[de]isoquinoline-1,3-dione (97) | | n/a | n/a | * |
| 4-(5-Nitro-1,3-dioxo-1H,3H-benzo[de]isoquinolin-2-ylmethyl)-benzoic acid (98) | | n/a | n/a | n/a |

TABLE 1-continued

| Compound Name | Structure | PC12 (TrkA & p75) Single point (% max binding) Concentration (μM) | Mean | Abfix IC50 Mean |
|---|---|---|---|---|
| 4-(6-Benzoyl-1,3-dioxo-1H,3H-benzo[de]isoquinolin-2-yl)-butyric acid (99) | 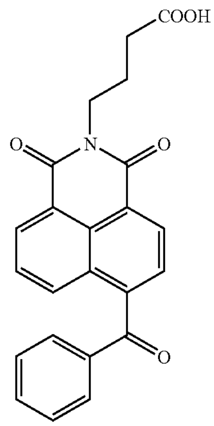 | 25 | * |  |
| 2-(3-Carboxy-propyl)-1,3-dioxo-2,3-dihydro-1H-benzo[de]isoquinoline-6-carboxylic acid (100) | 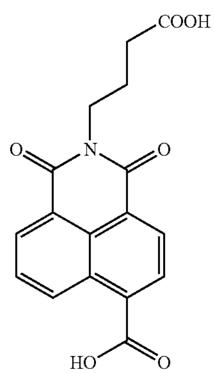 | 25 | * |  |
| 4-(6,7-Dinitro-1,3-dioxo-1H,3H-benzo[de]isoquinolin-2-yl)-butyric acid (101) | 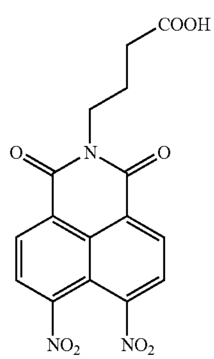 | n/a | n/a | *** |

TABLE 1-continued

| Compound Name | Structure | PC12 (TrkA & p75) Single point (% max binding) | | Abfix |
|---|---|---|---|---|
| | | Concentration (μM) | Mean | IC50 Mean |
| 4-(6,7-Diamino-1,3-dioxo-1H,3H-benzo[de]isoquinolin-2-yl)-butyric acid (102) | | n/a | n/a | /* |
| 6-Nitro-1H-benzo[cd]indol-2-one (103) | | 25 | * | n/a |
| 4-(6-Chloro-1,3-dioxo-1H,3H-benzo[de]isoquinolin-2-yl)-butyric acid (104) | | 25 | ** | *** |
| 3-(5,8-Dinitro-1,3-dioxo-1H,3H-benzo[de]isoquinolin-2-yl)-propane-1-sulfonic acid (105) | | n/a | n/a | n/a |

TABLE 1-continued

| Compound Name | Structure | PC12 (TrkA & p75) | | |
|---|---|---|---|---|
| | | Single point (% max binding) | | Abfix |
| | | Concentration (μM) | Mean | IC50 Mean |
| 3-(5,8-Diamino-1,3-dioxo-1H,3H-benzo[de]isoquinolin-2-yl)-propane-1-sulfonic acid (106) | | n/a | n/a | *** |
| 3-(5,8-Bis-acetylamino-1,3-dioxo-1H,3H-benzo[de]isoquinolin-2-yl)-propane-1-sulfonic acid (107) | | n/a | n/a | *** |
| 4-(5,8-Bis-acetylamino-1,3-dioxo-1H,3H-benzo[de]isoquinolin-2-yl)-butyric acid ethyl ester (108) | | n/a | n/a | * |
| 4-[5,8-Bis-(3,3-dimethyl-butyrylamino)-1,3-dioxo-1H,3H-benzo[de]isoquinolin-2-yl]-butyric acid (109) | | n/a | n/a | * |

TABLE 1-continued

| Compound Name | Structure | PC12 (TrkA & p75) | | |
|---|---|---|---|---|
| | | Single point (% max binding) | | Abfix |
| | | Concentration (μM) | Mean | IC50 Mean |
| 4-(5,8-Dinitro-1,3-dioxo-1H,3H-benzo[de]isoquinolin-2-yl)-butyric acid ethyl ester (110) | 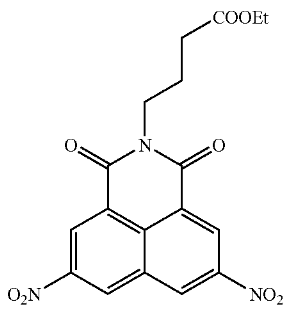 | n/a | n/a | * |
| 4-(5,8-Diamino-1,3-dioxo-1H,3H-benzo[de]isoquinolin-2-yl)-butyric acid ethyl ester (111) | 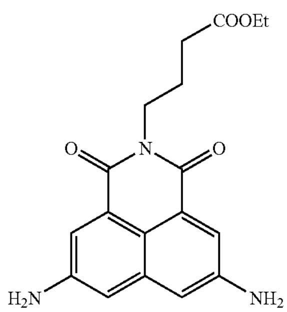 | n/a | n/a | * |
| 4-(6-Dimethylsulfamoyl-1,3-dioxo-1H,3H-benzo[de]isoquinolin-2-yl)-butyric acid (112) | 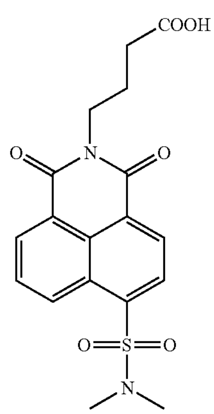 | 50 | * | * |

TABLE 1-continued

| Compound Name | Structure | PC12 (TrkA & p75) | | Abfix |
| --- | --- | --- | --- | --- |
| | | Single point (% max binding) | | |
| | | Concentration (μM) | Mean | IC50 Mean |
| 4-[6-(Morpholine-4-sulfonyl)-1,3-dioxo-1H,3H-benzo[de]isoquinolin-2-yl]-butyric acid (113) | | 50 | ** | * |
| 4-(5-Dimethylsulfamoyl-1,3-dioxo-1H,3H-benzo[de]isoquinolin-2-yl)-butyric acid (114) | | 50 | ** | * |
| 4-[5-(Morpholine-4-sulfonyl)-1,3-dioxo-1H,3H-benzo[de]isoquinolin-2-yl]-butyric acid (115) | | n/a | n/a | n/a |

TABLE 1-continued

| Compound Name | Structure | PC12 (TrkA & p75) | | Abfix |
| --- | --- | --- | --- | --- |
| | | Single point (% max binding) | | |
| | | Concentration (μM) | Mean | IC50 Mean |
| [3-(5,8-Dinitro-1,3-dioxo-1H,3H-benzo[de]isoquinolin-2-yl)-propyl]-phosphonic acid (116) | 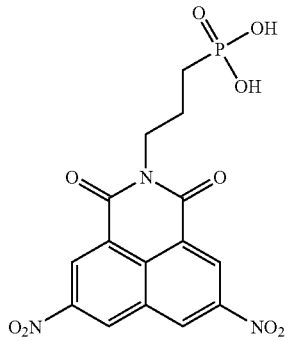 | n/a | n/a | n/a |
| [3-(5,8-Diamino-1,3-dioxo-1H,3H-benzo[de]isoquinolin-2-yl)-propyl]-phosphonic acid (117) | 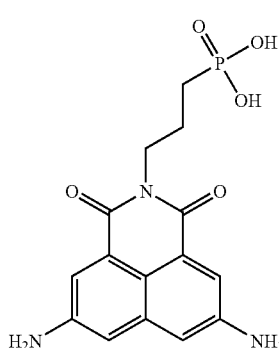 | n/a | n/a | n/a |
| [3-(5,8-Bis-acetylamino-1,3-dioxo-1H,3H-benzo[de]isoquinolin-2-yl)-propyl]-phosphonic acid (118) | 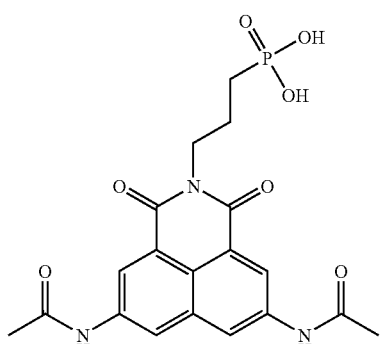 | n/s | n/a | *** |
| 3-(5,8-Dinitro-1,3-dioxo-1H,3H-benzo[de]isoquinolin-2-yl)-propionic acid (119) | 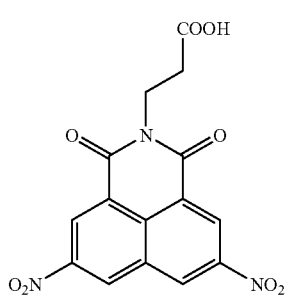 | n/a | n/a | n/a |

TABLE 1-continued

| Compound Name | Structure | PC12 (TrkA & p75) Single point (% max binding) Concentration (μM) | Mean | Abfix IC50 Mean |
|---|---|---|---|---|
| 3-(5,8-Diamino-1,3-dioxo-1H,3H-benzo[de]isoquinolin-2-yl)-propionic acid (120) | | n/a | n/a | n/a |
| 3-(5,8-Bis-acetylamino-1,3-dioxo-1H,3H-benzo[de]isoquinolin-2-yl)-propionic acid (121) | | n/a | n/a | *** |
| 4-(1,3-Dioxo-5-pyrrol-1-yl-1H,3H-benzo[de]isoquinolin-2-yl)-butyric acid (122) | | n/a | n/a | ** |
| 4-[6-(Morpholine-4-carbonyl)-1,3-dioxo-1H,3H-benzo[de]isoquinolin-2-yl]-butyric acid (123) | | n/a | n/a | * |

TABLE 1-continued

| Compound Name | Structure | PC12 (TrkA & p75) Single point (% max binding) Concentration (µM) | Mean | Abfix IC50 Mean |
|---|---|---|---|---|
| 4-(5-Cyano-1,3-dioxo-1H,3H-benzo[de]isoquinolin-2-yl)-butyric acid (124) | | n/a | n/a | *** |
| 4-[5-(2,5-Dimethyl-pyrrol-1-yl)-1,3-dioxo-1H,3H-benzo[de]isoquinolin-2-yl]-butyric acid (125) | | n/a | n/a | * |
| 3-(5-Cyano-1,3-dioxo-1H,3H-benzo[de]isoquinolin-2-yl)-propionic acid (126) | | n/a | n/a | n/a |
| 2-(3-Carboxy-propyl)-1,3-dioxo-2,3-dihydro-1H-benzo[de]isoquinoline-5-carboxylic acid (128) | | n/a | n/a | n/a |

TABLE 1-continued

| Compound Name | Structure | PC12 (TrkA & p75) Single point (% max binding) | | Abfix |
|---|---|---|---|---|
| | | Concentration (µM) | Mean | IC50 Mean |
| 4-(6-Cyano-1,3-dioxo-1H,3H-benzo[de]isoquinolin-2-yl)-butyric acid (129) | [structure] | n/a | n/a | ** | max binding Key
* < *** <30
30 < ** <50
* >50
IC$_{50}$ Key
0 < *** <10
10 < ** <20
* >20

In a particularly preferred embodiment, the compound of the invention is 4-(5,8-Bis-acetylamino-1,3-dioxo-1H,3H-benzo[de]isoquinolin-2-yl)-butyric acid (Compound 11).

In one embodiment of the invention, 4-(5,8-Bis-acetylamino-1,3-dioxo-1H,3H-benzo[de]isoquinolin-2-yl)-butyric acid (Compound 11) is used to treat pain in a subject.

In another embodiment of the invention, 4-(5,8-Bis-acetylamino-1,3-dioxo-1H, 3H-benzo[de]isoquinolin-2-yl)-butyric acid (Compound 11) is used to treat inflammation in a subject.

In one embodiment of the invention, the modulating compounds of the invention are capable of chemically interacting with NGF, p75$^{NTR}$, and/or TrkA. The language "chemical interaction" is intended to include, but is not limited to, reversible interactions such as hydrophobic/hydrophilic, ionic (e.g., coulombic attraction/repulsion, ion-dipole, charge-transfer), covalent bonding, Van der Waals, and hydrogen bonding. In certain embodiments, the chemical interaction is a reversible Michael addition. In a specific embodiment, the Michael addition involves, at least in part, the formation of a covalent bond.

Compounds of the invention can be synthesized according to standard organic synthesis procedures that are known in the art. Synthesis procedures for compounds of the invention are described herein in the Exemplification section. Additionally, compounds similar to the compounds of the invention can be found in U.S. Pat. No. 6,492,380, U.S. Pat. No. 6,468,990, and U.S. patent application Ser. No. 09/758,917, each of which are incorporated herein by reference.

Acid addition salts of the compounds of the invention are most suitably formed from pharmaceutically acceptable acids, and include for example those formed with inorganic acids, e.g., hydrochloric, sulphuric or phosphoric acids and organic acids e.g. succinic, maleic, acetic or fumaric acid. Other non-pharmaceutically acceptable salts, e.g., oxalates, may be used for example in the isolation of the invention, and the compounds of Table 1 for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base, e.g., sodium carbonate or potassium hydroxide, to liberate the free base which is then extracted into an appropriate solvent, such as ether. The free base is then separated from the aqueous portion, dried, and treated with the requisite acid to give the desired salt. Particularly preferred salts are sodium, lysine and argentine salts of the compounds of the invention.

In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention, and the compounds of Table 1 having a free carboxy group may be esterified using standard conditions which may include activation followed by treatment with the desired alcohol in the presence of a suitable base.

Assays

The present invention also relates to a method of modulating the interaction of NGF (or proNGF) with a neurotrophin receptor, e.g., p75$^{NTR}$ and/or TrkA. In certain embodiments, the method comprises contacting NGF and/or a precursor thereof (proNGF) in the presence of p75$^{NTR}$ and/or TrkA with a NGF/NTR modulating amount of a NGF/NTR modulator compound (i.e., a compound of the invention), thereby modulating the interaction of NGF (and/or proNGF) with p75$^{NTR}$ and/or TrkA.

The methods of the invention can be practiced in vitro, for example, in a cell culture screening assay to screen compounds which potentially modulate, directly or indirectly, receptor function. In such a method, the modulating compound can function by interacting with and eliminating any function or activity (e.g., receptor binding) of NGF and/or a precursor thereof in the sample or culture. The modulating compounds can also be used to control NGF activity in neuronal cell culture. In vitro cross-linking assays for determining the ability of a compound within the scope of the invention to modulate the interaction of NGF with p75$^{NTR}$ and/or TrkA, are well known in the art and described in the examples herein. Cross-linking data for compounds similar to the compounds of the invention can be found in U.S. Pat. No. 6,492,380, U.S. Pat. No. 6,468,990, and U.S. patent application Ser. No. 09/758,917, each of which are incorporated herein by reference. Other assays for determining the ability of a compound to modulate the activity of NGF with its respective receptors are also readily available to the skilled artisan (see, Barker et al, Neuron 13(1): 203-215; (1994), Dehant et al., Development 119: 545-558 (1993); and US 2002/016982).

Recombinant and native neurotrophin polypeptides from different species, including humans, are commercially available from several sources (e.g., Promega Corporation and R&D Systems). In addition, neurotrophin polypeptides for use in the assays described herein can be readily produced by standard biological techniques or by chemical synthesis. For example, a host cell transfected with an expression vector containing a nucleotide sequence encoding the desired neurotrophin can be cultured under appropriate conditions to allow expression of the peptide to occur. The secreted peptide can then be isolated according to standard techniques. Coding polynucleotides, precursors and promoters for a number of neurotrophins are known, including coding sequences for neurotrophins of some mammalian species. For example, GenBank M61176 sets for the coding sequence for BDNF (see also, XM.006027); BDNF precursor is set forth at BF439589; and a BDNF specific promoter is set forth at Eo5933. A similar range of coding sequences for other neurotrophins, including proNGF and mature NGF (e.g., NCBI ACCESSION NO P01138 and CAA37703), NT-4/5 and NT-3, are also available through GenBank and other publicly accessible nucleotide and amino acid sequence databases. Alternatively, the neurotrophin, e.g., NGF can be obtained by culturing a primary cell culture or an established cell line that can produce the neurotrophin, and isolating from the culture broth thereof (e.g., culture supernatant, cultured cells).

The method can also be practiced in vivo, for example, to modulate one or more processes mediated by the interaction of NGF (and/or proNGF) with p75$^{NTR}$, and/or the interaction of NGF with TrkA. Animal models for determining the ability of a compound of the invention to treat a disorder associated with or caused by a neurotrophin-mediated biological activity (e.g., pain, inflammatory disorders, respiratory disorders, neurological disorders, genitourinary disorders and gastrointestinal disorders) are well known and readily available to the skilled artisan.

For example, animal models of neuropathic pain based on injury inflicted to a nerve (mostly the sciatic nerve) are described in Zeltser et al., 2000, Pain 89:19-24; Bennett et al., 1988, Pain 33:87-107; Seltzer et al., 1990, Pain 43:205-218; Kim et al., 1992, Pain 50:355-363; Decosterd et al., 2000, Pain 87:149-158 and DeLeo et al., 1994, Pain 56:9-16. There are also models of diabetic neuropathy (STZ induced diabetic neuropathy—Courteix et al., 1994, Pain 57:153-160) and drug induced neuropathies (vincristine induced neuropathy—Aley et al., 1996, Neuroscience 73: 259-265; oncology-related immunotherapy, anti-GD2 antibodies—Slart et al., 1997, Pain 60:119-125). Acute pain in humans can be reproduced using in murine animals chemical stimulation: Martinez et al., Pain 81: 179-186; 1999 (the writhing test—intraperitoneal acetic acid in mice), Coderre et al., Pain. 1993, 54:43-50 (intraplantar injection of formalin). Other types of acute pain models are described in Whiteside et al., 2004, Br J Pharmacol 141:85-91 (the incisional model, a post-surgery model of pain) and Johanek and Simone, 2004, Pain 109:432-442 (a heat injury model). An animal model of inflammatory pain using complete Freund's adjuvant (intraplantar injection) is described in Jasmin et al., 1998, Pain 75: 367-382. Intracapsular injection of irritant agents (complete Freund's adjuvant, iodoacetate, capsaicine, urate crystals, etc.) is used to develop arthritis models in animals (Fernihough et al., 2004, Pain 112:83-93; Coderre and Wall, 1987, Pain 28:379-393; Otsuki et al., 1986, Brain Res. 365:235-240). A stress-induced hyperalgesia model is described in Quintero et al., 2000, Pharmacology, Biochemistry and Behavior 67:449-458. Further animal models for pain are considered in an article of Walker et al. 1999 Molecular Medicine Today 5:319-321, comparing models for different types of pain, which are acute pain, chronic/inflammatory pain and chronic/neuropathic pain, on the basis of behavioral signs. Animal models for depression are described by E. Tatarczynska et al., Br. J. Pharmacol. 132(7): 1423-1430 (2001) and P. J. M. Will et al., Trends in Pharmacological Sciences 22(7):331-37 (2001)); models for anxiety are described by D. Treit, "Animal Models for the Study of Anti-anxiety Agents: A Review," Neuroscience & Biobehavioral Reviews 9(2):203-222 (1985). Additional animal models for pain are also described herein in the Exemplification section.

Genitourinary models include methods for reducing the bladder capacity of test animals by infusing either protamine sulfate and potassium chloride (See, Chuang, Y. C. et al., Urology 61(3): 664-670, 2003) into the bladder. These methods also include the use of a well accepted model of for urinary tract disorders involving the bladder using intravesically administered acetic acid as described in Sasaki et al. (2002) J. Urol. 168: 1259-64. Efficacy for treating spinal cord injured patients can be tested using methods as described in Yoshiyama et al. (1999) Urology 54: 929-33.

Gastrointestinal models can be found in: Gawad, K. A., et al., Ambulatory long-term pH monitoring in pigs, Surg Endosc, (2003); Johnson, S. E. et al., Esophageal Acid Clearance Test in Healthy Dogs, Can. J. Vet. Res. 53(2): 244-7 (1989); and Cicente, Y. et al., Esophageal Acid Clearance: More Volume-dependent Than Motility Dependent in Healthy Piglets, J. Pediatr. Gastroenterol. Nutr. 35(2): 173-9 (2002). Models for a variety of assays can be used to assess visceromotor and pain responses to rectal distension. See, for example, Gunter et al, Physiol. Behav., 69(3): 379-82 (2000), Depoortere et al, J. Pharmacol. and Exp. Ther., 294(3): 983-990 (2000), Morteau et al, Fund. Clin. Pharmacol., 8(6): 553-62 (1994), Gibson et al, Gastroenterology (Suppl. 1), 120(5): A19-A20 (2001) and Gschossmann et al, Eur. J. Gastro. Hepat., 14(10): 1067-72 (2002) the entire contents of which are each incorporated herein by reference.

Gastrointestinal motility can be assessed based on either the in vivo recording of mechanical or electrical events associated intestinal muscle contractions in whole animals or the activity of isolated gastrointestinal intestinal muscle preparations recorded in vitro in organ baths (see, for example, Yaun et al, Br. J. Pharmacol., 112(4):1095-1100 (1994), Jin et al., J.

Pharm. Exp. Ther., 288(1): 93-97 (1999) and Venkova et al, J. Pharm. Exp. Ther., 300(3): 1046-1052 (2002)). Tatersall et al and Bountra et al, European Journal of Pharmacology, 250: (1993) R5 and 249:(1993) R3-R4 and Milano et al, J. Pharmacol. Exp. Ther., 274(2): 951-961 (1995).

Animal models for investigating neurological disorders include, but are not limited to, those described in Morris et al, (Learn. Motiv. 1981; 12: 239-60) and Abeliovitch et al., Cell 1993; 75: 1263-71). For example, neurological models for studying spinal cord injury, are described in Yoshiyama, M. et al., Urology 54(5): 929-933 (1999).

Further examples of animal models for pain and inflammation include, but are not limited to the models listed in Table 2.

TABLE 2

| Model Name | Modality tested | Brief Description | Non-limiting examples of potential clinical indications (Reference) |
|---|---|---|---|
| ACUTE PHASIC PAIN | | | |
| Tail-flick | Thermal | Tip of tail of rats is immersed if hot water and time to withdrawal from water is measured. Alternatively, a radiant heat source is applied to the tail and time to withdrawal is determined. Analgesic effect is evidenced by a prolongation of the latency period | Acute nociceptive pain (Hardy et al. Am J Physiol 1957; 189: 1-5.; Ben-Bassat et al. Arch Intern Pharmacodyn Ther 1959; 122: 434-47.) |
| hot-plate | Thermal | Rats walk over a heated surface with increasing temperature and observed for specific nociceptive behavior such paw licking, jumping. Time to appearance of such behavior is measured. Analgesic effects are evidenced by a prolonged latency. | Acute nociceptive pain (Woolfe et al. J Pharmacol Exp Ther 1944; 80: 300-7.) |
| Hargreaves Test | Thermal | A focused beam of light is projected onto a small surface of the hind leg of a rat with increasing temperature. Time to withdrawal is measured. Analgesic effect translates into a prolonged latency | Acute nociceptive pain (Yeomans et al. Pain 1994; 59: 85-94.) |
| Pin Test or Randall Selitto | Mechanical | An increasing calibrated pressure is applied to the paw of rats with a blunt pin. Pressure intensity is measured. Alternatively increased pressure is applied to the paw using a caliper until pain threshold is reached and animals withdraw the paw. | Acute nociceptive pain (Green et al. Br J Pharmacol 1951; 6: 572-85.; Randall et al. Arch Int Pharmacodyn Ther 1957; 111: 409-19) |
| HYPERALGESIA MODELS/CHRONIC INFLAMMATORY PAIN MODELS | | | |
| Hargreaves or Randal & Selitto | Thermal and/or mechanical | A sensitizing agent (e.g, complete Freund's adjuvant (CFA), carrageenin, turpentine etc.) is injected into the paw of rats creating a local inflammation and sensitivities to mechanical (Randall & Selitto) and/or therma (Hargreaves)l stimulation are measured with comparison to the contralateral non-sensitized paw | Chronic pain associated with tissue inflammation, e.g. post-surgical pain, (Hargreaves et al. Pain 1988; 32: 77-88.) Randall LO, Selitto JJ. Arch Int Pharmacodyn 1957; 3: 409-19. |
| Yeomans model | Thermal | Rat hind paw in injected with capsaicin, a sensitizing agent for small C-fibers or DMSO, a sensitizing agent for A-delta fibers. A radiant heat is applied with different gradient to differentially stimulate C-fibers or A-delta fibers and discriminate between the effects mediated by both pathways | Chronic pain associated with tissue inflammation, e.g. post-surgical pain (Yeomans et al. Pain 1994; 59: 85-94.; Otsuki et al. Brain Res 1986; 365: 235-240.) |
| CHRONIC MALIGNANT PAIN (CANCER PAIN) | | | |
| Bone Cancer Model | Thermal and/or mechanical | In this model, osteolytic mouse sarcoma NCTC2472 cells are used to induce bone cancer by injecting tumor cells into the marrow space of the femur bone and sealing the injection site | Bone cancer pain (Schwei et al., J. Neurosci. 1999; 19: 10886-10897.) |
| Cancer invasion pain model (CIP) | Thermal and/or mechanical | Meth A sarcoma cells are implanted around the sciatic nerve in BALB/c mice and these animals develop signs of allodynia and thermal hyperalgesia as the tumor grows, compressing the nerve. Spontaneous pain (paw lifting) is also visible. | Malignant neuropathic pain (Shimoyama et al., Pain 2002; 99: 167-174.) |
| CHRONIC NON-MALIGNANT PAIN | | | |
| Muscle Pain | Thermal and/or mechanical | Repeated injections of acidic saline into one gastrocnemius muscle produces bilateral, long-lasting mechanical hypersensitivity of the paw (i.e. hyperalgesia) without associated tissue damage | Fibromyalgia (Sluka et al. Pain 2003; 106: 229-239.) |
| UV-irradiation | Thermal and/or mechanical | Exposure of the rat hind paw to UV irradiation produces highly reliable and persistent allodynia. Various irradiation periods with UV-B produce skin inflammation with different time courses | Inflammatory pain associated with first- and second-degree burns. (Perkins et al. Pain 1993; 53: 191-197.) |
| CHRONIC NEUROPATHIC PAIN | | | |
| Chronic Constriction Injury (CCI) or | Mostly mechanical but aso | Loose chronic ligature of the sciatic nerve. Thermal or mechanical sensitivities are tested using Von Frey hairs or the paw withdrawal test (Hargreaves) | Clinical Neuropathic pain: nerve compression and direct mechanical neuronal damage might be relevant |

TABLE 2-continued

| Model Name | Modality tested | Brief Description | Non-limiting examples of potential clinical indications (Reference) |
|---|---|---|---|
| Bennett and Xie model | thermal | | clinical comparisons (Bennett & Xie, Neuropharmacology 1984; 23: 1415-1418.) |
| Chung's model or Spinal Nerve Ligation model (SNL) | Mostly mechanical but also thermal | Tight ligation of one of the two spinal nerves of the sciatic nerve. Thermal or mechanical sensitivities are tested using Von Frey hairs or the paw withdrawal test (Hargreaves) | Same as above: root compression might be a relevant clinical comparison (Kim and Chung, Pain 1990; 41: 235-251.) |

Accordingly, an agent identified as described herein (e.g., an NGF/NTR modulator) can be used in an animal model to determine the efficacy, toxicity, or side effects of treatment with such an agent.

Accordingly, this invention pertains to uses of novel agents identified by the above-described screening assays for treatments as described herein Pharmaceutical Compositions The present invention also provides pharmaceutical compositions. Such compositions comprise a therapeutically (or prophylactically) effective amount of a NGF/NTR modulator, and preferably one or more compounds of the invention described above, and a pharmaceutically acceptable carrier or excipient. Suitable pharmaceutically acceptable carriers include, but are not limited to, saline, buffered saline, dextrose, water, glycerol, ethanol, and combinations thereof. The carrier and composition can be sterile. The formulation should suit the mode of administration.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, cyclodextrin, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as trilycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The pharmaceutical compositions of the invention can also include an agent which controls release of the compound of the invention, thereby providing a timed or sustained release composition.

The present invention also relates to prodrugs of the compounds disclosed herein, as well as pharmaceutical compositions comprising such prodrugs. For example, compounds of the invention which include acid functional groups or hydroxyl groups can also be prepared and administered as a corresponding ester with a suitable alcohol or acid. The ester can then be cleaved by endogenous enzymes within the subject to produce the active agent.

Formulations of the present invention include those suitable for oral, nasal, topical, transmucosal, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of Administration

The invention provides a method of treating a condition mediated by an NGF/NTR interaction in a subject, including, but not limited to, pain, inflammatory disorders, respiratory disorders, neurological disorders, gastrointestinal disorders and genitourinary disorders. The method comprises the step of administering to the subject a therapeutically effective amount of a NGF/NTR modulator. The condition to be treated can be any condition which is mediated, at least in part, by the interaction of a neurotrophin (e.g. NGF) with a neurotrophin receptor (e.g., $p75^{NTR}$ and TrkA).

The quantity of a given compound to be administered will be determined on an individual basis and will be determined, at least in part, by consideration of the individual's size, the severity of symptoms to be treated and the result sought. The NGF/NTR modulators described herein can be administered alone or in a pharmaceutical composition comprising the modulator, an acceptable carrier or diluent and, optionally, one or more additional drugs.

These compounds may be administered to humans and other animals for therapy by any suitable route of administration. The NGF/NTR modulator can be administered subcutaneously, intravenously, parenterally, intraperitoneally, intradermally, intramuscularly, topically, enterally (e.g., orally), rectally, nasally, buccally, sublingually, systemically, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal mucosa, intestinal mucosa, bronchial mucosa) administration, nose drops, aerosols, inhalants, nebulizers, eye drops or suppositories can be used. The compounds and agents of this invention can be administered together with other biologically active agents, such as analgesics, e.g., opiates, anti-inflammatory agents, e.g., NSAIDs, anesthetics and other agents which can control one or more symptoms or causes of an NTR-mediated condition.

In a specific embodiment, it may be desirable to administer the agents of the invention locally to a localized area in need of treatment; this may be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints or the urinary bladder.

The compounds of the invention can, optionally, be administered in combination with one or more additional drugs which, for example, are known for treating and/or alleviating symptoms of the condition mediated by NGF p75$^{NTR}$ or TrkA. The additional drug can be administered simultaneously with the compound of the invention, or sequentially. For example, the compounds of the invention can be administered in combination with at least one of an analgesic, an anti-inflammatory agent, an anesthetic, a corticosteroid (e.g., dexamethasone, beclomethasone diproprionate (BDP) treatment), an anti-convulsant, an antidepressant, an anti-nausea agent, an anti-psychotic agent, a cardiovascular agent (e.g., a beta-blocker) or a cancer therapeutic. In certain embodiments, the compounds of the invention are administered in combination with a pain drug. As used herein the phrase, "pain drugs" is intended to refer to analgesics, anti-inflammatory agents, anesthetics, corticosteroids, antiepileptics, barbiturates, antidepressants, and marijuana.

The combination treatments mentioned above can be started prior to, concurrent with, or after the administration of the compositions of the present invention. Accordingly, the methods of the invention can further include the step of administering a second treatment, such as a second treatment for the disease or disorder or to ameliorate side effects of other treatments. Such second treatment can include, e.g., anti-inflammatory medication and any treatment directed toward treating pain. Additionally or alternatively, further treatment can include administration of drugs to further treat the disease or to treat a side effect of the disease or other treatments (e.g., anti-nausea drugs, anti-inflammatory drugs, anti-depressants, anti-psychiatric drugs, anti-convulsants, steroids, cardiovascular drugs, and cancer chemotherapeutics).

As used herein, an "analgesic" is an agent that relieves pain without significant impairment of consciousness or sense perception and may result in the reduction of inflammation as do corticosteroids, e.g., an anti-inflammatory agent. Analgesics can be subdivided into NSAIDs (non-steroidal-anti-inflammatory agents), narcotic analgesics, and non-narcotic analgesics. NSAIDs can be further subdivided into non-selective COX (cyclooxygenase) inhibitors, and selective COX2 inhibitors. Opioid analgesics can be natural, synthetic or semi-synthetic opioid (narcotic) analgesics, and include for example, morphine, codeine, meperidine, propxyphen, oxycodone, hydromorphone, heroine, tramadol, and fentanyl. Non-opioid analgesics (non-narcotic) analgesics include, for example, acetaminophen, clonidine, NMDA antagonists, and cannabinoids. Non-selective COX inhibitors include, but are not limited to acetylsalicylic acid (ASA), ibuprofen, naproxen, ketoprofen, piroxicam, etodolac, and bromfenac. Selective COX2 inhibitors include, but are not limited to celecoxib, valdecoxib, parecoxib, and etoricoxib.

As used herein an "anesthetic" is an agent that interferes with sense perception near the site of administration, a local anesthetic, or result in alteration or loss of consciousness, e.g., systemic anesthetic agents. Local anesthetics include but are not limited to lidocaine and buvicaine.

Non-limiting examples of antiepileptic agents are carbamazepine, phenyloin and gabapentin. Non-limiting examples of antidepressants are amitriptyline and desmethylimiprimine.

Non-limiting examples of anti-inflammatory drugs include corticosteroids (e.g., hydrocortisone, cortisone, prednisone, prednisolone, methyl prednisone, triamcinolone, fluprednisolone, betamethasone and dexamethasone), salicylates, antihistamines and $H_2$ receptor antagonists.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, dosages of a compound of the invention may be determined by deriving dose-response curves using an animal model for the condition to be treated. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a subject, when used for the indicated analgesic effects, will range from about 0.0001 to about 100 mg per kilogram of body weight per day, more preferably from about 0.01 to about 100 mg per kg per day, and still more preferably from about 1.0 to about 50 mg per kg per day. An effective amount is that amount treats a neurotrophin-associated state or neurotrophin disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Methods of Treatment

The above compounds can be used for administration to a subject for the modulation of a neurotrophin-mediated activity, involved in, but not limited to, pain, inflammatory disorders, neurological disorders, and any abnormal function of cells, organs, or physiological systems that are modulated, at least in part, directly or indirectly by a neurotrophin-mediated activity. Additionally, it is understood that the compounds may also alleviate or treat one or more additional symptoms of a disease or disorder discussed herein.

Accordingly, in one aspect, the compounds of the invention may be used to treat pain, including acute, chronic, malignant and non-malignant somatic pain (including cutaneous pain and deep somatic pain), visceral pain, and neuropathic pain. It is further understood that the compounds may also alleviate or treat one or more additional signs or symptoms of pain and sensory deficits (e.g., hyperalgesia, allodynia, dysesthesia, hyperesthesia, hyperpathia, paresthesia).

In some embodiments of this aspect of the invention, the compounds of the invention may be used to treat somatic or cutaneous pain associated with injuries, inflammation, diseases and disorders of the skin, subcutaneous tissues and related organs including, but not limited to, cuts, burns, lacerations, punctures, incisions, surgical pain, post-operative pain, orodental surgery, psoriasis, eczema, dermatitis, and allergies. The compounds of the invention may also be used to treat somatic pain associated with malignant and non-malignant neoplasm of the skin, subcutaneous tissues and related organs (e.g., melanoma, basal cell carcinoma).

In other embodiments of this aspect of the invention, the compounds of the invention may be used to treat deep somatic pain associated with injuries, inflammation, diseases and disorders of the musculoskeletal and connective tissues including, but not limited to, arthralgias, myalgias, fibromyalgias, myofascial pain syndrome, dental pain, lower back pain, pain during labor and delivery, surgical pain, post-operative pain, headaches, idiopathic pain disorder, sprains, bone fractures, bone injury, osteoporosis, severe burns, gout, arthritis, osteoarthithis, myositis, and dorsopathies (e.g., spondylolysis, subluxation, sciatica, and torticollis). The compounds of the invention may also be used to treat deep somatic pain associated with malignant and non-malignant neoplasm of the musculoskeletal and connective tissues (e.g., sarcomas, rhabdomyosarcomas, and bone cancer).

In other embodiments of this aspect of the invention, compounds of the invention may be used to treat visceral pain associated with injuries, inflammation, diseases or disorders of the circulatory system, the respiratory system, the genitourinary system, the gastrointestinal system and the eye, ear, nose and throat.

For example, the compounds of the invention may be used to treat visceral pain associated with injuries, inflammation and disorders of the circulatory system including, but are not limited to, ischaemic diseases, ischaemic heart diseases (e.g., angina pectoris, acute myocardial infarction, coronary thrombosis, coronary insufficiency), diseases of the blood and lymphatic vessels (e.g., peripheral vascular disease, intermittent claudication, varicose veins, haemorrhoids, embolism or thrombosis of the veins, phlebitis, thrombophlebitis lymphadenitis, lymphangitis), and visceral pain associated with malignant and non-malignant neoplasm of the circulatory system (e.g., lymphomas, myelomas, Hodgkin's disease).

In another example, the compounds of the invention may be used to treat visceral pain associated with injuries, inflammation, diseases and disorders of the respiratory system including, but are not limited to, upper respiratory infections (e.g., nasopharyngitis, sinusitis, and rhinitis), influenza, pneumoniae (e.g., bacterial, viral, parasitic and fungal), lower respiratory infections (e.g., bronchitis, bronchiolitis, tracheobronchitis), interstitial lung disease, emphysema, bronchiectasis, status asthmaticus, asthma, pulmonary fibrosis, chronic obstructive pulmonary diseases (COPD), diseases of the pleura, and visceral pain associated with malignant and non-malignant neoplasm of the respiratory system (e.g., small cell carcinoma, lung cancer, neoplasm of the trachea, of the larynx).

In another example, the compounds of the invention may be used to treat visceral pain associated with injuries, inflammation and disorders of the gastrointestinal system including, but are not limited to, injuries, inflammation and disorders of the tooth and oral mucosa (e.g., impacted teeth, dental caries, periodontal disease, oral aphthae, pulpitis, gingivitis, periodontitis, and stomatitis), of the oesophagus, stomach and duodenum (e.g., ulcers, dyspepsia, oesophagitis, gastritis, duodenitis, diverticulitis and appendicitis), of the intestines (e.g., Crohn's disease, paralytic ileus, intestinal obstruction, irritable bowel syndrome, neurogenic bowel, megacolon, inflammatory bowel disease, ulcerative colitis, and gastroenteritis), of the peritoneum (e.g. peritonitis), of the liver (e.g., hepatitis, liver necrosis, infarction of liver, hepatic veno-occlusive diseases), of the gallbladder, biliary tract and pancreas (e.g., cholelithiasis, cholecystolithiasis, choledocholithiasis, cholecystitis, and pancreatitis), functional abdominal pain syndrome (FAPS), gastrointestinal motility disorders, as well as visceral pain associated with malignant and non-malignant neoplasm of the gastrointestinal system (e.g., neoplasm of the oesophagus, stomach, small intestine, colon, liver and pancreas).

In another example, the compounds of the invention may be used to treat visceral pain associated with injuries, inflammation, diseases, and disorders of the genitourinary system including, but are not limited to, injuries, inflammation and disorders of the kidneys (e.g., nephrolithiasis, glomerulonephritis, nephritis, interstitial nephritis, pyelitis, pyelonephritis), of the urinary tract (e.g. include urolithiasis, urethritis, urinary tract infections), of the bladder (e.g. cystitis, neuropathic bladder, neurogenic bladder dysfunction, overactive bladder, bladder-neck obstruction), of the male genital organs (e.g., prostatitis, orchitis and epididymitis), of the female genital organs (e.g., inflammatory pelvic disease, endometriosis, dysmenorrhea, ovarian cysts), as well as pain associated with malignant and non-malignant neoplasm of the genitourinary system (e.g., neoplasm of the bladder, the prostate, the breast, the ovaries).

In further embodiments of this aspect of the invention, compounds of the invention may be used to treat neuropathic pain associated with injuries, inflammation, diseases and disorders of the nervous system, including the central nervous system and the peripheral nervous systems. Examples of such injuries; inflammation, diseases or disorders associated with neuropathic pain include, but are not limited to, neuropathy (e.g., diabetic neuropathy, drug-induced neuropathy, radiotherapy-induced neuropathy), neuritis, radiculopathy, radiculitis, neurodegenerative diseases (e.g., muscular dystrophy), spinal cord injury, peripheral nerve injury, nerve injury associated with cancer, Morton's neuroma, headache (e.g., non-organic chronic headache, tension-type headache, cluster headache and migraine), multiple somatization syndrome, postherpetic neuralgia (shingles), trigeminal neuralgia complex regional pain syndrome (also known as causalgia or Reflex Sympathetic Dystrophy), radiculalgia, phantom limb pain, chronic cephalic pain, nerve trunk pain, somatoform pain disorder, central pain, non-cardiac chest pain, central post-stroke pain.

In another aspect, the compounds of the invention may be used to treat inflammation associated with injuries, diseases or disorders of the skin, subcutaneous tissues and related organs, the musculoskeletal and connective tissue system, the respiratory system, the circulatory system, the genitourinary system and the gastrointestinal system.

In some embodiments of this aspect of the invention, examples of inflammatory conditions, diseases or disorders of the skin, subcutaneous tissues and related organs that may be treated with the compounds of the invention include, but are not limited to allergies, atopic dermatitis, psoriasis, eczema and dermatitis.

In other embodiments of this aspect of the invention, inflammatory conditions, diseases or disorders of the musculoskeletal and connective tissue system that may be treated with the compounds of the invention include, but are not limited to arthritis, osteoarthritis, and myositis.

In other embodiments of this aspect of the invention, inflammatory conditions, diseases or disorders of the respiratory system that may be treated with the compounds of the invention include, but are not limited to allergies, asthma, rhinitis, neurogenic inflammation, pulmonary fibrosis, chronic obstructive pulmonary disease (COPD), adult respiratory distress syndrome, nasopharyngitis, sinusitis, and bronchitis.

In still other embodiments of this aspect of the invention, inflammatory conditions, disease or disorders of the circulatory system that may be treated with the compounds of the invention include, but are not limited to, endocarditis, pericarditis, myocarditis, phlebitis, lymphadenitis and artherosclerosis.

In further embodiments of this aspect of the invention, inflammatory conditions, diseases or disorders of the genitourinary system that may be treated with the compounds of the invention include, but are not limited to, inflammation of the kidney (e.g., nephritis, interstitial nephritis), of the bladder (e.g., cystitis), of the urethra (e.g., urethritis), of the male genital organs (e.g., prostatitis), and of the female genital organs (e.g., inflammatory pelvic disease).

In further embodiments of this aspect of the invention, inflammatory conditions, diseases or disorders of the gastrointestinal system that may be treated with the compounds of the invention include, but are not limited to, gastritis, gastroenteritis, colitis (e.g., ulcerative colitis), inflammatory bowel syndrome, Crohn's disease, cholecystitis, pancreatitis and appendicitis.

In still further embodiments of this aspect of the invention, inflammatory conditions, diseases or disorders that may be treated with the compounds of the invention, but are not limited to inflammation associated with microbial infections (e.g., bacterial, viral and fungal infections), physical agents (e.g., burns, radiation, and trauma), chemical agents (e.g., toxins and caustic substances), tissue necrosis and various types of immunologic reactions and autoimmune diseases (e.g., Lupus erythematosus).

In another aspect, the compounds of the invention may be used to treat injuries, diseases or disorders of the nervous system including, but not limited to neurodegenerative diseases (e.g., Alzheimer's disease, Duchenne's disease), epilepsy, multiple sclerosis, amyotrophic lateral sclerosis, stroke, cerebral ischemia, neuropathies (e.g., chemotherapy-induced neuropathy, diabetic neuropathy), retinal pigment degeneration, trauma of the central nervous system (e.g., spinal cord injury), and cancer of the nervous system (e.g., neuroblastoma, retinoblastoma, brain cancer, and glioma), and other certain cancers (e.g., melanoma, pancreatic cancer).

In further aspects of the invention, the compounds of the invention may also be used to treat other disorders of the skin, subcutaneous tissues and related organs (e.g., hair loss), of the respiratory system (e.g., asthma), of the circulatory system, (e.g., cardiac arrhythmias and fibrillation and sympathetic hyper-innervation), and of the genitourinary system (e.g., neurogenic bladder dysfunction and overactive bladder).

The present invention provides a method for treating a subject that would benefit from administration of a composition of the present invention. Any therapeutic indication that would benefit from a NGF/NTR modulator (i.e., a compound of the invention) can be treated by the methods of the invention. The method includes the step of administering to the subject a composition of the invention, such that the disease or disorder is treated.

The invention further provides a method for preventing in a subject, a disease or disorder which can be treated with administration of the compositions of the invention. Subjects "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a disease or disorder that may be treated according the methods of the invention. For example, risk factors include family history, medication history, and history of exposure to an environmental substance which is known or suspected to increase the risk of disease. Subjects at risk for a disease or condition which can be treated with the agents mentioned herein can also be identified by, for example, any or a combination of diagnostic or prognostic assays known to those skilled in the art. Administration of a prophylactic agent can occur prior to the manifestation of symptoms characteristic of the disease or disorder, such that the disease or disorder is prevented or, alternatively, delayed in its progression.

EXEMPLIFICATION OF THE INVENTION

The invention is further illustrated by the following example, which could be used to examine the neurotrophin/neurotrophin precursor binding inhibition of the compounds of the invention. The example should not be construed as further limiting. The animal models used throughout the Examples are accepted animal models and the demonstration of efficacy in these animal models is predictive of efficacy in humans.

Compound Synthesis

Example 1

General Procedure for the Preparation
Naphthalimide Derivatives

To a stirred solution of naphthalic anhydride derivative (1 equiv.) in glacial acetic acid was added, under an $N_2$ atmosphere, the primary amine (1 equiv.) and sodium acetate (1 equiv.). The reaction mixture was brought to reflux. Refluxing was continued and the progress of the reaction was monitored by TLC. Upon completion, if the resultant solution was clear, then the solvent was evaporated under reduced pressure and the residual solid was reprecipitated and/or recrystallised from appropriate solvent(s). If the final mixture contained precipitate then the mixture was cooled to room temperature and the solid was collected by filtration, washed with distilled water or dilute acid and further reprecipitated and/or recrystallised from appropriate solvent(s). The filtrate was recovered and treated as the clear solution to obtain further product. The final products were dried in vacuum for 24-48 hours.

Example 2

4-(5-Nitro-1,3-dioxo-1H,3H-benzo[de]isoquinolin-2-yl)-butyric acid (Compound 63)

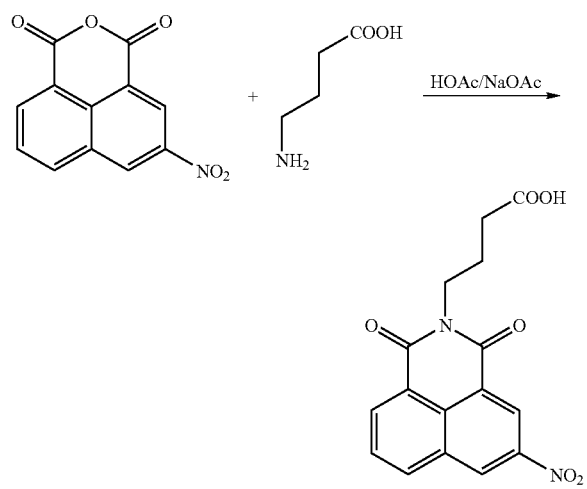

The compound was prepared from 3-nitro-1,8-naphthalic anhydride (1.00 g, 4.1 mmol) and 4-aminobutyric acid (0.42 g, 4.1 mmol) in 100 mL glacial acetic acid using the general procedure shown in Example 1.

$^1$H NMR (d6-DMSO, 400 MHz): 1.86-1.93 (m, 2H), 2.33 (t, J=7.2 Hz, 2H), 4.08 (t, J=6.8 Hz, 2H), 8.01 (t, J=8.0, 1H), 8.61 (d, J=7.6 Hz, 1H), 8.70 (d, J=8.4 Hz, 1H), 8.86 (d, J=2.0 Hz, 1H), 9.40 (d, J=2.0 Hz, 1H), 12.01 (bs, 1H); $^{13}$C NMR: 23.7, 32.1, 40.1, 123.4, 123.5, 124.9, 130.0, 130.3, 130.4, 131.6, 134.7, 137.0, 146.6, 163.2, 163.7, 174.8. MS (ES+) m/z: 275 (55%) 191 (100%).

Example 3

Preparation of 3,6-Dinitro-1,8-naphthalic anhydride

To a solution of 1,8-naphthalic anhydride (6 g, 25 mmol) in concentrated sulfuric acid (18 mL) was added a mixture of concentrated sulfuric acid (18 mL), concentrated nitric acid (14 mL) and fuming nitric acid (4 mL), dropwise to keeping the temperature less than 30° C. Once the addition was complete, the reaction mixture was heated at 60° C. for 1 hour. After cooling, the mixture was poured into ice/water, and the resulting solid was filtered and crystallized from acetic acid to give 3,6-Dinitro-1,8-naphthalic anhydride as pale yellow solid.

$^1$H NMR (d6-DMSO, 400 MHz): 9.08 (d, J=2.4 Hz, 2H), 9.82 (d, J=2.0 Hz, 2H).

An alternative procedure for 3,6-dinitro naphthalic anhydride is as follows: to a stirred solution of 1,8-naphthalic anhydride (60 g, 0.3 mol) in 240 mL concentrated sulfuric acid was added, dropwise, concentrated nitric acid (60 mL, 68-70%) keeping the temperature below 30° C. Once the addition was complete, the reaction mixture was heated to 60° C. for 90 min. The reaction solution was brought to room temperature and poured in ice/water bath. The resulting yellow solid was filtered and washed with water. The pale yellowish solid was dried in a vacuum oven, resulting in 73 g of 3,6-dinitro-1,8-naphthalic anhydride, yield 84%. The product was used for the next step without further purification. (3,6-Dinitro naphthalic anhydride can also be made from 3-nitro naphthalic anhydride (99% pure, Acros))

$^1$H NMR (d6-DMSO, 400 MHz): 9.08 (d, 2H, J=2.1 Hz), 9.82 (d, 2H, J=2.1 Hz)

Example 4

4-(5,8-Dinitro-1,3-dioxo-1H,3H-benzo[de]isoquinolin-2-yl)-butyric acid (Compound 10)

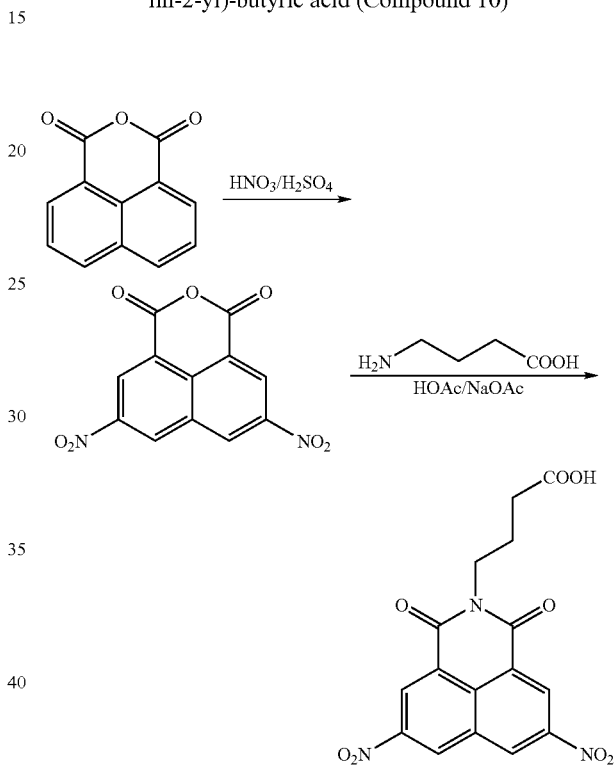

3,6-Dinitro-1,8-naphthalic anhydride (see example 3; 1.44 g, 5 mmol) and 4-aminobutyric acid (0.52 g, 5 mmol) were reacted in 100 mL glacial acetic acid using the general procedure shown in Example 1 to produce 4-(5,8-Dinitro-1,3-dioxo-1H,3H-benzo[de]isoquinolin-2-yl)-butyric acid.

$^1$H NMR (d6-DMSO, 400 MHz): 1.89-1.94 (m, 2H), 2.35 (t, J=7.2 Hz, 2H), 4.13 (t, J=6.8 Hz, 2H), 9.07 (d, J=2.0 Hz, 2H), 9.76 (d, J=2.0 Hz, 2H), 12.04 (bs, 1H); $^{13}$C NMR (dept): 23.6, 32.1, 40.7, 126.6, 132.2; MS (ES−) m/z: 372.0 (M−1, 55%), 286.0 (100%).

In an alternative procedure, 3,6-dinitro-1,8-naphthalic anhydride (15 g, 52 mmol), 4-aminobutyric acid (10.9 g, 104 mmol) and sodium acetate (5.0 g) were added to 500 mL of glacial acetic acid. The mixture was heated to reflux overnight. The reaction mixture was cooled to room temperature and concentrated to about 200-250 mL. The pale brown precipitate was collected by filtration and washed with acetic acid. The final product was dried in vacuum for 24 hours. The yield of desired compound was less than 50%

$^1$H NMR (d6-DMSO, 400 MHz): 1.92 (m, 2H), 2.34 (t, 2H, J=7.3 Hz), 4.13 (t, 2H, J=6.8 Hz), 9.05 (d, 2H, J=2.0 Hz), 9.76 (d, 2H, J=2.0 Hz), 12.08 (bs, 1H)

Example 5

4-(5,8-Diamino-1,3-dioxo-1H,3H-benzo[de]isoquinolin-2-yl)-butyric acid (Compound 9)

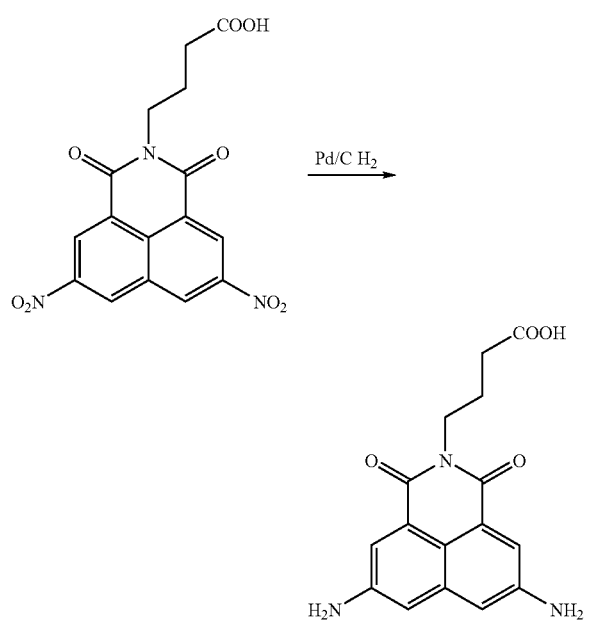

A mixture of 4-(5,8-Dinitro-1,3-dioxo-1H,3H-benzo[de]isoquinolin-2-yl)-butyric acid (see example 4; 0.37 g, 1 mmol), palladium on charcoal 10% and dimethylformamide (20 mL) was hydrogenated at room temperature with vigorous stirring for 24 hours. The catalyst was filtered off and the filtrate evaporated under reduced pressure. The residue was crystallized from dimethylformamide and water to give the desired product.

$^1$H NMR (d6-DMSO, 400 MHz): 1.81-1.85 (m, 2H), 2.27 (t, J=7.2 Hz, 2H), 4.01 (t, J=6.8 Hz, 2H), 5.68 (bs, 4H), 6.92 (d, J=2.0 Hz, 2H), 7.57 (d, J=2.0 Hz, 2H), 12.04 (bs, 1H); $^{13}$C NMR (dept): 24.0, 32.2, 39.8, 110.4, 117.8; MS (ES−) m/z: 312.1 (M−1, 100%), 226.0 (30%).

In an alternative procedure, a mixture of 4-[5,8-bis(nitro)-1,3-dioxo-1H-benzo[de]isoquinolin-2(3H)-yl]-butanoic acid (3.0 g, 8 mmol), 10% palladium on charcol (0.8 g) and dimethylformamide (100 mL) was hydrogenated with hydrogen balloon at room temperature with vigorous stirring, and monitored with TLC until the reaction came to completion. The catalyst was filtered off and the filtrate evaporated under reduced pressure. The residue was washed with water and dried in vacuum for 24 hours, resulting in a green solid, weight 2.4 g, yield 95.8%.

$^1$H NMR (6-DMSO, 400 MHz): 1.84 (m, 2H), 2.27 (t, 2H, J=7.2 Hz), 4.02 (t, 2H, J=6.8 Hz), 5.69 (bs, 4H), 6.92 (d, 2H, J=2.0 Hz), 7.57 (d, 2H, J=2.0 Hz), 12.01 (bs, 1H)

Example 6

4-(5,8-Bis-acetylamino-1,3-dioxo-1H,3H-benzo[de]isoquinolin-2-yl)-butyric acid (Compound 11)

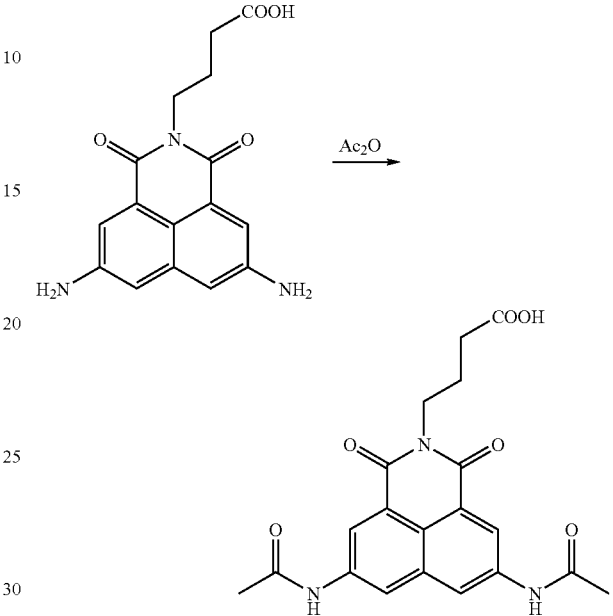

A mixture of 4-(5,8-Diamino-1,3-dioxo-1H,3H-benzo[de]isoquinolin-2-yl)-butyric acid (0.31 g, 1 mmol) and acetic anhydride (15 mL) in dimethylformamide was stirred at room temperature until the reaction was complete. The solvent was evaporated under reduced pressure and the residue was crystallized from dimethylformamide and water to give the desired product.

$^1$H NMR (d6-DMSO, 400 MHz): 1.94-1.97 (m, 2H), 2.13 (s, 6H), 2.57 (t, J=7.2 Hz, 2H), 4.11 (t, J=6.8 Hz, 2H), 8.44 (s, 2H), 8.56 (s, 2H), 10.37 (s, 2H); $^{13}$C NMR: 21.4, 23.8, 24.6, 32.0, 120.6, 121.5, 122.8, 123.2, 133.7, 139.0, 164.2, 169.8, 174.7; MS (ES−) m/z: 396.1 (M−1, 100%), 310.1 (10%).

In an alternative procedure, a mixture of 4-[5,8-bis (amino)-1,3-dioxo-1H-benzo[de]isoquinolin-2(3H)-yl]-butanoic acid (1.0 g, 3.2 mmol), dimethylformamide (25 mL) and acetic anhydride (25 mL) was stirred at room temperature overnight. The precipitate was collected by filtration and washed with water. The crude product (1.0 g) then was dissolved into the mixture of pyridine (30 mL) and water (20 mL) solution. After room temperature stirring for 30 min, most of the solvents were removed under reduced pressure. Hydrogen chloride solution (conc., 15 mL), followed by distilled water (150 mL) was added. The pale yellow precipitate was filtered and washed with water and dried in vacuum for 24 hours, resulting in a pale yellow solid, weight 1.1 g, yield 86.5%.

$^1$H NMR (6-DMSO, 400 MHz): 1.88 (m, 2H), 2.15 (s, 6H), 2.31 (t, 2H, J=7.2 Hz), 4.06 (t, 2H, J=7.2 Hz), 8.46 (d, 2H, J=2.0 Hz), 8.59 (d, 2H, J=2.0 Hz), 10.51 (s, 2H)

Example 7

4-(5-Cyano-1,3-dioxo-1H,3H-benzo[de]isoquinolin-2-yl)-butyric acid (Compound 124)

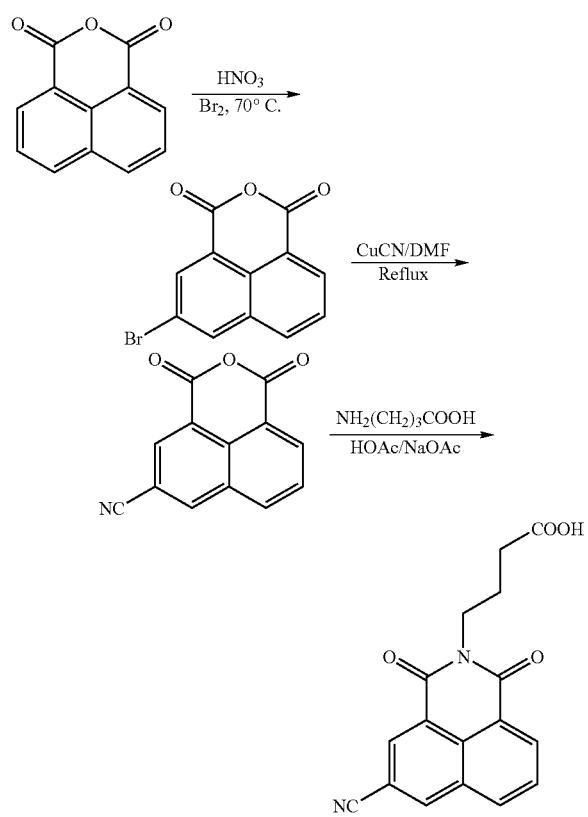

3-Bromo-1,8-naphthalic anhydride

Bromine (13.2 mL, 256 mmol) was added to a stirred solution of 1,8-naphthalic anhydride (50 g, 252 mmol) in 70% nitric acid (1000 mL) at 25° C. over a period of 10 min. The resulting brown solution was stirred at 70° C. for 2 hrs and cooled overnight. The cream colored precipitate was collected by filtration and washed with water (4×150 mL). The isolated product was dried in vacuum for 24 hrs, resulting in off-white crystalline solid (12.0 g, 20% yield).

3-Cyano-1,8-naphthalic anhydride

A mixture of 3-bromo-1,8-naphthalic anhydride (17.0 g, 61 mmol), copper cyanide (8.4 g) and dimethylformamide (250 mL) was stirred at reflux temperature overnight (reaction was monitored by TLC). The reaction mixture was cooled to room temperature and then quenched by pouring over crushed ice. The solid was filtered, washed with water and dried under vacuum for 24 hrs. The residue was passed through silica gel using methylene chloride as eluent. The organic solvent was washed with 0.15 M of EDTA-disodium salt until the aqueous layer no longer retained the characteristic blue color of solvated copper ions (4-5 times, aliquot was checked with $NH_4OH$) and washed with brine. The solvent was dried over sodium sulphate and evaporated, resulting in a yellow solid. Yield 40%

4-(5-Cyano-1,3-dioxo-1H,3H-benzo[de]isoquinolin-2-yl)-butyric acid (Compound 124)

3-Cyano-1,8-naphthalic anhydride (31 g, 139 mmol), 4-aminobutyric acid (24 g, 233 mmol) and sodium acetate (12.0 g) was reacted in 1200 mL glacial acetic acid. The mixture was heated to reflux for 1-2 days and the reaction was monitored by TLC. The reaction mixture was cooled to room temperature and concentrated to about 400-450 mL. The precipitate was collected by filtration and washed with acetic acid. The pale yellow solid was dissolved by refluxing with acetic acid and solid precipitate out at room temperature. The solid was dried in vacuum for 24 hours. Yield 40%

Example 8

4-(5-Carbamoyl-1,3-dioxo-1H,3H-benzo[de]isoquinolin-2-yl)-butyric acid (Compound 95) and 2-(3-Carboxy-propyl)-1,3-dioxo-2,3-dihydro-1H-benzo[de]isoquinoline-5-carboxylic acid (Compound 128)

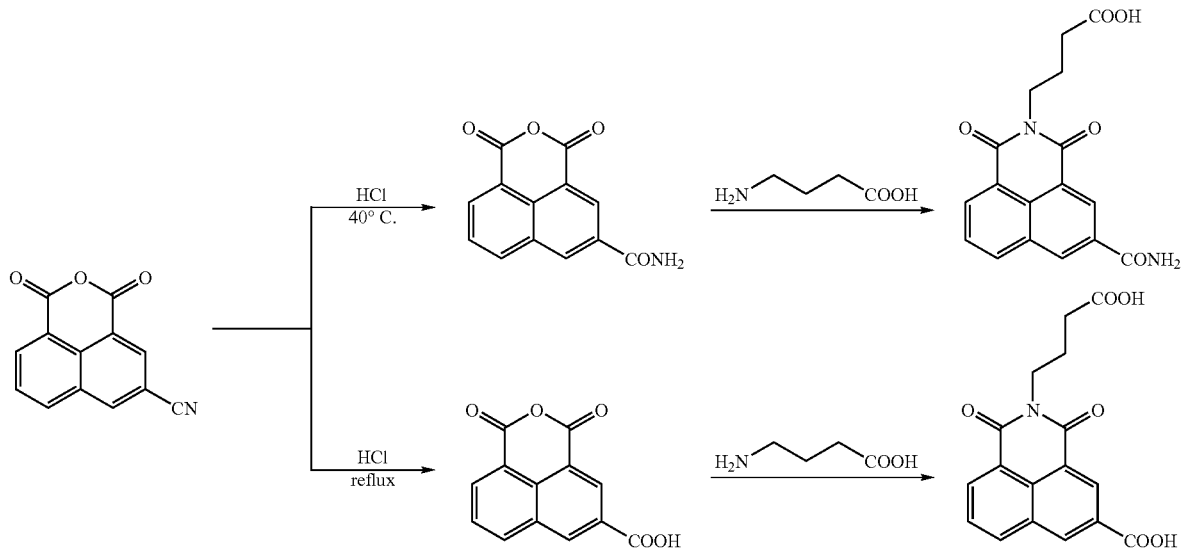

4-(5-Carbamoyl-1,3-dioxo-1H,3H-benzo[de]isoquinolin-2-yl)-butyric acid (Compound 95)

A mixture of 3-Cyano-1,8-naphthalic anhydride in hydrochloric acid (35%) was heated at 40° C. for 4-5 hrs (reaction monitored by TLC). After cooling to room temperature, the reaction mixture was quenched with ice-water. The solid separated was collected by filtration, washed with water and dried to get 1,3-dioxo-1H,3H-benzo[de]isochromene-5-carboxamide as off-white solid in quantitative yield.

A mixture of 1,3-dioxo-1H,3H-benzo[de]isochromene-5-carboxamide (0.5 mmol), 4-Aminobutyric acid (1.5 mmol) and 4 mL ethanol was heated to 150° C. for 30 minutes in microwave reactor (Biotage, Initiator). The reaction mixture was cooled to room temperature and the cream color precipitate was collected by filtration and washed with ethanol. The final product was dried in vacuum for 24 hours to give desired compound.

2-(3-Carboxy-propyl)-1,3-dioxo-2,3-dihydro-1H-benzo[de]isoquinoline-5-carboxylic acid (Compound 128)

1,3-dioxo-1H,3H-benzo[de]isochromene-5-carboxylic acid was obtained by heating 3-cyano-1,8-naphthalic anhydride with HCl (35%) at reflux temperature overnight. After cooling to room temperature, the reaction mixture was quenched with ice water. The solid was collected by filtration, washed with water and dried under vacuum to get desired product as white solid in quantitative yield.

A mixture of anhydride (0.5 mmol), 4-aminobutyric acid (1.5 mmol) and 4 mL ethanol was heated to 150° C. for 30 minutes in microwave reactor (Biotage, Initiator). The reaction mixture was cooled to room temperature and the white precipitate was collected by filtration and washed with ethanol. The final product was dried in vacuum to give the desired compound.

Biological Activity

Materials and Methods

Cell Culture

All cells were incubated at 37° C. in 5% CO2. PC12 cells were maintained in RPMI-1640 medium supplemented with 10% fetal bovine serum (FBS). A875 human melanoma cells were maintained in DMEM with 10% FBS. HEK 293 cells were stably transfected with human TrkA plasmid (see below) and maintained in DMEM with 10% FBS and G418 (600 μg/mL) for selection.

Cell Transfections:

Expression of human TrkA in HEK cells was achieved by transfecting the cells with the TrkA expression vector using Lipofectamine (Invitrogen) reagent. HEK cells were plated in 100 mm Petri dishes at a concentration of $10^6$ cells per dish. The next day, a solution of DNA diluted in 1 mL OptiMEM (Invitrogen) per dish was prepared and incubated for 15 min at room temperature. Concurrently, 42 μl of Lipofectamine reagent was prepared in OPtiMEM (1 mL per dish) and incubated for 15 min at room temperature. The DNA and lipofectamine reagent solutions were then mixed together and incubated for a further 15 minutes. During this 30 min of incubation, the cells were rinsed twice with OptiMEM. The DNA-lipofectamine solution in OptiMEM was then added to the dish, which was then placed in the incubator (37° C.; 5% $CO_2$) for 3 h. This solution was then aspirated and the cells were rinsed with DMEM. From this point, cells were grown in DMEM+FBS (10%), their normal growth medium. For stable cell lines, the culture medium contained G418 (600 μg/mL) a selection agent for maintenance of TrkA expression in the cells. The presence of TrkA was confirmed with $^{125}$I-NGF binding (see below) and Western blots (see below) labeled with TrkA specific antisera.

Example 1

NGF Binding

NGF binding was evaluated using methods familiar to those who are skilled in the art. Briefly, cells expressing one or both NGF receptors (PC12: TrkA+p75; A875: p75 alone; HEK_TrkA: TrkA alone) were harvested by replacing the medium with calcium-magnesium free balanced salt (Grey's) solution and incubating at 37° C. for 15 min. For NGF binding, cells were resuspended at a concentration of $2 \times 10^6$ cells/mL in HEPES-Krebs-Ringer (HKR) buffer (10 mM HEPES; 125 mM NaCl; 4.8 mM KCl; 1.3 mM $CaCl_2$; 1.2 mM $MgSO_4$; 1.2 mM $KH_2PO_4$; 1 mg/ml BSA; 1 mg/ml glucose; pH 7.4) and exposed to $^{125}$I-NGF (~0.11 nM) in the presence or absence of varying concentrations of the compound. Non-specific binding was determined for reference by incubating $^{125}$I-NGF with an excess of non-radioactive NGF in the absence of compound. Following a two-hour incubation period at 4° C., $^{125}$I-NGF bound to the cells was quantified in a gamma radiation counter following separation from unbound NGF by filtration or centrifugation through glycerol (10% in HKR). Inhibition of binding was calculated as a percent of the specific binding (calculated as the differential between $^{125}$I-NGF binding in the absence and presence of an excess of non-radioactive NGF without compound). Dose-response inhibition curves were typically generated with seven concentrations of a given compound, with three replicates for each concentration. For most compounds, multiple dose-response curves were generated.

The $IC_{50}$ data shown in Table 1 were acquired using the procedure described herein using PC12 cells. Examples of $IC_{50}$ calculation curves from individual experiments using this procedure are shown in FIGS. 1B, 2A, 2B, 4A, 4B, 6A, 6B, 7A, 8A and 8B, in which compounds 11, 124, 107 and 63, are shown to effectively block NGF binding to TrkA and/or p75.

Example 2

NGF Crosslinking to Receptors

NGF binding to TrkA and p75 was qualitatively evaluated following chemical cross-linking, and separation of proteins according to molecular weight with SDS-PAGE. PC12 (for p75 and TrkA binding), HEK_TrkA (for TrkA only) and A875 (for p75 only) cells were recovered using Grey's solution, pelleted by centrifugation, and suspended in HKR. In a total volume of 1 mL $2 \times 10^6$ cells/mL were incubated, rotating, with ~0.1 nM $^{125}$I-NGF, with or without the compound for 2 h at 4° C. At the conclusion of the binding reaction, a 20 μL volume of $BS^3$ (Bis[sulfosuccinimidyl]suberate) crosslinker was added for a final concentration 0.4 mM and incubated, rocking, for an additional 30 min at room temperature. Cells were washed twice in HKR. Following centrifugation, the pellets were solubilized directly in SDS sample buffer and heated for 10 min at 95° C. All samples were electrophoresed on a 6% SDS-PAGE gel, which was then dried and autoradiographed. Bands at the appropriate molecular weights for p75-NGF conjugates and TrkA-NGF conjugates were visualized by exposing the dried gel to film overnight (BioMax, Kodak) overnight. Modulatory effects of the compounds on NGF binding were determined by variations in band intensity. Reduced binding of NGF to its receptors was represented by lighter bands.

Results from this qualitative evaluation are in accordance with the quantitative data from the binding assay of Example 1.

Example 3

Erk Phosphorylation

This assay is useful for establishing that the compounds of the invention are functional NGF antagonists, not receptor agonists (an agonist could conceivably block NGF binding but actually activate the receptor). Erk 1/2 is a kinase activated down stream of TrkA and is a well studied member of the NGF-induced signal transduction cascade.

PC12 cells expressing TrkA and p75 were acutely exposed to 5 ng/mL NGF (15 min; 37° C.; 5% $CO_2$) that was pre-incubated (30 min; room temperature) with or without the compounds. Cells were lysed in Laemmli sample buffer (for SDS-PAGE) or a lysis buffer containing Triton X-100 (for ELISA). Following SDS-PAGE, proteins were electroblotted onto nitrocellulose and immunoprobed for phosphorylated Erk 1 and 2. Blocking and primary antibody incubations of immunoblots were performed in Tris-buffered saline-Tween (10 mM Tris, pH 8.0, 150 mM NaCl, and 0.2% Tween 20) supplemented with 5% (w/v) bovine serum albumin (BSA); secondary antibody incubations were performed in 5% (w/v) dried skim milk powder. Immunoreactive bands were detected by chemiluminescence.

Figure 3:
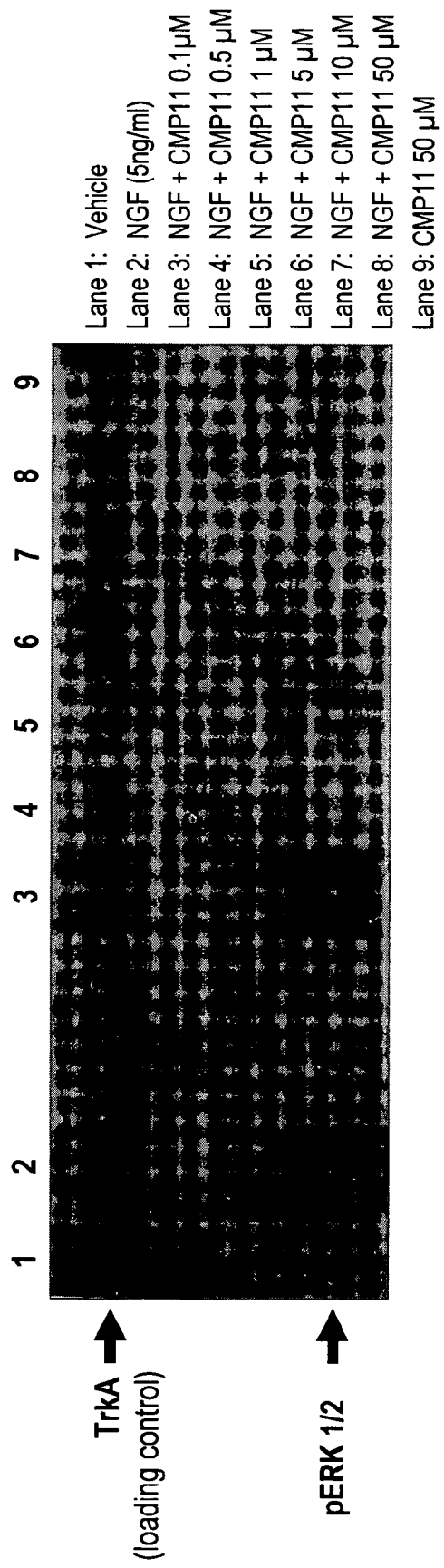
FIG. 3 shows a typical Western blot with immunodetection of phosphorylated Erk proteins extracted from NGF-stimulated PC12 cells in the presence or absence of Compound 11, as described in Example 3. These results demonstrate that Compound 11 inhibits NGF-induced Erk 1/2 phosphorylation in PC12 cells.
Figure 4B:
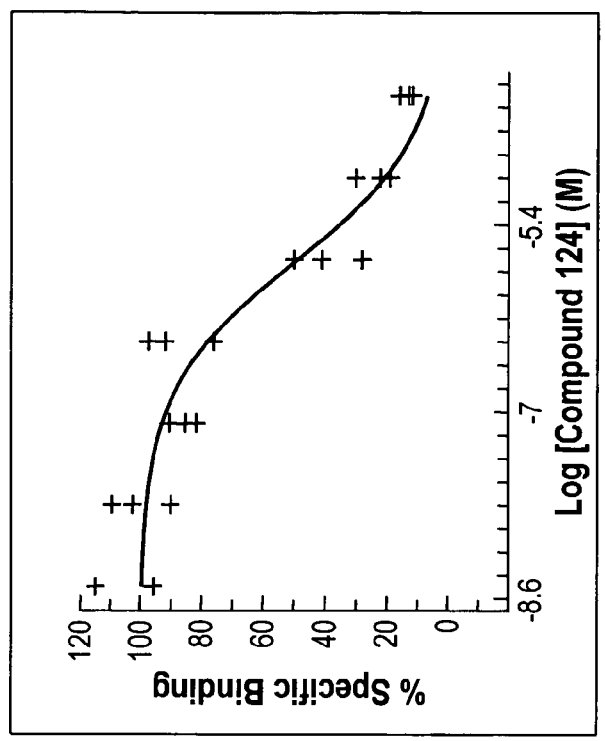
FIG. 4B shows a dose-response curve for Compound 124 from an individual NGF binding displacement experiment in PC12 cells as described in Example 1. The dose-response curve demonstrates that Compound 124 effectively blocks NGF binding to cells expressing TrkA and p75.
Figure 4A:
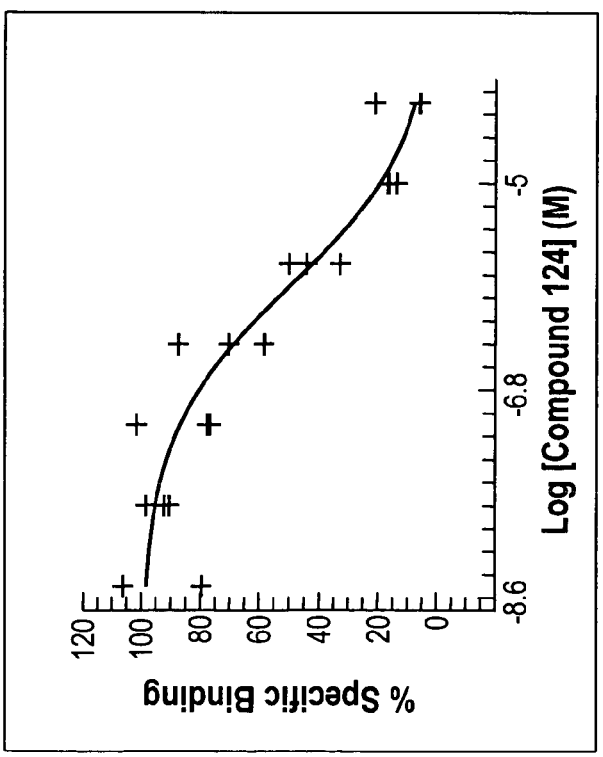
FIG. 4A shows a dose-response curve for Compound 124 from an individual NGF binding displacement experiment in A875 cells as described in Example 1. The dose-response curve demonstrates that compound 124 effectively blocks NGF binding to cells expressing p75.
Figure 5:
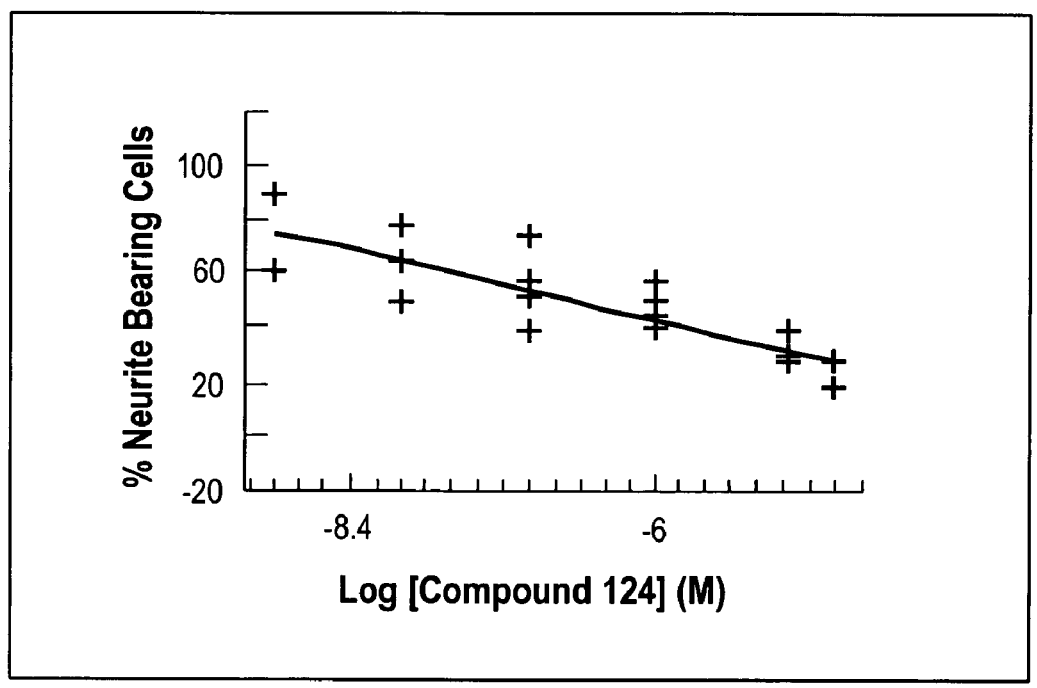
FIG. 5 shows a neurite outgrowth inhibition curve for Compound 124 resulting from an experiment as described in Example 4. The curve demonstrates that Compound 124 effectively inhibits neurite outgrowth induced by NGF.
Figures 6A, 6B:
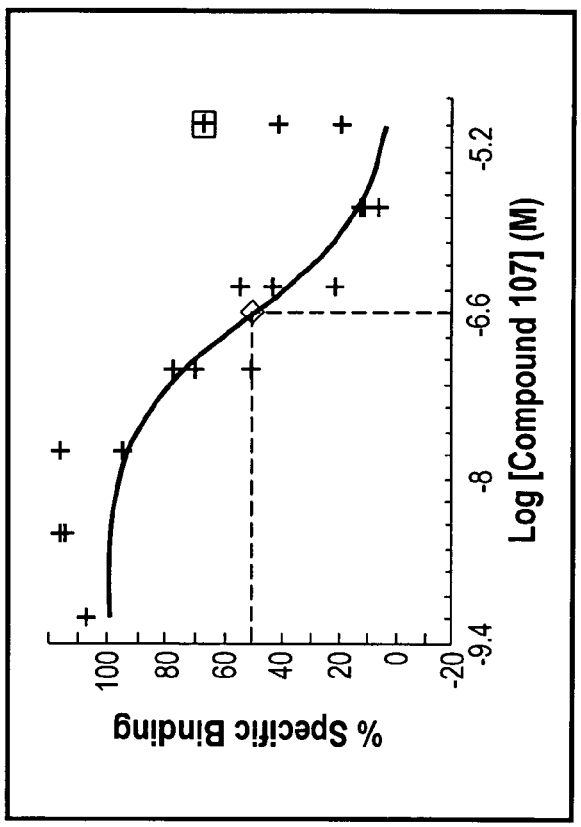
FIG. 6A shows a dose-response curve for Compound 107 from an individual NGF binding displacement experiment in PC12 cells as described in Example 1. The dose-response curve demonstrates that compound 107 effectively blocks NGF binding to cells expressing TrkA and p75.
FIG. 6B shows a dose-response curve for compound 107 from an individual NGF binding displacement experiment in HEK_trkA cells as described in Example 1. The dose-response curve demonstrates that compound 107 effectively blocks NGF binding to cells expressing TrkA.
Figure 7A:
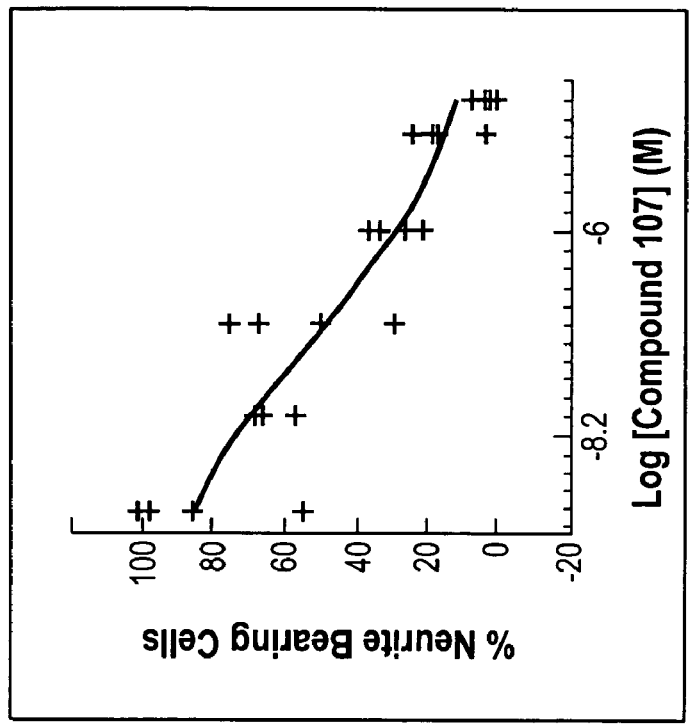
FIG. 7A shows a dose-response curve for Compound 107 from an individual NGF binding displacement experiment in A875 cells as described in Example 1. The dose-response curve demonstrates that compound 107 effectively blocks NGF binding to cells expressing p75.
Figure 7B:
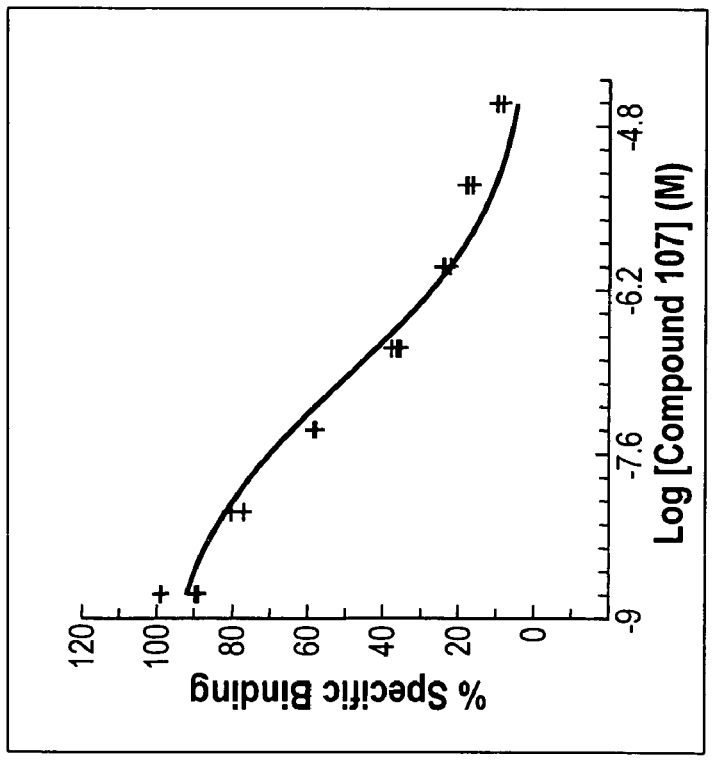
FIG. 7B shows a neurite outgrowth inhibition curve for Compound 107 resulting from an experiment as described in Example 4. The curve demonstrates that compound 107 effectively inhibits neurite outgrowth induced by NGF.
Figure 9:
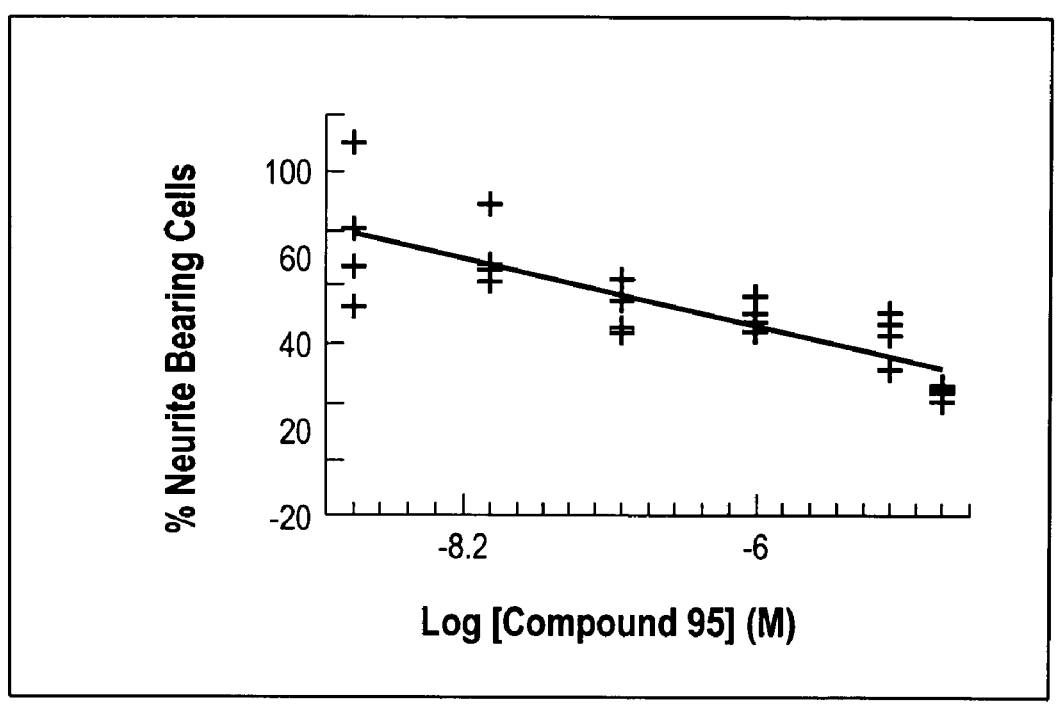
FIG. 9 shows a neurite outgrowth inhibition curve for Compound 95 resulting from an experiment as described in Example 4. The curve demonstrates that compound 95 effectively inhibits neurite outgrowth induced by NGF.

A representative example of a phosphorylated-Erk blot 1/2 for Compound 11 is shown in FIG. 3, which demonstrates that Compound 11 inhibits NGF-induced Erk 1/2 phosphorylation in PC12 cells.

To detect phosphorylated Erk 1/2 by ELISA, a kit from R&D (Minneapolis, Minn.) Systems is used. Briefly, cells are lysed in buffer (1 mM EDTA, 0.5% Triton X-100, 5 mM NaF, 1 M urea, 10 µg/mL, Leupeptin, 10 µg/mL Pepstatin, 100 µM PMSF, 3 µg/mL Aprotinin, 2.5 mM sodium pyrophosphate, 1 mM sodium orthovanadate in PBS, pH 7.2-7.4). Lysates are incubated overnight at 4° C. in ELISA plates coated with an anti-Erk 1/2 capture antibody. Immobilized Erk 1/2 is then exposed to a biotinylated detection antibody specific for phosphorylated Erk. The quantity of phosphorylated Erk 1/2 is quantified colorometrically with a standard HRP-streptavidin reaction.

Example 4

Neurite Outgrowth

This assay was run as a further functional marker of NGF antagonism and takes advantage of the differentiation of PC12 cells (neurite outgrowth) induced by NGF. Cultures of PC12 cells were grown on Terasaki plates pre-coated with poly-D-lysine. Cells were exposed to NGF (1-50 (preferably 5) ng/ml) to induce neurite outgrowth as described elsewhere [L A Greene & A S Tischler, *Establishment of a noradrenergic clonal line of rat adrenal pheochromocytoma cells which respond to nerve growth factor, Proc Natl Acad Sci USA.* 1976 July; 73(7): 2424-2428]. In addition to NGF, cells were exposed to varying concentration of the compounds or vehicle. Following 4 days of exposure to NGF in the presence or absence of compound, neurite outgrowth was quantified. A neurite was scored if its caliber from origin to terminal was approximately the same and the length was equal to or greater than 1.5 the cell body diameter. The number of neurite bearing cells per total number of viable cells was calculated for each condition; the number of cells with neurites in the presence of NGF (without compound exposure) was considered to represent maximal (100%) outgrowth, to which the inhibitory effect of compounds of the invention on NGF-induced outgrowth was compared.

Results from this experiment are shown in FIGS. 1A, 5, 7B, and 9, which demonstrate that compounds 11, 124, 107 and 95, respectively, effectively inhibit neurite outgrowth induced by NGF. The x-axis represents the log concentration in M.

Example 5

Formalin Model—Model of Acute Tonic Pain

Male Sprague-Dawley rats were given a subcutaneous injection of 50 µl of 2.5% formalin into the plantar surface of one hindpaw using a 27 gauge syringe needle, and nociceptive responses were measured for the next 60 min. Compound or vehicle was administered (i.p. or s.c.) 15-45 minutes prior to the formalin injection. A nociceptive score was determined for each 5 min block by measuring the amount of time spent in each of four behavioral categories: 0, the injected hindpaw is indistinguishable from that of the contralateral paw; 1, the injected paw has little or no weight placed on it; 2, the injected paw is elevated and is not in contact with any surface; 3, the injected paw is licked, bitten, or shaken. A weighted nociceptive score, ranging from 0 to 3 was calculated by multiplying the time spent in each category by the category weight, summing these products, and dividing by the total time for each 5 min block of time (Coderre et al., Pain 1993; 54: 43). On the basis of the resulting response patterns, 2 phases of nociceptive behaviour were identified and scored: first phase (P1; 0-5 min) and second phase (P2; 11-40 min).

Statistical analysis was performed using Prism™ 4.01 software package (GraphPad, San Diego, Calif., USA). The difference in response levels between treatment groups and control vehicle group was analyzed using an ANOVA followed by Bonferroni's method for post-hoc pair-wise comparisons. A p value <0.05 was considered to be significant.

Figure 11:
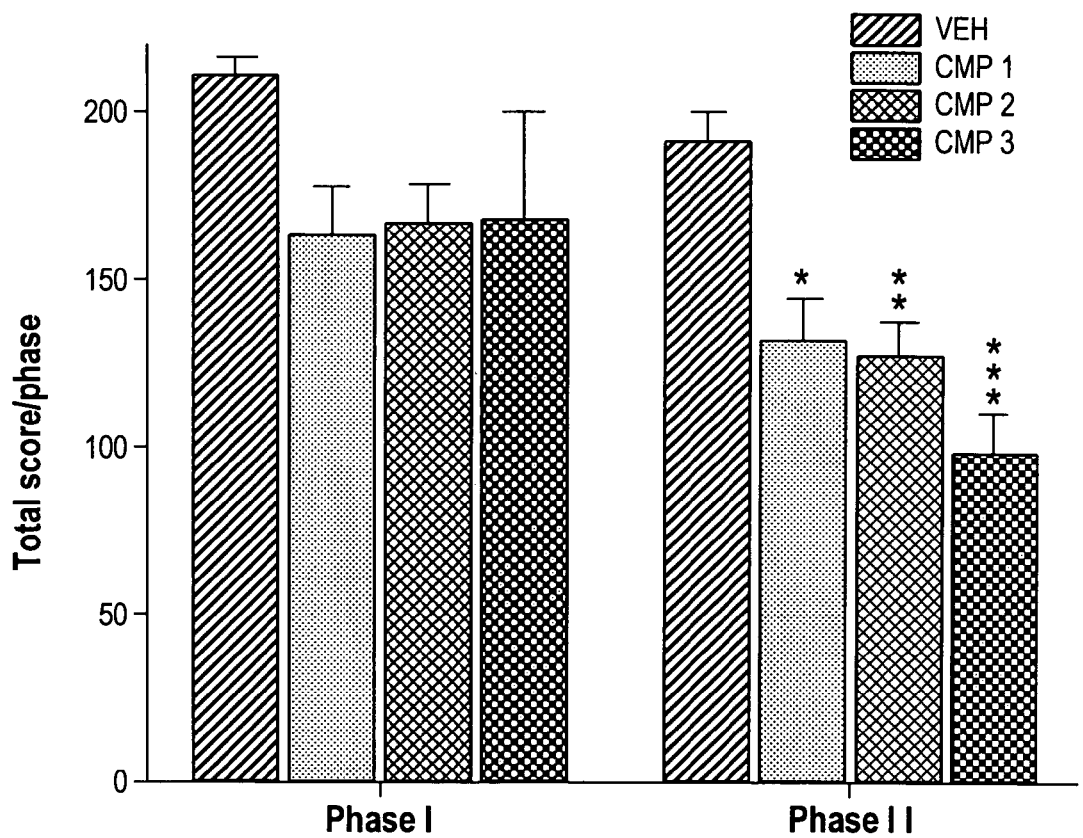
FIG. 11 illustrates the significant antinociceptive effects of Compound 11 in the Formalin Test in rats, as described in Example 5.

Results from this experiment are shown in FIG. 11. Animals were treated with vehicle (VEH) or Compound 11 (6.5 mg/kg i.p. [CMP 1]; 12.5 mg/kg i.p. [CMP 2] and 25 mg/kg i.p. [CMP 3]) 10-20 minutes before the intraplantar injection of 2.5% formalin, as described above. Compound 11 displayed a significant dose-dependent antinociceptive effect (* p<0.05;  p<0.01; * p<0.001, compared to vehicle treated group) as indicated by the attenuation of the formalin-induced spontaneous responses in Phase II.

Example 6

Writhing Test

The acetic acid abdominal contraction test (Martinez et al., Pain 1999; 81: 179) was used to determine the efficacy of different compounds in a model of acute visceral chemical nociception. Mice were given an intraperitoneal (i.p.) injection of 200 µl of 0.6% acetic acid in saline and observed for the number of abdominal contractions (writhing) they exhibited in the 30 minutes following the injection. Compound or vehicle was administered (i.p. or s.c.) 15-45 minutes prior to the acetic acid injection. Each episode of writhing is characterized by a lengthwise stretching of the torso with a concomitant arching of the back.

Statistical analysis was performed using Prism™ 4.01 software package (GraphPad, San Diego, Calif., USA). The difference in response levels between treatment groups and control vehicle group was analyzed using an ANOVA followed by Bonferroni's method for post-hoc pair-wise comparisons. A p value <0.05 was considered to be significant.

Figure 10:
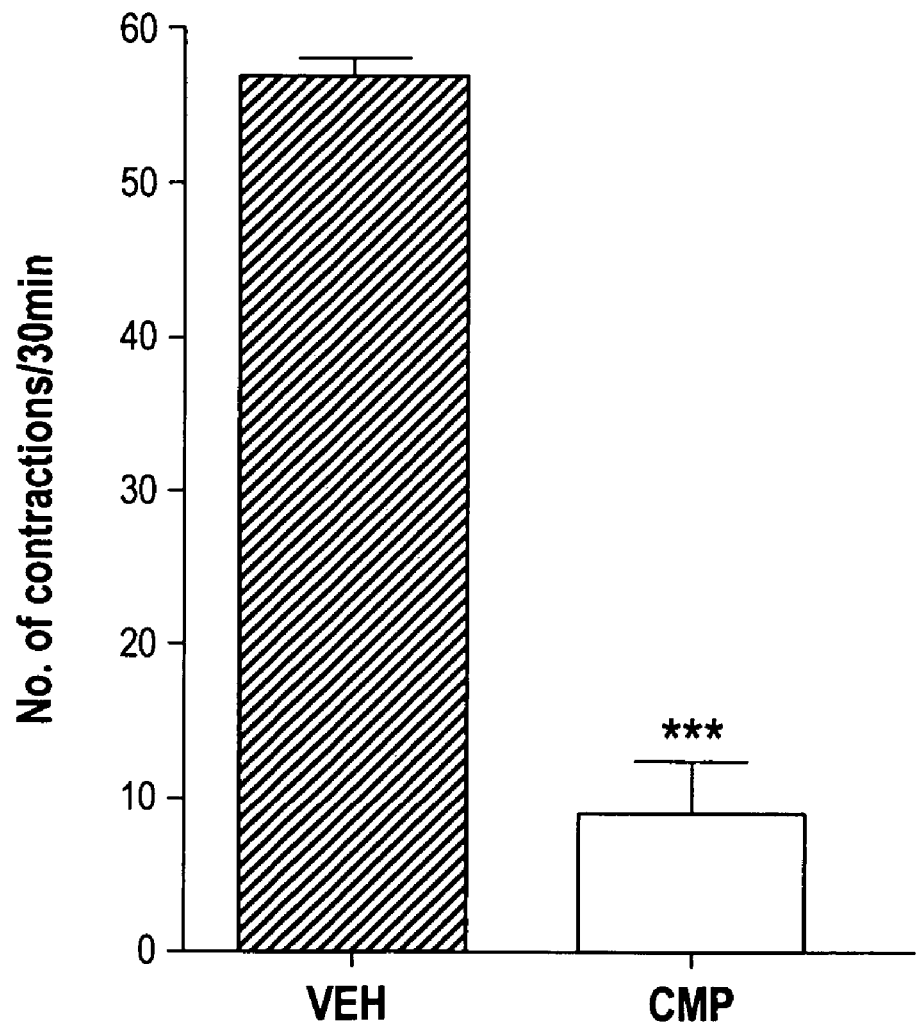
FIG. 10 illustrates the significant antinociceptive effects of Compound 63 in the Writhing Test in mice, as described in Example 6.
Figure 12:
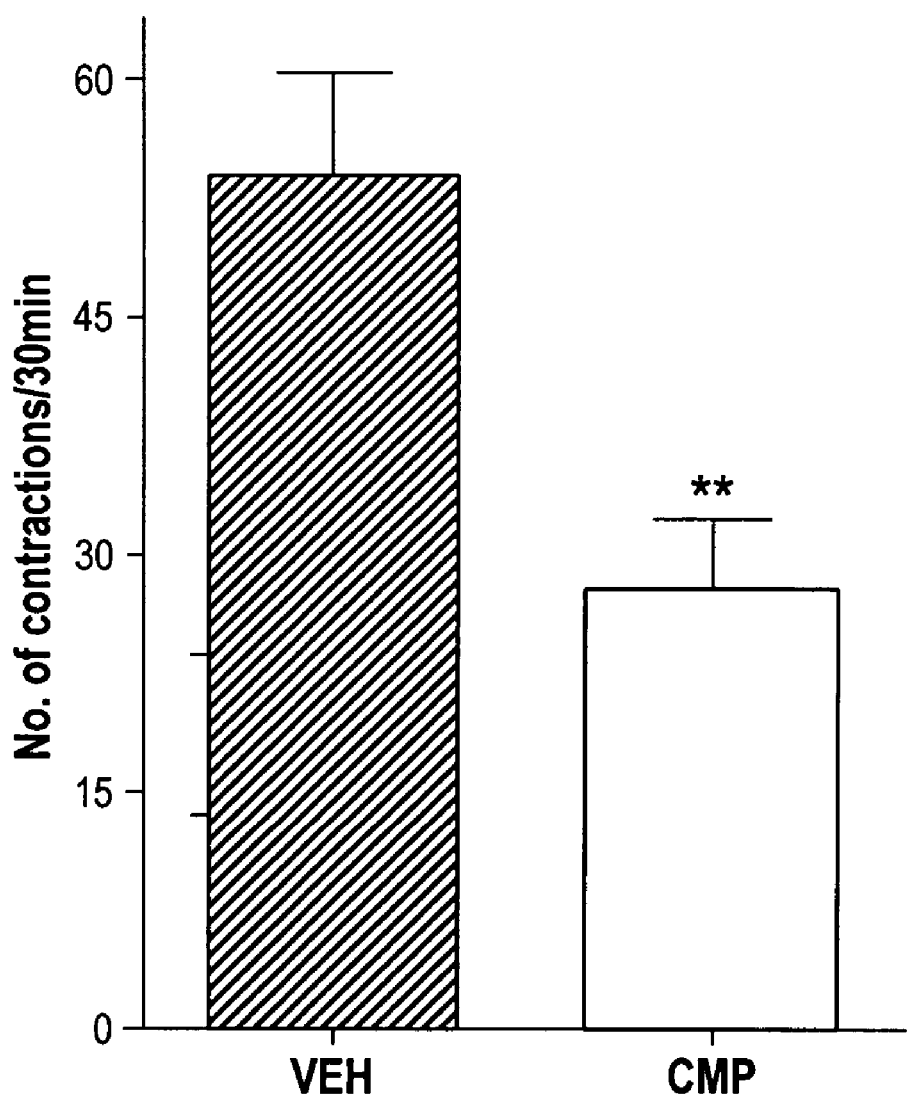
FIG. 12 illustrates the significant antinociceptive effects of Compound 11 in the Writhing Test in mice, as described in Example 6.

Results from this experiment are shown in FIGS. 10 and 12. Animals were treated with vehicle (VEH), Compound 63 (FIG. 10: 100 mg/kg i.p.; CMP) or Compound 11 (FIG. 12: 15 mg/kg i.p., [CMP]) 10-20 minutes before the intraperitoneal injection of acetic acid, as described above. Compounds 63 and 11 displayed a significant antinociceptive effect ( p<0.01; * p<0.001, compared to vehicle treated group) as indicated by the attenuation of the chemically-induced abdominal contractions (from 57±1 [n=10] to 9±3 [n=8] for Compound 63 and from 54±6 [n=7] to 28±4 [n=9] for Compound 11).

Example 7

CFA Model—Model of Chronic Nociceptive (Inflammatory Pain) Pain

Injection of complete Freunds adjuvant (CFA) in the hindpaw of the rat has been shown to produce a long-lasting inflammatory condition, which is associated with behavioural hyperalgesia and allodynia at the injection site (Hylden et al., *Pain* 1989; 37: 229). Rats (body weight 200-250 g) receive a s.c. injection of CFA (50% in saline, 100 µl, Sigma) into the plantar surface of the hindpaw under brief halothane anaesthesia. After 24 h, animals are treated with vehicle or compound (s.c. or i.p.) and, after different time-points following the treatment (e.g., 30, 60 or 90 min.), they are tested for hindpaw weight bearing responses, as assessed using an Incapacitance Tester (e.g., Linton Instrumentation, UK), (Zhu et al., 2005). The instrument incorporates a dual channel scale that separately measures the weight of the animal distributed to each hindpaw. While normal rats distribute their body weight equally between the two hindpaws (50-50), the discrepancy of weight distribution between an injured and non-injured paw is a natural reflection of the discomfort level in the injured paw (nocifensive behavior). The rats are placed in a plastic chamber designed so that each hindpaw rests on a separate transducer pad. The averager is set to record the load on the transducer over 5 s time period and two numbers displayed represent the distribution of the rat's body weight on each paw in grams (g). For each rat, three readings from each paw are taken and then averaged. Side-to-side weight bearing difference is calculated as the average of the absolute value of the difference between two hindpaws from three trials (right paw reading-left paw reading).

Example 8

Seltzer or Partial Nerve Ligation (PNL) Model (Neuropathic Pain Model)

The Partial Nerve Ligation (PNL) model (Seltzer et al., *Pain* 1990; 43:205) is used to induce chronic neuropathic pain. Male Sprague-Dawley rats are anesthetized with isoflurane, and injury to the sciatic nerve is achieved by tying a tight ligature around ⅓ to ½ of the sciatic nerve just proximal to the nerve's trifurcation in the mid-thigh. Animals develop thermal and mechanical hyperalgesia and allodynia, as well as a long-lasting spontaneous pain or dysesthesia after the nerve injury.

Mechanical allodynia testing: Pre- and post-injury baselines as well as post-treatment values (vehicle or compound-treated animals) for mechanical allodynia are evaluated using Von Frey filaments (Stoelting, Wood Dale, Ill., USA) with varying stiffness. Animals are placed on a perforated metallic platform and allowed to acclimate to their surroundings for a minimum of 30 minutes before testing. The mean and standard error of the mean (SEM) are determined for each paw in each treatment group (ipsilateral/injured paw and contralateral/non-injured paw). Since this stimulus is normally not considered painful, significant injury-induced increases in responsiveness (i.e., lower response thresholds) in this test are interpreted as a measure of mechanical allodynia. Effects of compounds are evaluated two weeks after the injury. Compound or vehicle is administered (i.p. or s.c.) and effects on mechanical allodynia are measured at different time points after dosing (e.g., 30, 60 and 90 min.).

Data analysis: Statistical analyses are conducted using Prism™ 4.01 (GraphPad, San Diego, Calif., USA). Mechanical hypersensitivity of the injured paw is determined by comparing contralateral to ipsilateral paw values within the vehicle group at each time point. Effect of vehicle (VEH) and compound are determined by comparing the post-injury baseline (BL) to post treatment values using RM-ANOVA or one-way ANOVA followed by Bonferroni's method for post-hoc pair-wise comparisons (e.g., vehicle vs compound).

Example 9

Decosterd Model or Spared Nerve Injury Model (SNI) (Neuropathic Pain Model)

The Spared Nerve Injury (SNI) model (Decosterd et al., *Pain* 2000; 87: 149) was used to induce chronic neuropathic pain. Male Sprague-Dawley rats were anesthetized with isoflurane, and two of the three terminal branches of the sciatic nerve (tibial and common peroneal nerves) were transected, leaving the remaining sural nerve intact. Animals develop thermal and mechanical hyperalgesia and allodynia, as well as spontaneous pain or dysesthesia that last month after the nerve injury.

Mechanical allodynia testing: Pre- and post-injury baselines as well as post-treatment values (vehicle or compound-treated animals) for mechanical allodynia were evaluated using Von Frey filaments (Stoelting, Wood Dale, Ill., USA) with varying stiffness. Animals were placed on a perforated metallic platform and allowed to acclimate to their surroundings for a minimum of 30 minutes before testing. The mean and standard error of the mean (SEM) were determined for each paw in each treatment group (ipsilateral/injured paw and contralateral/non-injured paw). Since this stimulus is normally not considered painful, significant injury-induced increases in responsiveness (i.e. lower response thresholds) in this test are interpreted as a measure of mechanical allodynia. Effects of compounds were evaluated two weeks after the injury. Compound or vehicle was administered (i.p. or s.c.) and effects on mechanical allodynia were measured at different time points after dosing (e.g., 30, 60 and 90 min.).

Data analysis: Statistical analyses were conducted using Prism™ 4.01 (GraphPad, San Diego, Calif., USA). Mechanical hypersensitivity of the injured paw was determined by comparing contralateral to ipsilateral paw values within the vehicle group at each time point. Effect of vehicle (VEH) and compound were determined by comparing the post-injury baseline (BL) to post treatment values using RM-ANOVA or one-way followed by Bonferroni's method for post-hoc pair-wise comparisons (e.g. vehicle vs compound).

Figure 13:
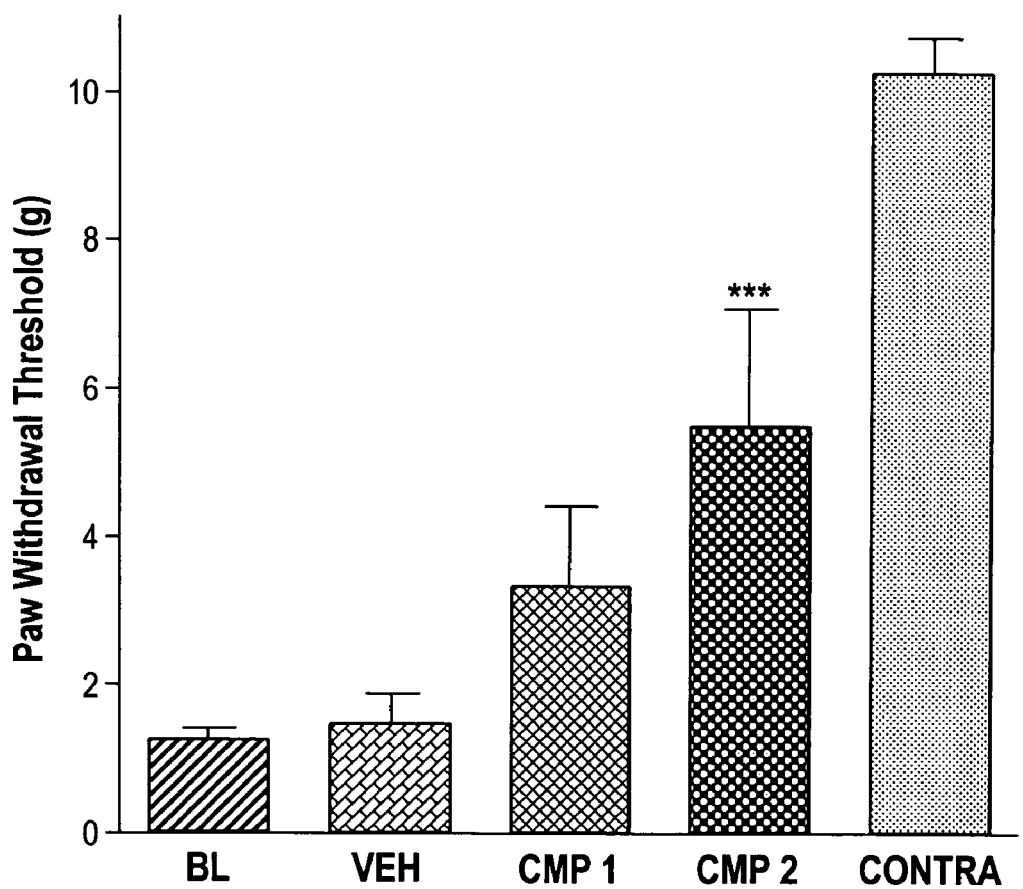
FIG. 13 shows the significant antinociceptive effects of Compound 11 in the SNI model of neuropathic pain in rats, as described in Example 9.
Figure 15:
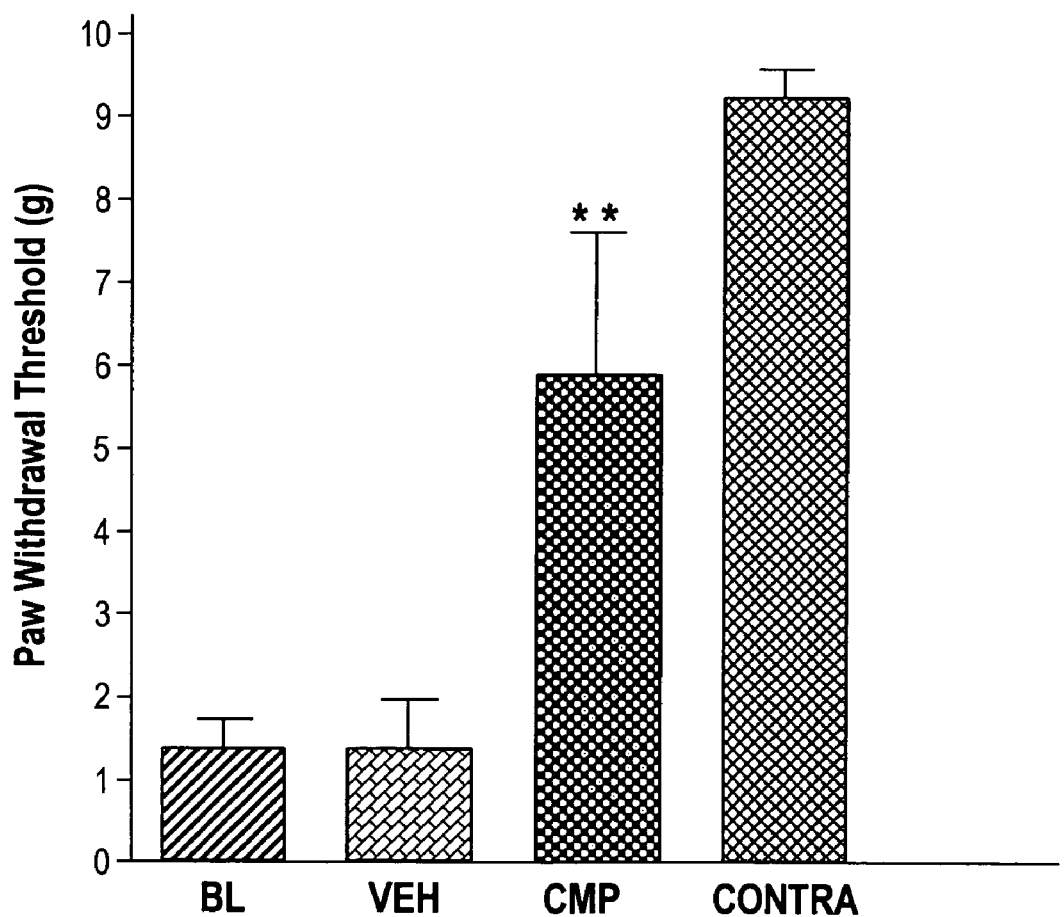
FIG. 15 shows the significant antinociceptive effects of Compound 107 in the SNI model of neuropathic pain in rats, as described in Example 9.

Results of this experiment appear in FIGS. 13 and 15, which show the antinociceptive effects of Compounds 11 and 107 in neuropathic conditions. Injury to the sciatic nerve was induced according to the SNI model, as described herein in this Example. Neuropathic state was determined by the appearance of hyper-sensitivity (i.e., allodynia) to non-noxious mechanical stimulation with Von Frey filaments of the injured paw (IPSI) as compared to the values observed with the non-injured contralateral paw (CONTRA). Animals were then treated with vehicle (VEH) or Compound 11 (FIG. 13: 3 mg/kg i.p., [CMP 1] and 10 mg/kg i.p., [CMP 2])) or Compound 107 (FIG. 15: 20 mg/kg i.p., [CMP]) and effects on mechanical allodynia were evaluated 90 min post-treatment. When compared to pre-treatment values (BL), vehicle had no effect on mechanical sensitivity. In contrast, Compounds 11 and 107 displayed a significant dose-dependent reversal of the mechanical allodynia when compared to pre-treatment controls or vehicle treated animals ( $p<0.01$; * $p<0.001$).

Example 10

Chung or Spinal Nerve Ligation (SNL) Mode (Neuropathic Pain Model)

The Spinal Nerve Ligation (SNL) model (Kim and Chung, *Pain* 1992; 50: 355) was used to induce chronic neuropathic pain. Male Sprague-Dawley rats (Harlan, Indianapolis, Ind., USA) were anesthetized with isoflurane, the left L5 transverse process was removed, and the L5 and L6 spinal nerves were tightly ligated with 6-0 silk suture. The wound was then closed with internal sutures and external staples.

Mechanical allodynia testing: Pre- and post-injury baselines as well as post-treatment values (vehicle or compound-treated animals) for non-noxious mechanical sensitivity were evaluated using 8 Semmes-Weinstein filaments (Stoelting, Wood Dale, Ill., USA) with varying stiffness according to the up-down method (Chaplan et al., *J Neurosci Methods* 1994; 53: 55). Animals were placed on a perforated metallic platform and allowed to acclimate to their surroundings for a minimum of 30 minutes before testing. The mean and standard error of the mean (SEM) were determined for each paw in each treatment group. Since this stimulus is normally not considered painful, significant injury-induced increases in responsiveness (i.e. lower response thresholds) in this test are interpreted as a measure of mechanical allodynia. Effects of compounds were evaluated two weeks after the injury. Compound or vehicle was administered (i.p. or s.c.) and effects on mechanical allodynia were measured at different time points after dosing (e.g., 30, 60 and 90 min.). Injections were performed by a separate experimenter who was not involved in testing the animals.

Data analysis: Statistical analyses were conducted using Prism™ 4.01 (GraphPad, San Diego, Calif., USA). Mechanical hypersensitivity of the injured paw was determined by comparing contralateral to ipsilateral paw values within the vehicle group at each time point. Data were analyzed using the Mann-Whitney test. Effect of vehicle (VEH) was tested by comparing to the post-injury baseline (BL) to post treatment values using the Friedman two-way analysis of variance by rank. Compound effect was analyzed at each time point by carrying out a one-way ANOVA followed by Bonferroni's method for post-hoc pair-wise comparisons.

Figure 14:
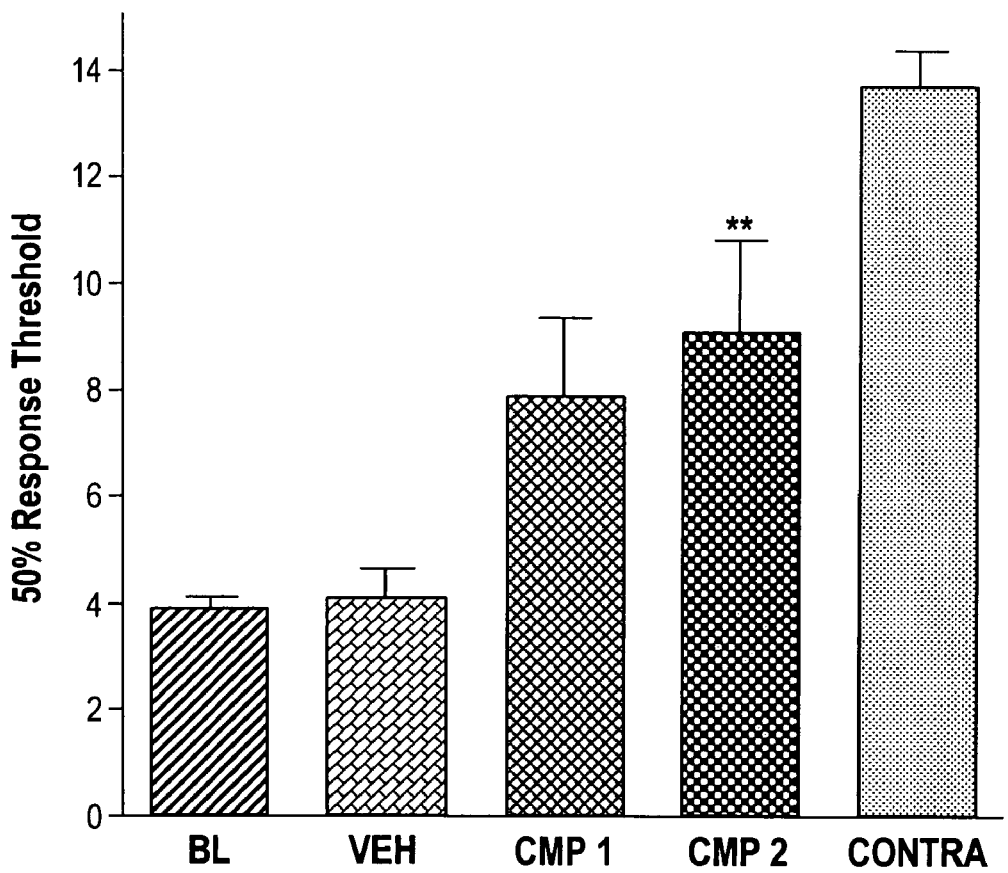
FIG. 14 shows the significant antinociceptive effects of Compound 11 in the SNL model of neuropathic pain in rats, as described in Example 10.

FIG. 14 demonstrates the antinociceptive effects of Compound 11 in neuropathic conditions. Injury to the sciatic nerve was induced according to the Chung model, as described in this example. Neuropathic state was determined by the appearance of hyper-sensitivity (i.e., allodynia) to non-noxious mechanical stimulation with Von Frey filaments of the injured paw (IPSI) as compared to the values observed with the non-injured contralateral paw (CONTRA). Animals were then treated with vehicle (VEH) or Compound 11 (5 mg/kg i.p., [CMP 1] and 10 mg/kg i.p., [CMP 2])) and effects on mechanical allodynia were evaluated 90 min post-treatment. When compared to pre-treatment values (BL), vehicle had no effect on mechanical sensitivity. In contrast, Compound 11 displayed a significant dose-dependent reversal of the mechanical allodynia when compared to pre-treatment controls or vehicle treated animals (** $p<0.01$).

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications and other references cited herein are hereby expressly incorporated herein in their entireties by reference. The entire contents of copending applications attorney docket number PCI-030, filed on even date herewith, titled "METHODS OF MODULATING NEUROTROPHIN-MEDIATED ACTIVITY"; and attorney docket number PCI-049, filed on even date herewith, titled "METHODS OF MODULATING NEUROTROPHIN-MEDIATED ACTIVITY" are expressly incorporated herein, in their entirety, as applied to the compounds of the present invention.

The invention claimed is:
1. A compound of the Formula 7,

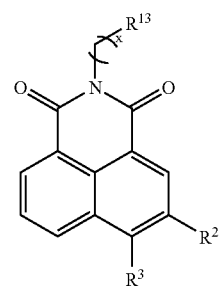

(7)

and pharmaceutically acceptable salts, enantiomers, stereoisomers, rotamers, tautomers, diastereomers, or racemates thereof;
wherein
$R^{13}$ is selected from the group consisting of —COOH, imidazolyl, —SO$_3$H, —OSO$_3$H, —OH, morpholino, piperazinyl, —PO$_3$H, —PO$_3$C$_{1-4}$alkyl and —NO$_2$; $R^2$ and $R^3$ are each, independently, selected from the group consisting of a hydrogen atom, C(O)N(R$^8$)R$^9$, N(R$^8$)R$^9$, CH$_2$N(R$^8$)R$^9$ and CH(CH$_3$)N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;
or N(R$^8$)R$^9$ is pyrrolyl, tetrazolyl, pyrrolidinyl, pyrrolidin-2-one, dimethylpyrrolyl, imidazolyl, morpholino or

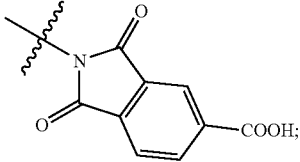

provided that at least one of R$^2$ and R$^3$ not —H; and
x is 1, 2, 3 or 4.

2. The compound of claim 1, wherein
R$^{13}$ is selected from the group consisting of —COOH, imidazolyl, —SO$_3$H, —OSO$_3$H, —OH, morpholino, piperazinyl, —PO$_3$H, —PO$_3$C$_{1-4}$alkyl and —NO$_2$;
R$^2$ and R$^3$ are each, independently, selected from the group consisting of a hydrogen atom and NH$_2$,
provided that at least one of R$^2$ and R$^3$ not hydrogen; and
x is 2, 3 or 4.

3. The compound of claim 1, wherein
R$^{13}$ is selected from the group consisting of —COOH and —COO$^-$Na$^+$;
R$^2$ is —NH$_2$ or —N(H)C(O)CH$_3$
R$^3$ is a hydrogen atom; and
x is 3.

4. The compound of claim 1, wherein
R$^2$ is pyrrolyl or pyrrolyl substituted by one or more methyl groups;
R$^3$ is —H; and
x is 2 or 3.

5. The compound of claim 1, wherein R$^2$ is NH$_2$ or NHC(O)CH$_3$ and R$^3$ is —H.

6. The compound of claim 1, wherein R$^2$ is pyrrolyl or 2,5-dimethyl-pyrrolyl and R$^3$ is —H; or R$^2$ is —H and R$^3$ is pyrrolyl or 2,5-dimethyl-pyrrolyl.

7. The compound of claim 1, wherein the compound is selected from the group consisting of 4-(5-Amino-1,3-dioxo-1H,3H-benzo[de]isoquinolin-2-yl)-butyric acid (1), Sodium 4-(5-amino-1,3-dioxo-1H,3H-benzo[de]isoquinolin-2-yl)-butyrate(2), 4-(5-Acetylamino-1,3-dioxo-1H,3H-benzo[de]isoquinolin-2-yl)-butyric acid (13), 4-(5-Carbamoyl-1,3-dioxo-1H,3H-benzo[de]isoquinolin-2-yl)-butyric acid (95), 4-(5-Acetylamino-1,3-dioxo-1H,3H-benzo[de]isoquinolin-2-yl)-butyric acid, 4-(1,3-Dioxo-5-pyrrol-1-yl-1H,3H-benzo[de]isoquinolin-2-yl)-butyric acid (122), and 4-[5-(2,5-Dimethyl-pyrrol-1-yl)-1,3-dioxo-1H,3H-benzo[de]isoquinolin-2-yl]-butyric acid (125).

8. A compound of the Formula 11,

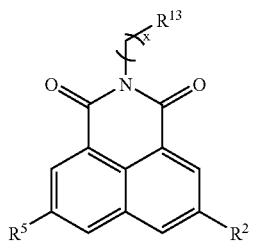

(11)

and pharmaceutically acceptable salts, enantiomers, stereoisomers, rotamers, tautomers, diastereomers, or racemates thereof;
wherein
R$^{13}$ is selected from the group consisting of a hydrogen atom, C$_{1-6}$-alkyl, amino, C$_{1-6}$-alkoxy, —OH, halogen, acid, cyano, C$_{1-6}$-alkyl-sulfonamide, aryl, heteroaryl, C$_{3-6}$-cycloalkyl, C$_{3-6}$-heterocycloalkyl, C$_{1-6}$-alkyl-amide, C$_{1-6}$-alkyl-ester, furanyl, thiophenyl, thiazolyl, nitro, C$_{1-6}$-alkene, tetrazolyl, SO$_2$—C$_{1-6}$-alkyl, SO$_3$—C$_{1-6}$-alkyl, C$_{1-6}$-alkyl-urea, C$_{1-6}$-alkyl-thiourea, morpholino, piperidinyl, piperazinyl, imidazolyl, or azepanyl;
R$^2$ and R$^5$ independently selected from selected from the group consisting of halogen, acid, CN, NO$_2$, C(O)N(R$^8$)R$^9$, N(R$^8$)R$^9$, CH$_2$N(R$^8$)R$^9$ and CH(CH$_3$)N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —OC$_{1-4}$alkyl, —SC$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl;
or N(R$^8$)R$^9$ is pyrrolyl, tetrazolyl, pyrrolidinyl, pyrrolidin-2-one, dimethylpyrrolyl, imidazolyl, morpholino,

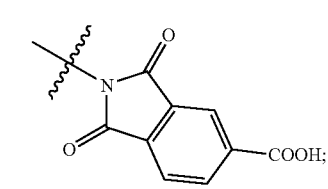

and
x is 0, 1, 2, 3 or 4.

9. The compound of claim 8, wherein R$^2$ and R$^5$ are independently selected from the group consisting of halogen, —NH$_2$, —NO$_2$, —N(H)C(O)C$_{1-6}$, COOH, tetrazolyl and CN.

10. The compound of claim 8, wherein
R$^{13}$ is selected from the group consisting of —COOH, —COO$^-$Na$^+$, COOCH$_3$, COOEt, PO$_3$H$_2$, imidazolyl, —SO$_3$H, —OSO$_3$H, —OH, morpholino, piperazinyl, —PO$_3$H, —PO$_3$C$_{1-4}$alkyl and —NO$_2$; and
x is 2, 3 or 4.

11. The compound of claim 10, wherein x is 0, 1, 2, or 3; and
R$^2$ and R$^5$ are both either —NH$_2$ or —N(H)C(O)CH$_3$.

12. The compound of claim 10, wherein x is 2 or 3; and
R$^2$ and R$^5$ are both either NO$_2$, NH$_2$ or N(H)C(O)CH$_3$.

13. The compound of claim 10, wherein x is 2 or 3, R$^{13}$ is SO$_3$H, COOH, COO$^-$Na$^+$ or COOEt; and
R$^2$ and R$^5$ are both either NO$_2$, NH$_2$ or N(H)C(O)CH$_3$.

14. The compound of claim 10, wherein x is 0, 1, 2, or 3; and
one of R$^2$ or R$^5$ are NO$_2$ and the other is Br.

15. The compound of claim 10, wherein R$^2$ and R$^5$ are N(H)C(O)CH$_2$-t-butyl.

16. The compound of claim 10, wherein
R$^{13}$ is selected from the group consisting of —COOH and —COO$^-$Na$^+$; and
x is 3.

17. The compound of claim 10, wherein R$^{13}$ is COOH, COOEt, PO$_3$H$_2$, N(H)CH$_3$ or SO$_3$H.

18. The compound of claim 10, wherein $R^2$ and $R^5$ are both $N(H)C(O)CH_2$-t-butyl, $NO_2$, $NH_2$ or $N(H)C(O)CH_3$, or one of $R^2$ and $R^5$ is Br and the other is $NO_2$.

19. The compound of claim 10, wherein x is 2 or 3.

20. The compound of claim 8, wherein $R^2$ and $R^5$ are $C(O)N(R^8)R^9$, wherein $R^8$ and $R^9$ are each, independently, selected from the group consisting of —H, $C_{1-4}$alkyl, phenyl and benzyl.

21. The compound of claim 20, wherein $R^2$ and $R^5$ are $C(O)NH_2$.

22. The compound of claim 20, wherein $R^2$ and $R^5$ are $C(O)N(H)$-t-butyl.

23. The compound of claim 8, wherein the compound is selected from the group consisting of 4-(5,8Diamino-1,3-dioxo-1H,3H-benzo[de]isoquinolin-2-yl)-butyric acid (9), 4-(5,8-Dinitro-1,3-dioxo-1H,3H-benzo[de]isoquinolin-2-yl)-butyric acid (10), 4-(5,8-Bis-acetylamino-1,3-dioxo-1H,3H-benzo[de]isoquinolin-2-yl)-butyric acid (11), 4-(5-Bromo-8-nitro-1,3-dioxo-1H,3H-benzo[de]isoquinolin-2-yl)-butyric acid (89), 3-(5,8-Dinitro-1,3-dioxo-1H,3H-benzo[de]isoquinolin-2-yl)-propane-1-sulfonic acid (105), 3-(5,8-Diamino-1,3-dioxo-1H,3 H-benzo[de]isoquinolin-2-yl)-propane-1-sulfonic acid (106), 3-(5,8-Bis-acetylamino-1,3-dioxo-1H,3H-benzo[de]isoquinolin-2-yl)-propane-1-sulfonic acid (107), 4-(5,8-Bis-acetylamino-1,3-dioxo-1H,3H-benzo[de]isoquinolin-2-yl)-butyric acid ethyl ester (108), 4-[5,8-Bis-(3,3-dimethyl-butyrylamino)-1,3-dioxo-1H,3H-benzo[de]isoquinolin-2-yl]-butyric acid (109), 4-(5,8-Dinitro-1,3-dioxo-1H,3H-benzo[de]isoquinolin-2-yl)-butyric acid ethyl ester (110), 4-(5,8-Diamino-1H,3H-benzo[de]isoquinolin-2-yl)-butyric acid ethyl ester (111),[3-(5,8-Dinitro-1,3-dioxo-1H,3H-benzo[de]isoquinolin-2-yl)-propyl]-phosphonic acid (116),[3-(5,8-Diamino-1,3-dioxo-1H,3H-benzo[de]isoquinolin-2-yl)-propyl]-phosphonic acid (117),[3-(5,8-Bis-acetylamino-1,3-dioxo-1H,3H-benzo[de]isoquinolin-2-yl)-propyl]-phosphonic acid (118), 3-(5,8-Dinitro-1,3-dioxo-1H,3H-benzo[de]isoquinolin-2-yl)-propionic acid (119), 3-(5,8-Diamino-1,3-dioxo-1H,3H-benzo[de]isoquinolin-2-yl)-propionic acid (120) and 3-(5,8-Bis-acetylamino-1,3-dioxo-1H,3H-benzo[de]isoquinolin-2-yl)-propionic acid (121).

24. A compound of the Formula 13,

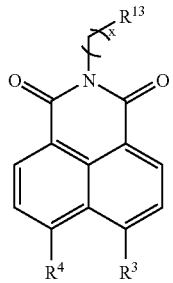

(13)

and pharmaceutically acceptable salts, enantiomers, stereoisomers, rotamers, tautomers, diastereomers, or racemates thereof;

wherein $R^{13}$ is selected from the group consisting of —COOH, —COO$^-$Na$^+$, imidazolyl, —SO$_3$H, —OSO$_3$H, —OH, morpholino, piperazinyl, —PO$_3$H, —PO$_3$C$_{1-4}$alkyl and —NO$_2$; $R^3$ and $R^4$ are independently selected from the group consisting of halogen, COOH, —NH$_2$, CN, —NO$_2$, —N(H)C(O)C$_{1-4}$ and C(O)N(R$^8$ )R$^9$, wherein $R^8$ and $R^9$ are each, independently, selected from the group consisting of —H, $C_{1-4}$alkyl, phenyl and benzyl.

25. The compound of claim 24, wherein $R^{13}$ is selected from the group consisting of —COOH, —COO$^-$Na$^+$, imidazolyl, —SO$_3$H, —OSO$_3$H, —OH, morpholino, piperazinyl, —PO$_3$H, —PO$_3$C$_{1-4}$alkyl and NO$_2$; and x is 2, 3 or 4.

26. The compound of claim 25, wherein $R^{13}$ is selected from the group consisting of —COOH and —COO$^-$Na$^+$; and x is 3.

27. The compound of claim 25, wherein $R^3$ and $R^4$ both NO$_2$, NH$_2$, or COOH.

28. The compound of claim 25, wherein x is 3, and $R^{13}$ is COOH.

29. The compound of claim 25, wherein $R^3$ and $R^4$ are C(O)NH$_2$.

30. The compound of claim 25, wherein the compound is selected from the group consisiting of 4-(6,7-Dinitro-1,3-dioxo-1H,3H-benzo[de]isoquinolin-2-yl)-butyric acid (101) and 4-(6,7-Diamino-1,3-dioxo-1H,3H-benzo[de]isoquinolin-2-yl)-butyric acid (102).

31. A compound of Formula 7A,

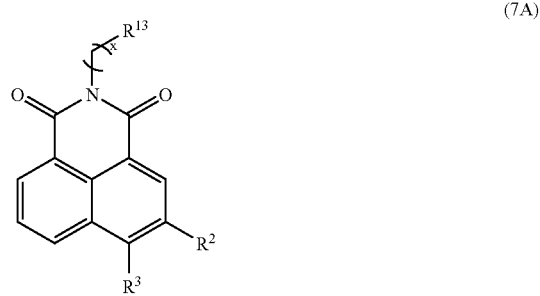

(7A)

and pharmaceutically acceptable salts, enantiomers, stereoisomers, rotamers, tautomers, diastereomers, or racemates thereof;

wherein

R—is COOH;

$R^2$ and $R^3$ are each, independently, selected from the group consisting of C(O)Ph, CN, C(O)—N-morpholino, —H, S(O)$_2$N(CH$_3$)$_2$, S(O)$_2$—N-morpholino, COOH, Cl and Br; and x is 1, 2, 3or 4.

32. The compound of claim 31, wherein $R^2$ is —H and $R^3$ is SO$_2$N(CH$_3$)$_2$; or $R^2$ is —H and $R^3$ is SO$_2$N-morpholino; or $R^2$ is SO$_2$N-morpholino and $R^3$ is —H; or $R^2$ is SO$_2$N(CH$_3$)$_2$ and $R^3$ is —H.

33. The compound of claim 31, wherein $R^2$ is —H and $R^3$ is Cl, C(O)Ph or COOH.

34. The compound of claim 31, wherein $R^3$ is —H and $R^2$ is Cl, C(O)Ph or COOH.

35. The compound of claim 31, wherein $R^{13}$ is COOH, COOEt, OH, phenyl substituted with COOH, SO$_3$H, or phenyl.

36. The compound of claim 31, wherein $R^2$ is —H and $R^3$ is CN, Br, SO$_3$H, NO$_2$ or Cl.

37. The compound of claim 32, wherein x is 1, 2 or 3.

38. The compound of claim 31, wherein the compound is selected from the group consisting of 4-(6-Bromo-1,3-dioxo-1H,3H-benzo[de]isoquinolin-2-yl)-butyric acid (73), 4-(6-Benzoyl-1,3-dioxo-1H,3H-benzo[de]isoquinolin-2-yl)-butyric acid (99), 2-(3-Carboxy-propyl)-1,3-dioxo-2,3-dihydro-1H-benzo[de]isoquinoline-6-carboxylic acid (100), 4-(6-Chloro-1,3-dioxo-1H,3H-benzo[de]isoquinolin-2-yl)-butyric acid (104), Dimethylsulfamoyl-1,3-dioxo-1H,3H-benzo[de]isoquinolin-2-yl)-butyric acid (112), 4-[6-(Morpholine-4-sulfonyl)-1,3-dioxo-1H,3H-benzo[de]isoquinolin-2-yl]-butyric acid (113), 4-(5-Dimethylsulfamoyl-1,3-dioxo-1H,3H-benzo[de]isoquinolin-2-yl)-butyric acid (114), 4-[5-(Morpholine-4-sulfonyl)-1,3-dioxo-1H,3H-benzo[de]isoquinolin-2-yl]-butyric acid (115), 3-(5-Cyano-1,3-dioxo-1H,3H-benzo[de]isoquinolin-2-yl)-propionic acid (126), 2-(3-Carboxy-propyl)-1,3-dioxo-2,3-dihydro-1H-benzo[de]isoquinoline-5-carboxylic acid (128), 4-(6-Cyano-1,3-dioxo-1H,3H-benzo[de]isoquinolin-2-yl)-butyric acid (129), 4-[6-(Morpholine-4-carbonyl)-1,3-dioxo-1H,3H-benzo[de]isoquinolin-2-yl]-butyric acid (123) and 4-(5-Cyano-1,3-dioxo-1H,3H-benzo[de]isoquinolin-2-yl)-butyric acid (124).

39. A compound of Formula 7B,

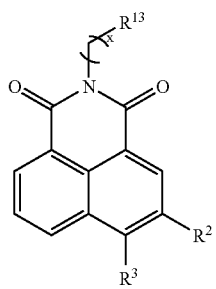

(7B)

and pharmaceutically acceptable salts, enantiomers, stereoisomers, rotamers, tautomers, diastereomers, or racemates thereof;

wherein $R^{13}$ is selected from the group consisting of phenyl, imidazolyl, morpholino, pyrrolyl, N(H)CH$_3$ and N(CH$_3$)$_2$;

$R^2$ and $R^3$ are each, independently, selected from the group consisting of —H, OH, PO$_3$H, C(O)NH$_2$, CN, SO$_3$H, NO$_2$, Br and C(O)morpholino; and x is 1, 2, 3 or 4.

40. The compound of claim 39, wherein the compound is selected from the group consisting of 5-Nitro-2-(3-pyrrol-1-yl-propyl)-benzo[de]isoquinoline-1,3-dione (34), 2-(3-Methylamino-propyl)-5-nitro-benzo[de]isoquinoline-1,3-dione (39), 2-Benzyl-5-nitro-benzo[de]isoquinoline-1,3-dione (44), 4-(6-Nitro-1,3-dioxo-1H,3H-benzo[de]isoquinolin-2-ylmethyl)-benzoic acid (79), 2-(3-Morpholin-4-yl-propyl)-5-nitro-benzo[de]isoquinoline-1,3-dione (94) and 4-(5-Nitro-1,3-dioxo-1H,3H-benzo[de]isoquinolin-2-ylmethyl)-benzoic acid (98).

41. A compound of Formula 10A,

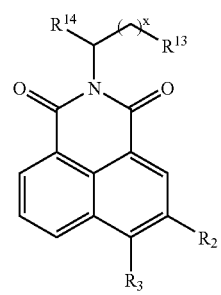

(10A)

and pharmaceutically acceptable salts, enantiomers, stereoisomers, rotamers, tautomers, diastereomers, or racemates thereof;

wherein $R^{13}$ and $R^{14}$ are each, independently, selected from the group consisting of imidazolyl, morpholino, N(CH$_3$), PO$_3$H$_2$, SO$_3$H, COOH, COOCH$_3$, COOEt, phenyl and phenyl substituted with COOH;

$R^2$ and $R^3$ are each, independently, selected from the group consisting of —H, OH, CN, SO$_3$H, S(O)$_2$N(CH$_3$)$_2$, S(O)$_2$ morpholino, C(O)morpholino, NO$_2$, C(O)NH$_2$, PO$_3$H and Br; and x is 1, 2, 3 or 4.

42. The compound of claim 41, wherein $R^{13}$ and $R^{14}$ are each, independently, selected from the group consisting of imidazolyl, morpholino, N(CH$_3$), PO$_3$H$_2$, SO$_3$H, COOCH$_3$, COOEt and phenyl substituted with COOH;

$R^2$ and $R^3$ are each, independently, selected from the group consisting of —H, OH, CN, SO$_3$H, S(O)$_2$N(CH$_3$)$_2$, S(O)$_2$ morpholino, C(O)morpholino, NO$_2$, Br; and x is 1, 2, 3 or 4.

43. The compound of claim 41, wherein $R^{13}$ and $R^{14}$ are COOH and x is 2.

44. The compound of claim 41, wherein the compound is 2-(5-Nitro-1,3-dioxo-1H,3H-benzo[de]isoquinolin-2-yl)-pentanedioic acid (43).

* * * * *